(12) United States Patent
Wright et al.

(10) Patent No.: US 10,716,618 B2
(45) Date of Patent: Jul. 21, 2020

(54) SYSTEMS AND METHODS FOR TISSUE ABLATION

(71) Applicant: Stratus Medical, LLC, Salt Lake City, UT (US)

(72) Inventors: Robert E. Wright, Denver, CO (US); Scott A. Brandt, Denver, CO (US)

(73) Assignee: Stratus Medical, LLC, Salt Lake City, UT (US)

( * ) Notice: Subject to any disclaimer, the term of this patent is extended or adjusted under 35 U.S.C. 154(b) by 218 days.

(21) Appl. No.: 15/092,945

(22) Filed: Apr. 7, 2016

(65) Prior Publication Data

US 2017/0065334 A1  Mar. 9, 2017

Related U.S. Application Data

(63) Continuation of application No. 13/101,009, filed on May 4, 2011, now abandoned.
(Continued)

(51) Int. Cl.
*A61B 18/14* (2006.01)
*A61B 18/00* (2006.01)
*A61B 18/12* (2006.01)

(52) U.S. Cl.
CPC ...... *A61B 18/1477* (2013.01); *A61B 18/1206* (2013.01); *A61B 2018/0044* (2013.01);
(Continued)

(58) Field of Classification Search
CPC .. A61B 2018/0016; A61B 2018/00166; A61B 2018/00196; A61B 2018/00208;
(Continued)

(56) References Cited

U.S. PATENT DOCUMENTS

| 4,011,872 A | 3/1977 | Kamiya |
| 4,206,761 A | 6/1980 | Cosman |

(Continued)

FOREIGN PATENT DOCUMENTS

| AU | 2017203754 | 6/2017 |
| CN | 1211171 A | 3/1999 |

(Continued)

OTHER PUBLICATIONS

Office Action issued in Japanese Application No. 2012-538056, dated Feb. 2, 2015.
(Continued)

*Primary Examiner* — Eun Hwa Kim
*Assistant Examiner* — Christine A Dedoulis
(74) *Attorney, Agent, or Firm* — Med Venture Management, LLC; Daniel C. Higgs

(57) ABSTRACT

Systems and methods for tissue ablation. Systems include needles with deployable filaments capable of producing asymmetrical offset lesions at target volumes, which may include a target nerve. Ablation of at least a portion of the target nerve may inhibit the ability of the nerve to transmit signals, such as pain signals, to the central nervous system. The offset lesion may facilitate procedures by directing energy towards the target nerve and away from collateral structures. Example anatomical structures include lumbar, thoracic, and cervical medial branch nerves and rami and the sacroiliac joint.

72 Claims, 41 Drawing Sheets

Related U.S. Application Data

(60) Provisional application No. 61/347,351, filed on May 21, 2010, provisional application No. 61/357,886, filed on Jun. 23, 2010, provisional application No. 61/357,894, filed on Jun. 23, 2010.

(52) U.S. Cl.
CPC ............... *A61B 2018/00577* (2013.01); *A61B 2018/1253* (2013.01); *A61B 2018/143* (2013.01); *A61B 2018/1427* (2013.01); *A61B 2018/1475* (2013.01)

(58) Field of Classification Search
CPC A61B 2018/00273; A61B 2018/00279; A61B 2018/0091; A61B 2018/00434; A61B 2018/0044; A61B 2018/1425; A61B 2018/1431; A61B 2018/1432; A61B 2018/1465; A61B 2018/1475; A61B 18/1477; A61B 18/1206
USPC .......................................................... 606/41
See application file for complete search history.

(56) References Cited

U.S. PATENT DOCUMENTS

| | | |
|---|---|---|
| 4,206,762 A | 6/1980 | Cosman |
| 4,281,667 A | 8/1981 | Cosman |
| 4,353,371 A | 10/1982 | Cosman |
| 4,375,220 A | 3/1983 | Matvias |
| 4,378,809 A | 4/1983 | Cosman |
| 4,385,636 A | 5/1983 | Cosman |
| 4,411,266 A | 10/1983 | Cosman |
| 4,565,200 A | 1/1986 | Cosman |
| 4,573,980 A | 3/1986 | Karrasch et al. |
| 4,583,538 A | 4/1986 | Onik et al. |
| 4,593,703 A | 6/1986 | Cosman |
| 4,618,978 A | 10/1986 | Cosman |
| 4,646,752 A | 3/1987 | Swann et al. |
| 4,653,508 A | 3/1987 | Cosman |
| 4,660,568 A | 4/1987 | Cosman |
| 4,676,255 A | 6/1987 | Cosman |
| 4,698,207 A | 10/1987 | Bringham et al. |
| 4,787,886 A | 11/1988 | Cosman |
| 4,796,615 A | 1/1989 | Bullock et al. |
| 4,827,927 A | 5/1989 | Newton |
| 4,838,265 A | 6/1989 | Cosman et al. |
| 4,886,506 A | 12/1989 | Lovgren et al. |
| 4,907,589 A | 3/1990 | Cosman |
| 4,966,597 A | 10/1990 | Cosman |
| 5,010,897 A | 4/1991 | Leveen |
| 5,160,337 A | 11/1992 | Cosman |
| 5,217,457 A | 6/1993 | Delahuerga et al. |
| 5,230,623 A | 7/1993 | Guthrie et al. |
| 5,233,515 A | 8/1993 | Cosman |
| 5,244,462 A | 9/1993 | Delahuerga et al. |
| 5,257,630 A | 11/1993 | Braitman et al. |
| 5,291,896 A | 3/1994 | Fonger et al. |
| 5,304,114 A | 4/1994 | Cosman et al. |
| 5,304,115 A | 4/1994 | Pflueger et al. |
| 5,312,329 A | 5/1994 | Beaty et al. |
| 5,312,391 A | 5/1994 | Wilk |
| 5,318,013 A | 6/1994 | Wilk |
| 5,324,255 A | 6/1994 | Passafaro et al. |
| 5,334,183 A | 8/1994 | Wuchinich |
| 5,342,292 A | 8/1994 | Nita et al. |
| 5,370,645 A | 12/1994 | Klicek et al. |
| 5,370,675 A | 12/1994 | Edwards et al. |
| 5,372,596 A | 12/1994 | Klicek et al. |
| 5,377,685 A | 1/1995 | Kazi et al. |
| 5,383,917 A | 1/1995 | Desai et al. |
| 5,397,301 A | 3/1995 | Pflueger et al. |
| 5,401,272 A | 3/1995 | Perkins |
| 5,421,923 A | 6/1995 | Clarke et al. |
| 5,422,567 A | 6/1995 | Matsunaga |
| 5,423,809 A | 6/1995 | Klicek |
| 5,433,739 A | 7/1995 | Sluijter et al. |
| 5,447,417 A | 9/1995 | Kuhl et al. |
| 5,458,597 A | 10/1995 | Edwards et al. |
| 5,472,441 A | 12/1995 | Edwards et al. |
| 5,472,442 A | 12/1995 | Klicek |
| 5,474,057 A | 12/1995 | Makower et al. |
| 5,484,398 A | 1/1996 | Stoddard |
| 5,486,161 A | 1/1996 | Lax et al. |
| 5,496,312 A | 3/1996 | Klicek |
| 5,507,743 A | 4/1996 | Edwards et al. |
| 5,507,802 A | 4/1996 | Imran |
| 5,511,564 A | 4/1996 | Wilk |
| 5,514,129 A | 5/1996 | Smith |
| D372,086 S | 7/1996 | Grasso et al. |
| 5,536,267 A | 7/1996 | Edwards et al. |
| 5,541,376 A | 7/1996 | Ladtkow et al. |
| 5,560,358 A | 10/1996 | Arnold et al. |
| 5,562,703 A | 10/1996 | Desai |
| 5,571,147 A | 11/1996 | Sluijter et al. |
| 5,580,665 A | 12/1996 | Taguchi et al. |
| 5,599,345 A | 2/1997 | Edwards et al. |
| 5,599,346 A | 2/1997 | Edwards et al. |
| 5,611,709 A | 3/1997 | McAnulty |
| 5,613,966 A | 3/1997 | Makower et al. |
| 5,628,743 A | 5/1997 | Cimino |
| 5,662,111 A | 9/1997 | Cosman |
| 5,662,620 A | 9/1997 | Lieber et al. |
| 5,662,680 A | 9/1997 | Desai |
| 5,667,486 A | 9/1997 | Lundquist et al. |
| 5,669,904 A | 9/1997 | Platt, Jr. et al. |
| 5,672,173 A | 9/1997 | Gough et al. |
| 5,672,174 A | 9/1997 | Gough et al. |
| 5,683,349 A | 11/1997 | Makower et al. |
| 5,683,384 A | 11/1997 | Gough et al. |
| 5,701,575 A | 12/1997 | Taguchi et al. |
| 5,720,744 A | 2/1998 | Eggleston et al. |
| 5,728,143 A | 3/1998 | Gough et al. |
| 5,735,847 A | 4/1998 | Gough et al. |
| 5,738,648 A | 4/1998 | Lands et al. |
| 5,748,703 A | 5/1998 | Cosman |
| 5,749,689 A | 5/1998 | Konig |
| 5,749,846 A | 5/1998 | Edwards et al. |
| 5,755,754 A | 5/1998 | Rudie et al. |
| 5,768,679 A | 6/1998 | Taguchi et al. |
| 5,772,659 A | 6/1998 | Becker et al. |
| 5,778,043 A | 7/1998 | Cosman |
| 5,782,827 A | 7/1998 | Gough et al. |
| 5,792,146 A | 8/1998 | Cosman |
| 5,797,906 A | 8/1998 | Rhum et al. |
| 5,800,484 A | 9/1998 | Gough et al. |
| 5,807,309 A | 9/1998 | Lundquist et al. |
| 5,810,804 A | 9/1998 | Gough et al. |
| 5,827,271 A | 10/1998 | Buysse et al. |
| 5,827,276 A | 10/1998 | LeVeen et al. |
| 5,848,967 A | 12/1998 | Cosman |
| 5,855,576 A | 1/1999 | LeVeen et al. |
| 5,863,290 A | 1/1999 | Gough et al. |
| 5,868,740 A | 2/1999 | LeVeen et al. |
| 5,893,847 A | 4/1999 | Kordis |
| 5,911,739 A | 6/1999 | Kordis et al. |
| 5,913,855 A | 6/1999 | Gough et al. |
| 5,921,992 A | 7/1999 | Costales et al. |
| 5,925,042 A | 7/1999 | Gough et al. |
| 5,928,229 A | 7/1999 | Gough et al. |
| 5,935,123 A | 8/1999 | Edwards et al. |
| 5,951,547 A | 9/1999 | Gough et al. |
| 5,968,040 A | 10/1999 | Swanson et al. |
| 5,980,517 A | 11/1999 | Gough |
| 5,983,141 A | 11/1999 | Sluijter et al. |
| 6,006,126 A | 12/1999 | Cosman |
| 6,013,076 A | 1/2000 | Goble et al. |
| 6,014,590 A | 1/2000 | Whayne et al. |
| 6,015,406 A | 1/2000 | Goble et al. |
| 6,016,452 A | 1/2000 | Kasevich |
| 6,039,733 A | 3/2000 | Buysse et al. |
| 6,041,260 A | 3/2000 | Stern et al. |
| 6,044,846 A | 4/2000 | Edwards |
| 6,045,532 A | 4/2000 | Eggers et al. |

(56) References Cited

U.S. PATENT DOCUMENTS

| | | | |
|---|---|---|---|
| 6,050,992 | A | 4/2000 | Nichols |
| 6,053,937 | A | 4/2000 | Edwards et al. |
| 6,059,780 | A | 5/2000 | Gough et al. |
| 6,068,627 | A | 5/2000 | Orszulak et al. |
| 6,071,280 | A | 6/2000 | Edwards et al. |
| 6,080,150 | A | 6/2000 | Gough |
| 6,090,105 | A | 7/2000 | Zepeda et al. |
| 6,105,581 | A | 8/2000 | Eggers et al. |
| 6,106,521 | A | 8/2000 | Blewett et al. |
| 6,117,134 | A | 9/2000 | Cunningham et al. |
| 6,122,341 | A | 9/2000 | Butler et al. |
| 6,129,726 | A | 10/2000 | Edwards et al. |
| 6,132,425 | A | 10/2000 | Gough |
| 6,139,519 | A | 10/2000 | Blythe |
| 6,139,547 | A | 10/2000 | Lontine et al. |
| 6,143,003 | A | 11/2000 | Cosman |
| 6,146,380 | A | 11/2000 | Racz et al. |
| 6,161,048 | A | 12/2000 | Sluijter et al. |
| 6,165,169 | A | 12/2000 | Panescu et al. |
| 6,167,295 | A | 12/2000 | Cosman |
| 6,179,834 | B1 | 1/2001 | Buysse et al. |
| 6,210,403 | B1 | 4/2001 | Klicek |
| 6,210,406 | B1 | 4/2001 | Webster |
| 6,213,999 | B1 | 4/2001 | Platt, Jr. et al. |
| 6,216,043 | B1 | 4/2001 | Swanson et al. |
| 6,217,554 | B1 | 4/2001 | Green |
| 6,221,071 | B1 | 4/2001 | Sherry et al. |
| 6,228,080 | B1 | 5/2001 | Gines |
| 6,228,083 | B1 | 5/2001 | Lands et al. |
| 6,231,570 | B1 | 5/2001 | Tu et al. |
| 6,234,178 | B1 | 5/2001 | Goble et al. |
| 6,235,023 | B1 | 5/2001 | Lee et al. |
| 6,241,725 | B1 | 6/2001 | Cosman |
| 6,241,726 | B1 | 6/2001 | Chia et al. |
| 6,246,912 | B1 | 6/2001 | Sluijter et al. |
| 6,251,106 | B1 | 6/2001 | Becker et al. |
| 6,259,952 | B1 | 7/2001 | Sluijter et al. |
| 6,268,200 | B1 | 7/2001 | Tucker et al. |
| 6,275,725 | B1 | 8/2001 | Cosman |
| 6,277,117 | B1 | 8/2001 | Tetzlaff et al. |
| 6,280,441 | B1 | 8/2001 | Ryan |
| 6,287,304 | B1 | 9/2001 | Eggers et al. |
| 6,312,426 | B1 | 11/2001 | Goldberg et al. |
| 6,330,478 | B1 | 12/2001 | Lee et al. |
| 6,331,180 | B1 | 12/2001 | Cosman et al. |
| 6,334,861 | B1 | 1/2002 | Chandler et al. |
| 6,352,536 | B1 | 3/2002 | Buysse et al. |
| 6,402,743 | B1 | 6/2002 | Orszulak et al. |
| 6,402,747 | B1 | 6/2002 | Lindermann et al. |
| 6,405,072 | B1 | 6/2002 | Cosman |
| 6,416,520 | B1 | 7/2002 | Kynast et al. |
| 6,419,653 | B2 | 7/2002 | Edwards et al. |
| 6,419,680 | B1 | 7/2002 | Cosman et al. |
| 6,419,798 | B1 | 7/2002 | Topolkaraev et al. |
| 6,425,887 | B1 | 7/2002 | McGuckin et al. |
| 6,440,127 | B2 | 8/2002 | McGovern et al. |
| 6,447,477 | B2 | 9/2002 | Burney et al. |
| 6,447,505 | B2 | 9/2002 | McGovern et al. |
| 6,451,018 | B1 | 9/2002 | Lands et al. |
| 6,454,765 | B1 | 9/2002 | Leveen et al. |
| 6,458,130 | B1 | 10/2002 | Frazier et al. |
| 6,459,769 | B1 | 10/2002 | Cosman |
| 6,461,314 | B1 | 10/2002 | Pant et al. |
| 6,464,704 | B2 | 10/2002 | Schmaltz et al. |
| 6,468,273 | B1 | 10/2002 | Leveen et al. |
| 6,471,695 | B1 | 10/2002 | Behl |
| 6,471,698 | B1 | 10/2002 | Edwards et al. |
| 6,478,793 | B1 | 11/2002 | Cosman et al. |
| 6,500,175 | B1 | 12/2002 | Gough et al. |
| 6,506,189 | B1 | 1/2003 | Rittman, III et al. |
| 6,517,534 | B1 | 2/2003 | McGovern et al. |
| 6,530,922 | B2 | 3/2003 | Cosman et al. |
| 6,533,987 | B2 | 3/2003 | Topolkaraev et al. |
| 6,551,311 | B2 | 4/2003 | Lee et al. |
| 6,562,033 | B2 | 5/2003 | Shah et al. |
| 6,565,562 | B1 | 5/2003 | Shah et al. |
| 6,569,159 | B1 | 5/2003 | Edwards et al. |
| 6,575,967 | B1 | 6/2003 | Leveen et al. |
| 6,575,969 | B1 | 6/2003 | Rittman, III et al. |
| 6,585,735 | B1 | 7/2003 | Frazier et al. |
| 6,602,249 | B1 | 8/2003 | Stoddard et al. |
| 6,605,085 | B1 | 8/2003 | Edwards |
| 6,610,054 | B1 | 8/2003 | Edwards et al. |
| 6,622,731 | B2 | 9/2003 | Daniel et al. |
| 6,623,481 | B1 | 9/2003 | Garbagnati et al. |
| 6,632,221 | B1 | 10/2003 | Edwards et al. |
| 6,632,222 | B1 | 10/2003 | Edwards et al. |
| 6,638,275 | B1 | 10/2003 | McGaffigan et al. |
| 6,641,580 | B1 | 11/2003 | Edwards et al. |
| 6,645,201 | B1 | 11/2003 | Utley et al. |
| 6,652,515 | B1 | 11/2003 | Maguire et al. |
| 6,652,516 | B1 | 11/2003 | Gough |
| 6,660,002 | B1 | 12/2003 | Edwards et al. |
| 6,660,362 | B1 | 12/2003 | Lindsay et al. |
| 6,663,624 | B2 | 12/2003 | Edwards et al. |
| 6,669,693 | B2 | 12/2003 | Friedman |
| 6,682,526 | B1 | 1/2004 | Jones et al. |
| 6,682,528 | B2 | 1/2004 | Frazier et al. |
| 6,685,701 | B2 | 2/2004 | Orszulak et al. |
| 6,689,127 | B1 | 2/2004 | Gough et al. |
| 6,690,210 | B2 | 2/2004 | Hadjizada et al. |
| 6,692,490 | B1 | 2/2004 | Edwards |
| 6,699,242 | B2 | 3/2004 | Heggeness |
| 6,706,152 | B2 | 3/2004 | Burazin et al. |
| 6,723,092 | B2 | 4/2004 | Brown et al. |
| 6,740,080 | B2 | 5/2004 | Jain et al. |
| 6,743,226 | B2 | 6/2004 | Cosman et al. |
| 6,743,229 | B2 | 6/2004 | Buysse et al. |
| 6,746,570 | B2 | 6/2004 | Burazin et al. |
| 6,749,719 | B2 | 6/2004 | Burazin et al. |
| 6,752,804 | B2 | 6/2004 | Simpson et al. |
| 6,770,070 | B1 | 8/2004 | Balbierz |
| 6,780,180 | B1 | 8/2004 | Goble et al. |
| 6,803,549 | B2 | 10/2004 | Yu |
| 6,814,712 | B1 | 11/2004 | Edwards et al. |
| 6,837,956 | B2 | 1/2005 | Cowell et al. |
| 6,846,448 | B2 | 1/2005 | Rymer et al. |
| 6,847,848 | B2 | 1/2005 | Sterzer et al. |
| 6,852,091 | B2 | 2/2005 | Edwards et al. |
| 6,866,663 | B2 | 3/2005 | Edwards et al. |
| 6,881,214 | B2 | 4/2005 | Cosman et al. |
| 6,889,089 | B2 | 5/2005 | Behl et al. |
| 6,896,675 | B2 | 5/2005 | Leung et al. |
| 6,932,810 | B2 | 8/2005 | Ryan |
| 6,958,062 | B1 | 10/2005 | Gough et al. |
| 6,958,064 | B2 | 10/2005 | Rioux et al. |
| 6,961,602 | B2 | 11/2005 | Fuimaono et al. |
| 6,962,587 | B2 | 11/2005 | Johnson et al. |
| 6,964,660 | B2 | 11/2005 | Maguire et al. |
| 6,966,908 | B2 | 11/2005 | Maguire et al. |
| 6,974,455 | B2 | 12/2005 | Garabedian et al. |
| 6,989,004 | B2 | 1/2006 | Hinchliffe et al. |
| 6,997,925 | B2 | 2/2006 | Maguire et al. |
| 7,025,767 | B2 | 4/2006 | Schaefer et al. |
| 7,033,353 | B2 | 4/2006 | Stoddard et al. |
| 7,044,949 | B2 | 5/2006 | Orszulak et al. |
| 7,048,733 | B2 | 5/2006 | Hartley et al. |
| 7,056,320 | B2 | 6/2006 | Utley et al. |
| 7,074,484 | B2 | 7/2006 | Topolkaraev et al. |
| 7,076,399 | B2 | 7/2006 | Godara |
| 7,087,051 | B2 | 8/2006 | Bourne et al. |
| 7,099,712 | B2 | 8/2006 | Fuimaono et al. |
| 7,108,696 | B2 * | 9/2006 | Daniel ............... A61B 18/1477 606/41 |
| 7,112,197 | B2 | 9/2006 | Hartley et al. |
| 7,115,124 | B1 | 10/2006 | Xiao |
| 7,138,088 | B2 | 11/2006 | Wariar et al. |
| 7,150,743 | B2 | 12/2006 | Zvuloni et al. |
| 7,150,744 | B2 | 12/2006 | Edwards et al. |
| 7,160,296 | B2 | 1/2007 | Pearson et al. |
| 7,163,536 | B2 | 1/2007 | Godara |
| 7,179,256 | B2 | 2/2007 | Mest |
| 7,179,258 | B2 | 2/2007 | Buysse et al. |
| 7,207,990 | B2 | 4/2007 | Lands et al. |

(56) References Cited

U.S. PATENT DOCUMENTS

| | | |
|---|---|---|
| 7,229,438 B2 | 6/2007 | Young |
| 7,258,688 B1 | 8/2007 | Shah et al. |
| 7,266,414 B2 | 9/2007 | Cornelius et al. |
| 7,270,660 B2 | 9/2007 | Ryan |
| 7,270,661 B2 | 9/2007 | Dahla et al. |
| 7,270,662 B2 | 9/2007 | Visram et al. |
| 7,276,064 B2 | 10/2007 | Paul et al. |
| 7,281,666 B2 | 10/2007 | Smith |
| 7,294,127 B2 | 11/2007 | Leung et al. |
| 7,306,596 B2 | 12/2007 | Hillier et al. |
| 7,311,702 B2 | 12/2007 | Tallarida et al. |
| 7,318,822 B2 | 1/2008 | Darmos et al. |
| 7,340,307 B2 | 3/2008 | Maguire et al. |
| 7,344,533 B2 | 3/2008 | Pearson et al. |
| RE40,279 E | 4/2008 | Sluijter et al. |
| 7,354,436 B2 | 4/2008 | Rioux et al. |
| 7,357,798 B2 | 4/2008 | Sharps et al. |
| 7,371,234 B2 | 5/2008 | Young |
| RE40,388 E | 6/2008 | Gines |
| 7,387,626 B2 | 6/2008 | Edwards et al. |
| 7,387,630 B2 | 6/2008 | Mest |
| 7,393,351 B2 | 7/2008 | Woloszko et al. |
| 7,399,299 B2 | 7/2008 | Daniel et al. |
| 7,416,549 B2 | 8/2008 | Young et al. |
| 7,419,487 B2 | 9/2008 | Johnson et al. |
| 7,449,020 B2 | 11/2008 | Edwards et al. |
| 7,458,971 B2 | 12/2008 | Zerfas et al. |
| 7,468,062 B2 | 12/2008 | Oral et al. |
| 7,480,533 B2 | 1/2009 | Cosman et al. |
| 7,517,346 B2 | 4/2009 | Sloan et al. |
| 7,524,318 B2 | 4/2009 | Young et al. |
| 7,533,002 B2 | 5/2009 | Godara |
| 7,549,986 B2 | 6/2009 | Rioux et al. |
| 7,561,907 B2 | 7/2009 | Fuimaono et al. |
| 7,593,778 B2 | 9/2009 | Chandran et al. |
| 7,596,469 B2 | 9/2009 | Godara |
| 7,615,050 B2 | 11/2009 | Cross et al. |
| 7,670,336 B2 | 3/2010 | Young et al. |
| 7,670,337 B2 | 3/2010 | Young |
| 7,678,106 B2 | 3/2010 | Lee |
| 7,678,107 B2 | 3/2010 | Young |
| 7,699,844 B2 | 4/2010 | Utley et al. |
| 7,704,248 B2 | 4/2010 | Dicarlo |
| 7,771,420 B2 | 8/2010 | Butty et al. |
| 7,794,458 B2 | 9/2010 | McIntyre et al. |
| 7,794,459 B2 | 9/2010 | Faure |
| 7,797,049 B2 | 9/2010 | Christopherson et al. |
| 7,799,021 B2 | 9/2010 | Leung et al. |
| 7,815,571 B2 | 10/2010 | Deckman et al. |
| 7,819,869 B2 | 10/2010 | Godara et al. |
| 7,819,871 B2 | 10/2010 | Paul et al. |
| 7,824,404 B2 | 11/2010 | Godara et al. |
| 7,828,796 B2 | 11/2010 | Wong et al. |
| 7,846,157 B2 | 12/2010 | Kozel |
| 7,874,986 B2 | 1/2011 | Deckman et al. |
| 7,875,025 B2 | 1/2011 | Cockburn et al. |
| 7,892,231 B2 | 2/2011 | Elliott |
| 7,896,871 B2 | 3/2011 | Bhushan et al. |
| 7,896,874 B2 | 3/2011 | Young et al. |
| 7,918,852 B2 * | 4/2011 | Tullis ............... A61B 18/1477 606/41 |
| 8,262,574 B2 | 9/2012 | Placek et al. |
| 8,512,330 B2 | 8/2013 | Epstein et al. |
| 8,518,037 B2 | 8/2013 | Young |
| 8,753,335 B2 | 6/2014 | Moshe et al. |
| 9,402,560 B2 | 8/2016 | Organ et al. |
| 9,675,406 B2 | 6/2017 | Moss et al. |
| 2001/0012956 A1 | 8/2001 | Behl et al. |
| 2002/0022864 A1 | 2/2002 | Mahvi et al. |
| 2002/0026185 A1 | 2/2002 | Gough |
| 2002/0029037 A1 | 3/2002 | Kim |
| 2002/0133148 A1 | 9/2002 | Daniel et al. |
| 2002/0143302 A1 | 10/2002 | Hinchliffe et al. |
| 2002/0188275 A1 | 12/2002 | McGuckin, Jr. |
| 2003/0018332 A1 | 1/2003 | Schmaltz et al. |
| 2003/0078595 A1 | 4/2003 | Cosman |
| 2003/0199862 A1 | 10/2003 | Simpson et al. |
| 2004/0006336 A1 | 1/2004 | Swanson |
| 2004/0015176 A1 | 1/2004 | Cosman |
| 2004/0015218 A1 | 1/2004 | Finch et al. |
| 2004/0059328 A1 | 3/2004 | Daniel et al. |
| 2004/0064137 A1 | 4/2004 | Pellegrino et al. |
| 2004/0100376 A1 | 5/2004 | Lye et al. |
| 2004/0122482 A1 | 6/2004 | Tung et al. |
| 2004/0143262 A1 | 7/2004 | Visram et al. |
| 2004/0158239 A1 | 8/2004 | Behl et al. |
| 2004/0176759 A1 | 9/2004 | Krishnamurthy et al. |
| 2004/0199179 A1 | 10/2004 | Elliott |
| 2004/0230187 A1 | 11/2004 | Lee et al. |
| 2004/0260282 A1 | 12/2004 | Gough et al. |
| 2005/0033279 A1 | 2/2005 | Edwards et al. |
| 2005/0059964 A1 | 3/2005 | Fitz |
| 2005/0085804 A1 | 4/2005 | McGaffigan |
| 2005/0101944 A1 | 5/2005 | Williams |
| 2005/0101950 A1 | 5/2005 | Gough et al. |
| 2005/0165391 A1 | 7/2005 | Maguire et al. |
| 2005/0171522 A1 | 8/2005 | Christopherson |
| 2005/0177209 A1 | 8/2005 | Leung et al. |
| 2005/0177211 A1 | 8/2005 | Leung et al. |
| 2005/0203503 A1 | 9/2005 | Edwards et al. |
| 2005/0234445 A1 | 10/2005 | Conquergood et al. |
| 2005/0240174 A1 | 10/2005 | Pearson et al. |
| 2005/0267552 A1 | 12/2005 | Conquergood et al. |
| 2005/0277918 A1 | 12/2005 | Shah et al. |
| 2006/0015161 A1 | 1/2006 | Longo et al. |
| 2006/0084965 A1 | 4/2006 | Young |
| 2006/0089635 A1 | 4/2006 | Young et al. |
| 2006/0095029 A1 * | 5/2006 | Young ............... A61B 18/148 606/41 |
| 2006/0095115 A1 | 5/2006 | Bladillah et al. |
| 2006/0111702 A1 | 5/2006 | Oral et al. |
| 2006/0122686 A1 | 6/2006 | Gilad et al. |
| 2006/0122692 A1 | 6/2006 | Gilad et al. |
| 2006/0142756 A1 | 6/2006 | Davies et al. |
| 2006/0173359 A1 | 8/2006 | Lin et al. |
| 2006/0189972 A1 | 8/2006 | Grossman |
| 2006/0200121 A1 | 9/2006 | Mowery |
| 2006/0206111 A1 | 9/2006 | Young |
| 2006/0206127 A1 | 9/2006 | Conquergood et al. |
| 2006/0206128 A1 | 9/2006 | Conquergood et al. |
| 2006/0206129 A1 | 9/2006 | Conquergood et al. |
| 2006/0206130 A1 | 9/2006 | Conquergood et al. |
| 2006/0206131 A1 | 9/2006 | Conquergood et al. |
| 2006/0206132 A1 | 9/2006 | Conquergood et al. |
| 2006/0206133 A1 | 9/2006 | Conquergood et al. |
| 2006/0206134 A1 | 9/2006 | Conquergood et al. |
| 2006/0217705 A1 | 9/2006 | Godara et al. |
| 2006/0229645 A1 | 10/2006 | Bonnette |
| 2006/0247616 A1 | 11/2006 | Edwards et al. |
| 2006/0259026 A1 | 11/2006 | Godara et al. |
| 2006/0259027 A1 | 11/2006 | Kwan et al. |
| 2006/0271036 A1 | 11/2006 | Garabedian et al. |
| 2007/0006215 A1 | 1/2007 | Epstein et al. |
| 2007/0010809 A1 | 1/2007 | Hovda et al. |
| 2007/0016183 A1 | 1/2007 | Lee et al. |
| 2007/0027449 A1 | 2/2007 | Godara et al. |
| 2007/0060921 A1 | 3/2007 | Janssen et al. |
| 2007/0112340 A1 | 5/2007 | Thomas et al. |
| 2007/0112342 A1 | 5/2007 | Pearson et al. |
| 2007/0118191 A1 | 5/2007 | Godara |
| 2007/0123964 A1 | 5/2007 | Davies et al. |
| 2007/0156136 A1 | 7/2007 | Godara et al. |
| 2007/0161905 A1 | 7/2007 | Munrow |
| 2007/0167943 A1 | 7/2007 | Janssen et al. |
| 2007/0179380 A1 | 8/2007 | Grossman |
| 2007/0179491 A1 | 8/2007 | Kratoska et al. |
| 2007/0185522 A1 | 8/2007 | Davies et al. |
| 2007/0203402 A1 | 8/2007 | Godara et al. |
| 2007/0203486 A1 * | 8/2007 | Young ............... A61B 18/148 606/41 |
| 2007/0213703 A1 | 9/2007 | Naam et al. |
| 2007/0260234 A1 | 11/2007 | Mccullagh et al. |
| 2007/0282321 A1 | 12/2007 | Shah et al. |
| 2007/0287996 A1 | 12/2007 | Rioux |

(56) References Cited

U.S. PATENT DOCUMENTS

| | | |
|---|---|---|
| 2008/0015569 A1 | 1/2008 | Saadat et al. |
| 2008/0033493 A1 | 2/2008 | Deckman et al. |
| 2008/0045939 A1 | 2/2008 | Lee |
| 2008/0045940 A1 | 2/2008 | Lee |
| 2008/0048786 A1 | 2/2008 | Feldkamp et al. |
| 2008/0065062 A1 | 3/2008 | Leung et al. |
| 2008/0154259 A1 | 6/2008 | Gough et al. |
| 2008/0161804 A1 | 7/2008 | Rioux et al. |
| 2008/0167646 A1 | 7/2008 | Godara et al. |
| 2008/0167649 A1 | 7/2008 | Edwards et al. |
| 2008/0208121 A1 | 8/2008 | Youssef et al. |
| 2008/0228180 A1 | 9/2008 | Epstein |
| 2008/0228181 A1 | 9/2008 | Godara et al. |
| 2008/0249392 A1 | 10/2008 | Mest |
| 2008/0249523 A1 | 10/2008 | McPherson et al. |
| 2008/0269558 A1 | 10/2008 | Yahagi et al. |
| 2008/0269739 A1 | 10/2008 | Young et al. |
| 2008/0275443 A1 | 11/2008 | Oral et al. |
| 2009/0024124 A1 | 1/2009 | Lefler et al. |
| 2009/0054962 A1 | 2/2009 | Lefler et al. |
| 2009/0099544 A1 | 4/2009 | Munrow et al. |
| 2009/0131790 A1 | 5/2009 | Munrow et al. |
| 2009/0138011 A1 | 5/2009 | Epstein |
| 2009/0187177 A1 | 7/2009 | Epstein |
| 2009/0187182 A1 | 7/2009 | Epstein et al. |
| 2009/0187183 A1 | 7/2009 | Epstein |
| 2009/0198232 A1 | 8/2009 | Young et al. |
| 2009/0221998 A1 | 9/2009 | Epstein et al. |
| 2009/0228001 A1 | 9/2009 | Pacey |
| 2009/0287081 A1 | 11/2009 | Grossman et al. |
| 2009/0292259 A1 | 11/2009 | Delano et al. |
| 2009/0299358 A1 | 12/2009 | Lafontaine |
| 2009/0306604 A1 | 12/2009 | Darmos et al. |
| 2010/0004651 A1 | 1/2010 | Biyani |
| 2010/0042098 A1 | 2/2010 | Cross et al. |
| 2010/0049192 A1 | 2/2010 | Holtz et al. |
| 2010/0056926 A1 | 3/2010 | Deckman et al. |
| 2010/0076303 A1 | 3/2010 | McKinley |
| 2010/0076340 A1* | 3/2010 | Eckstein ............ A61B 10/0045 600/562 |
| 2010/0099980 A1 | 4/2010 | Godara et al. |
| 2010/0114095 A1 | 5/2010 | Janssen et al. |
| 2010/0130974 A1 | 5/2010 | Young et al. |
| 2010/0185082 A1 | 7/2010 | Chandran et al. |
| 2010/0222677 A1 | 9/2010 | Placek et al. |
| 2011/0184403 A1 | 7/2011 | Brannan |
| 2011/0213356 A1 | 9/2011 | Wright et al. |
| 2013/0096549 A1 | 4/2013 | Organ et al. |
| 2017/0065335 A1 | 3/2017 | Wright et al. |

FOREIGN PATENT DOCUMENTS

| | | |
|---|---|---|
| CN | 2418844 | 2/2001 |
| CN | 1338909 A | 3/2002 |
| DE | 2124684 | 11/1972 |
| EP | 1059067 B1 | 4/2005 |
| EP | 1645235 B1 | 11/2010 |
| GB | 2423024 | 8/2006 |
| JP | 2000-507844 | 6/2000 |
| JP | 2001-527428 | 12/2001 |
| JP | 2003-527888 | 9/2003 |
| JP | 2004-267759 | 9/2004 |
| JP | 2008-516667 | 5/2008 |
| JP | 2009-504201 | 2/2009 |
| JP | 4290894 B2 | 4/2009 |
| JP | 2013-509966 | 3/2013 |
| WO | 96/04860 | 2/1996 |
| WO | 96/16606 | 6/1996 |
| WO | WO 96/29946 | 10/1996 |
| WO | 97/06740 | 2/1997 |
| WO | 97/06855 | 2/1997 |
| WO | 97/06857 | 2/1997 |
| WO | WO 97/06739 | 2/1997 |
| WO | 97/29702 | 8/1997 |
| WO | 99/25260 | 5/1999 |
| WO | 00/06046 | 2/2000 |
| WO | 01/28446 | 4/2001 |
| WO | 01/57655 | 8/2001 |
| WO | 02/22032 | 3/2002 |
| WO | 02/54941 | 7/2002 |
| WO | 2006/044105 | 4/2006 |
| WO | 2006/104682 | 10/2006 |
| WO | 2007/005830 | 1/2007 |
| WO | 2008/083044 | 7/2008 |
| WO | WO 2011/057157 | 5/2011 |
| WO | 2011/113943 | 9/2011 |
| WO | 2011/146243 | 11/2011 |

OTHER PUBLICATIONS

U.S. Appl. No. 15/092,945, filed Apr. 7, 2016, Systems and Methods for Tissue Ablation.

Barauskas et al., Investigation of radiofrequency ablation process in liver tissue by finite element modeling and experiment, *Medicina (Kaunas)*, vol. 43(4), pp. 310-325, 2007.

Berjano, Theoretical modeling for radiofrequency ablation: state-of-the-art and challenges for the future, *BioMedical Engineering OnLine*, vol. 5(24), 17 pages, Apr. 18, 2006.

Burdio et al., Bipolar Saline-enhanced Electrode for Radiofrequency Ablation: Results of Experimental Study of in Vivo Porcine Liver, *Radiology*, vol. 229(2), pp. 447-456, Nov. 2003.

Choi et al., Overlapping Ablation Using a Coaxial Radiofrequency Electrode and Multiple Cannulae System: Experimental Study in ex-Vivo Bovine Liver, *Korean Journal of Radiology*, vol. 4(2), pp. 117-123, Jun. 2003.

Chua, Clinical Anatomy of the Thoracic Dorsal Rami, Thesis at the University of Newcastle, New South Wales, Australia, 220 pages, 1994.

Derby et al., The Efficacy of a Two Needle Electrode Technique in Percutaneous Radiofrequency Rhizotomy: An Investigational Laboratory Study in an Animal Model, *Pain Physician*, vol. 9, pp. 207-214, 2006.

Govind et al., Radiofrequency neurotomy for the treatment of third occipital headache, *Journal of Neurology, Neurosurgery & Psychiatry*, vol. 74(1), pp. 88-93, Jan. 2003.

Liu et al., Abstract, Computer modeling of factors that affect the minimum safety distance required for radiofrequency ablation near adjacent nontarget structures, *Journal of Vascular and Interventional Radiology*, vol. 19(7), pp. 1079-1086, Jul. 2008, Epub. May 27, 2008.

Lord et al., Percutaneous Radio-Frequency Neurotomy for Chronic Cervical Zygapophyseal-Joint Pain, *New England Journal of Medicine*, vol. 335(23), pp. 1721-1726, Dec. 5, 2006.

Mulier et al., Electrodes and mutliple electrode systems for radiofrequency ablation: a proposal for updated terminology, *European Radiology*, vol. 15, pp. 798-808, 2005, Epub Feb. 12, 2005.

O'Rourke et al., Current status of liver tumor ablation devices, *Expert Rev. Med. Devices*, vol. 4(4), pp. 523-537, 2007.

AngioDynamics® Incorporated, RITA® StarBurst® Model 75; StarBurst® SOE Electrosurgical Device, StarBurst® XL Electrosurgical Device, MRI Compatible StarBurst® XL Device, MRI Compatible StarBurst® Semi-Flex Electrosurgical Device; Instructions for Use, (no date) in 5 pages.

AngioDynamics®, StarBurst® XL RFA Device: StarBurst® Semi-Flex RFA Device, http://www.angiodynamics.com/products/starburst-semiflex, 2011, in 2 pages.

Baylis Medical Company, Inc., Pain Management; Sinergy™ System, Apr. 2008, in 6 pages.

Baylis Medical Company, Inc., Pain Management; RF Generator V3 Platform, May 2008, in 6 pages.

Baylis Medical Company, Inc., for Thoracic Medial Branch Neurotomy; ThoraCool™ Pain Management System, 2009, in 3 pages.

Boston Scientific, LeVeen® Needle Electrodes; The Choice for Open, Laparoscopic or Percutaneous Radiofrequency Ablation, 2006, in 2 pages.

Boston Scientific, LeVeen® CoAccess™ Electrode System; Coaxial Radiofrequency Ablation Device, 2006, in 2 pages.

(56) References Cited

OTHER PUBLICATIONS

Diros Technology Inc., OWL Pain Management Sets, http://www.dirostech.com/22.php, (no date), in 3 pages.
Diros Technology Inc., OWL Sterile Single Use (Disposable) RF Probes, http://www.dirostech.com/productdetail.php?a=16&b+3, 2007, in 1 page.
Diros Technology Inc., OWL Re-Usable RF Probes, http://www.dirostech.com/productdetail.php?a=17&b=3, 2007, in 1 page.
FDA, Design Control Guidance for Medical Device Manufacturers, Mar. 11, 1997, in 53 pages.
Leibinger®, Electrodes for Neurosurgical Applications, pp. 4-10, 12 (no date).
Leibinger®, Accessories for RF-Electrosurgery; Bipolar and Monoplar Electrodes; Active and Inactive Cannulas; User Manual, Feb. 2000, in 24 pages.
NeuroTherm®, http://www.neurotherm.com/interventional_pain_prod_electrodes.htm, 2007, in 2 pages.
NeuroTherm®, One System, Multiple Applications, Mar. 2007, in 2 pages.
NeuroTherm®, RF for Pain Management; Disposable RF Electrode, (no date) in 2 pages.
NeuroTherm®, RF for Pain Management; Simplicity, (no date) in 2 pages.
Rex Medical: Quadra-Fuse; Multi-pronged Injection Needle, http://www.rexmedical.com/quadra-fuse.html, 2010, in 2 pages.
Smith & Nephew Endoscopy, Electrothermal 20S Spine System, http://endo.smith-nephew.com/fr/node.asp?NodeId=3592, (no date) in 2 pages.
Stryker Instruments, "MultiGen™ One Machine; Four Lesions; Multiple Options," Jul. 2008, in 8 pages.
International Search Report and Written Opinion of the International Searching Authority for International Application No. PCT/US2010/055744, dated Mar. 1, 2011, in 34 pages.
International Search Report and Written Opinion of the International Searching Authority for International Application No. PCT/US2011/035253 dated Aug. 18, 2011.
International Preliminary Report on Patentability issued in PCT/US2011/035253, dated Nov. 27, 2012.
Patent Examination Report issued in Australian Application No. 2011256709, dated Mar. 22, 2013.
Patent Examination Report issued in Australian Application No. 2010314930, dated Jul. 26, 2013.
Notice of Acceptance issued in Australian Application No. 2010314930, dated Oct. 14, 2013.
Notice of Acceptance issued in Australian Application No. 2011256709, dated Oct. 10, 2013.
Office Action issued in U.S. Appl. No. 12/940,974, dated Feb. 28, 2014.
Office Action issued in Japanese Application No. 2012-538056, dated May 19, 2014.
Office Action issued in U.S. Appl. No. 12/940,974, dated Jul. 7, 2014.
Office Action issued in Japanese Application No. 2013-511205, dated Aug. 4, 2014.
Office Action issued in Chinese Application No. 201180035655.7, dated Aug. 25, 2014.
Office Action issued in U.S. Appl. No. 12/940,974, dated Nov. 13, 2014.
Office Action issued in Korean Application No. 10-2012-7033363, dated Dec. 23, 2014.
Patent Examination Report issued in Australian Application No. 2014200132, dated Dec. 1, 2014.
Supplemental European Search Report and Search Opinion issued in EP Application No. 10829203.8, dated May 9, 2014.
Supplemental European Search Report and Search Opinion issued in EP Application No. 11783944, dated Jun. 23, 2014.
Biomerics LLC, Statement of Claim, *Biomerics LLC* v *Diros Technology Inc & M Medical Pty Ltd*, NSD438/2019, Federal Court of Australia, Mar. 22, 2019, 10 pages.
Diros Technology Inc, Statement of Cross Claim, *Biomerics LLC* v *Diros Technology Inc & M Medical Pty Ltd*, NSD438/2019, Federal Court of Australia, May 13, 2019, 5 pages.
Diros Technology Inc., RF Trident Cannulae, Last Accessed Aug. 20, 2019, available at https://dirostech.com/product-details/rf-tridenttrident-hybrid-cannulae/, 7 pages.
Diros Technology Inc., RF Trident Hybrid Cannulae, Last Accessed Aug. 20, 2019, available at https://dirostech.com/product-details/rf-trident-hybrid-cannulae/, 10 pages.
Food and Drug Administration, 510(k) Summary for Diros OWL Sterile Single Use Trident R.F. Insulated Cannulae Models DTR and DTRH, Jul. 30, 2015, 11 pages.
Ahmed et al., Principles of and Advances in Percutaneous Ablation, Radiology, Feb. 2011, pp. 351-369, vol. 258, No. 2.
Chen et al., Optimizing Electrode Placement Using Finite-Element Models in Radiofrequency Ablation Treatment Planning, IEEE Transactions on Biomedical Engineering, Feb. 2009, pp. 237-245, vol. 56, No. 2.
Haemmerich et al., Hepatic Bipolar Radio-Frequency Ablation Between Separated Multiprong Electrodes, IEEE Transactions on Biomedical Engineering, Oct. 2001, pp. 1145-1152, vol. 48, No. 10.
Haemmerich et al., Large-Volume Radiofrequency Ablation of ex Vivo Bovine Liver with Multiple Cooled Cluster Electrodes, Radiology, Feb. 2005, pp. 563-568, vol. 234, No. 2.
Laeseke et al., Multiple-Electrode RF Ablation Creates Confluent Areas of Necrosis: Results in in vivo Porcine Liver, Radiology, Oct. 2006, pp. 116-124.
Quaranta et al., FEM Analysis of RF Breast Ablation: Multiprobe versus Cool-tip Electrode, Anticancer Research, 2007, pp. 775-784.
Scharf et al., Ablation of Persistent Atrial Fibrillation Using Multielectrode Catheters and Duty-Cycled Radiofrequency Energy, Journal of the American College of Cardiology, Oct. 6, 2009, pp. 1450-1456, vol. 54, No. 15.
Shirato et al., Small Hepatocellular Carcinoma: Therapeutic Effectiveness of Percutaneous Radio Frequency Ablation Therapy With a LeVeen Needle Electrode, American Institute of Ultrasound in Medicine, 2002, pp. 67-76.
IP Australia, Patent Examination Report No. 2, Australian Patent Application No. 2014200132, dated Apr. 8, 2015, 3 pages.
IP Australia, Examination Report No. 1 for standard patent application, Australian Patent Application No. 2015261694, dated Sep. 27, 2017, 3 pages.
Brazilian National Institute of Industrial Property, Search Report, Brazilian Patent Application No. BR112012010199-4, dated Jul. 23, 2019, 6 pages.
Canadian Intellectual Property Office, Notification of Requisition by the Examiner, Canadian Patent Application No. 2,778,997, dated Jun. 9, 2017, 7 pages.
Canadian Intellectual Property Office, Notification of Requisition by the Examiner, Canadian Patent Application No. 2,778,997, dated May 23, 2019, 5 pages.
Intellectual Property India, Examination Report, Indian Patent Application No. 3638/DELNP/2012, dated Mar. 13, 2019, 5 pages.
Japan Patent Office, Notice of Reasons for Rejection, Japanese Patent Application No. 2012-538056, dated Feb. 2, 2015, 7 pages.
Japan Patent Office, Notice of Reasons for Rejection, Japanese Patent Application No. 2015-215570, dated Oct. 24, 2016, 15 pages.
IP Australia, Patent Examination Report No. 1, Australian Patent Application No. 2014200126, dated May 27, 2016, 6 pages.
Canadian Intellectual Proprety Office, Notification of Requisition by the Examiner, Canadian Patent Application No. 2,799,505, dated Mar. 17, 2017, 5 pages.
Canadian Intellectual Proprety Office, Notification of Requisition by the Examiner, Canadian Patent Application No. 2,799,505, dated Apr. 15, 2019, 10 pages.
CNIPA, National Intellectual Property Administration, PRC, Office Action, Chinese Patent Application No. 201510151627.1, dated Feb. 22, 2017, 8 pages.
CNIPA, National Intellectual Property Administration, PRC, Office Action, Chinese Patent Application No. 201510148998.4, dated Mar. 2, 2017, 10 pages.

(56) References Cited

OTHER PUBLICATIONS

European Patent Office, Communication Pursuant to Article 94(3) EPC, European Patent Application No. 11 783 944.9-1124, dated Feb. 28, 2018, 4 pages.
Israel Patent Office, Office Action, Israeli Patent Application No. 222965, dated May 14, 2015, 3 pages.
Intellectual Property India, Examination Report, Indian Patent Application No. 9943/DELNP/2012, dated Jul. 30, 2019, 6 pages.
Japan Patent Office, Notice of Reasons for Rejection, Japanese Patent Application No. 2013-511205, dated Feb. 9, 2015, 5 pages.
Japan Patent Office, Decision of Rejection, Japanese Patent Application No. 2013-511205, dated Aug. 10, 2015, 4 pages.
Japan Patent Office, Appeal No. 2015-21839, Notice of Reasons for Rejection, Japanese Patent Application No. 2013-511205, dated Oct. 3, 2016, 8 pages.
Japan Patent Office, Notice of Reasons for Rejection, Japanese Patent Application No. 2015-240011, dated Jan. 4, 2017, 12 pages.
Korean Intellectual Property Office, Notice to Submit Response, Korean Patent Application No. 10-2012-7033363, dated May 4, 2015, 14 pages.
Korean Intellectual Property Office, Notice to Submit Response, Korean Patent Application No. 10-2015-7004378, dated Sep. 25, 2017, 13 pages.
Mexican Institute of Industrial Property, Requirement 1, Mexican Patent Application No. MX/a/2012/013280, dated Feb. 17, 2015, 4 pages.
Mexican Institute of Industrial Property, Requirement 2, Mexican Patent Application No. MX/a/2012/013280, dated May 27, 2015, 8 pages.
United States Patent and Trademark Office, Office Action, U.S. Appl. No. 12/940,974, dated Mar. 16, 2015, 32 pages.
United States Patent and Trademark Office, Office Action, U.S. Appl. No. 15/098,673, dated Sep. 11, 2018, 6 pages.
United States Patent and Trademark Office, Office Action, U.S. Appl. No. 15/098,673, dated Jun. 18, 2019, 15 pages.
United States Patent and Trademark Office, Applicant-Initiated Interview Summary, U.S. Appl. No. 15/098,673, dated Jul. 16, 2019, 4 pages.
United States Patent and Trademark Office, Office Action, U.S. Appl. No. 15/098,673, dated Sep. 3, 2019, 17 pages.
United States Patent and Trademark Office, Applicant-Initiated Interview Summary, U.S. Appl. No. 15/098,673, dated Sep. 18, 2019, 4 pages.
European Patent Office, European Search Report and EPO Form 1703 01.91 TRI for European Patent Application No. EP 18215729.7, dated Sep. 6, 2019, 5 pages.
European Patent Office, Communication Under Rule 71(3) EPC for European Patent Application No. EP 11783944.9, dated Dec. 18, 2019, 125 pages.
Instituto Nacional Da Propriedade Industrial, Search Report for Brazilian Patent Application No. BR112012029263-3, dated Dec. 6, 2019, 8 pages.
United States Patent and Trademark Office, Applicant-Initiated Interview Summary for U.S. Appl. No. 15/098,673, dated Feb. 14, 2020, 3 pages.
United States Patent and Trademark Office, Form PTO/AIA/25, Terminal Disclaimer to Obviate a Provisional Double Patenting Rejection over a Pending "Reference" U.S. Appl. No. 15/098,673, filed Feb. 20, 2020, 2 pages.
United States Patent and Trademark Office, Office Action in U.S. Appl. No. 15/098,673, dated Mar. 19, 2020, 37 pages.
U.S. Appl. No. 12/940,974, filed Nov. 5, 2010, Methods and Systems for Spinal Radio Frequency Neurotomy.
U.S. Appl. No. 15/098,673, filed Apr. 14, 2016, Methods and Systems for Spinal Radio Frequency Neurotomy.
U.S. Appl. No. 13/101,009 (the Parent Application), filed May 4, 2011, Systems and Methods for Tissue Ablation.
U.S. Appl. No. 15/092,945 (the Present Application), filed Apr. 7, 2016, Systems and Methods for Tissue Ablation.
David Lawson Morris, Affidavit Submitted in Federal Court of Australia Case No. NSD 438 of 2019, dated Apr. 17, 2020, 29 pages.
Susanne Monica Hantos, Affidavit Submitted in Federal Court of Australia Case No. NSD 438 of 2019, dated Apr. 21, 2020, 765 pages.
Peter Darmos, Affidavit Submitted in Federal Court of Australia Case No. NSD 438 of 2019, dated Apr. 21, 2020, 116 pages.
William Samual Hunter, Affidavit Submitted in Federal Court of Australia Case No. NSD 438 of 2019, dated Apr. 6, 2020, 158 pages.
Daniel Christopher Higgs, Affidavit Submitted in Federal Court of Australia Case No. NSD 438 of 2019, dated Apr. 6, 2020, 26 pages.
IP Australia, Examination Report No. 1 for Standard Patent Application for Australian Patent Application No. 2019200358, dated Apr. 20, 2020, 3 pages.
Canadian Intellectual Property Office, Office Action for Canadian Patent Application No. 2,778,997, dated May 15, 2020, 3 pages.
United States Patent and Trademark Office, Notice of Allowance for U.S. Appl. No. 15/098,673, dated Apr. 9, 2020, 95 pages.
Canadian Intellectual Property Office, Office Action for Canadian Patent Application No. 2,799,505, dated Apr. 8, 2020, 4 pages.
European Patent Office, Decision to Grant a European Patent Pursuant to Article 97(1) EPC for European Patent Application No. 11783944.9, dated May 28, 2020, 2 pages.

\* cited by examiner

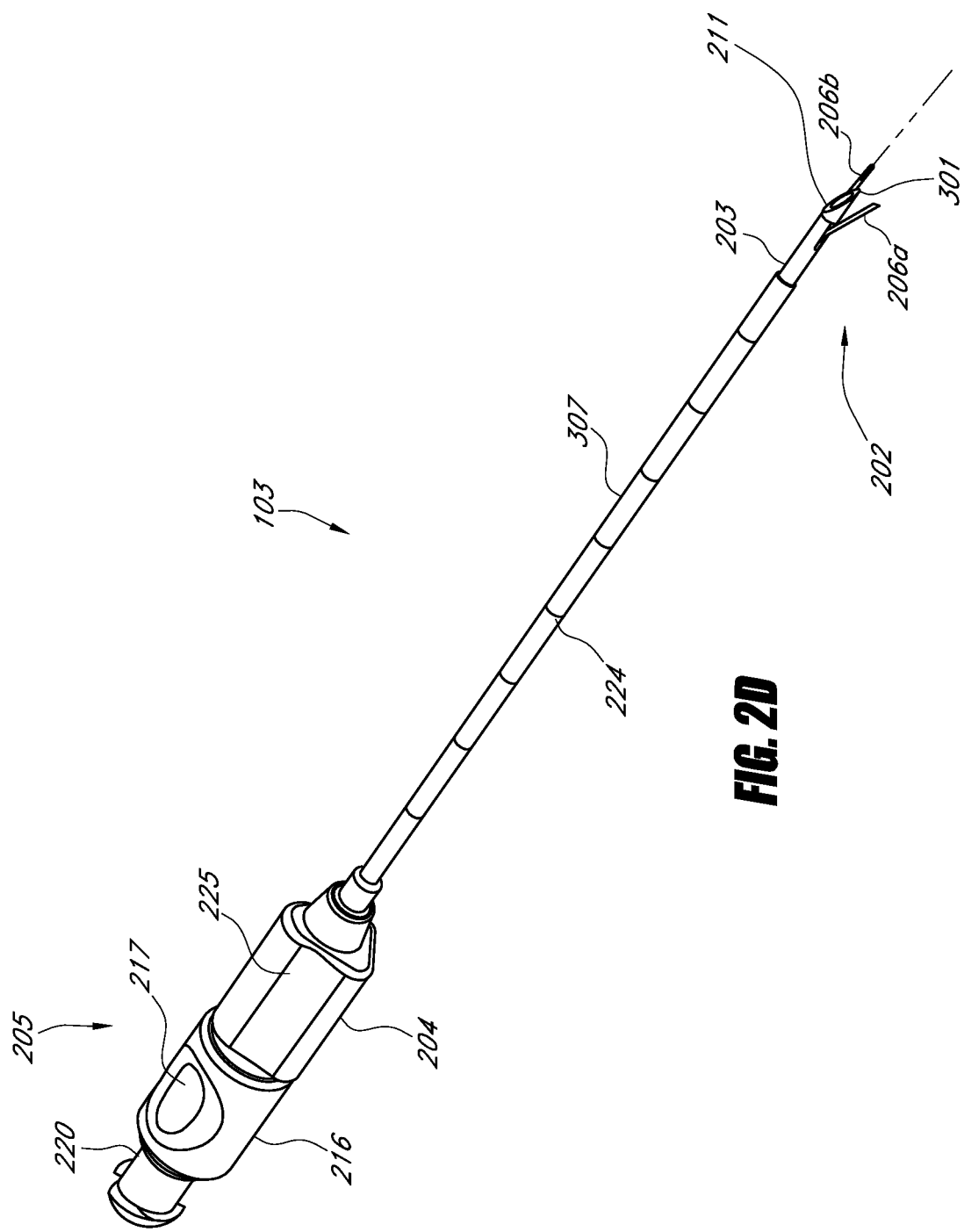

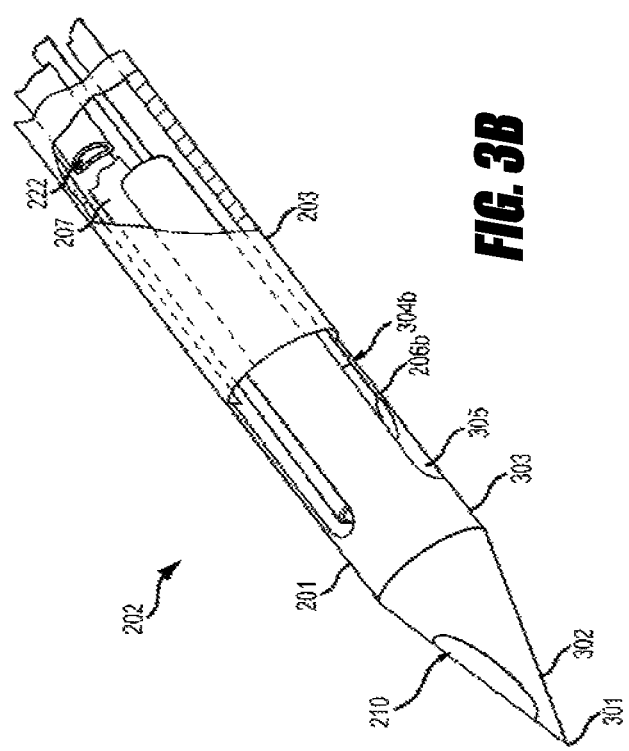

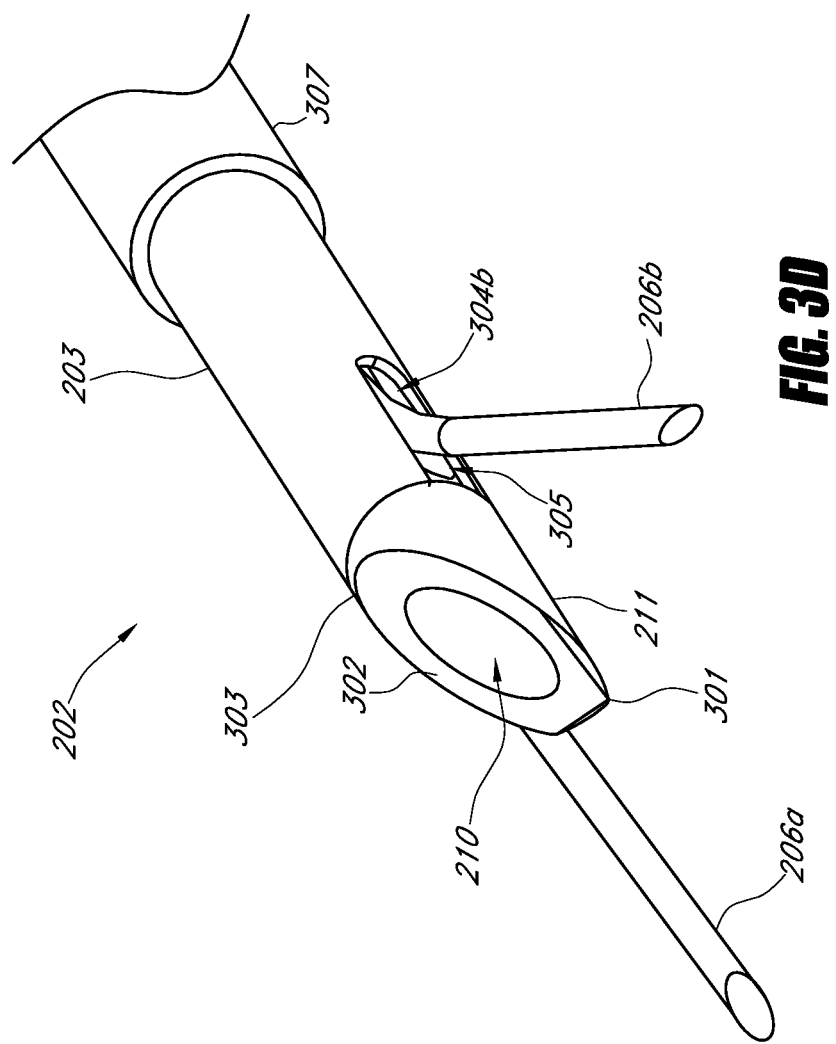

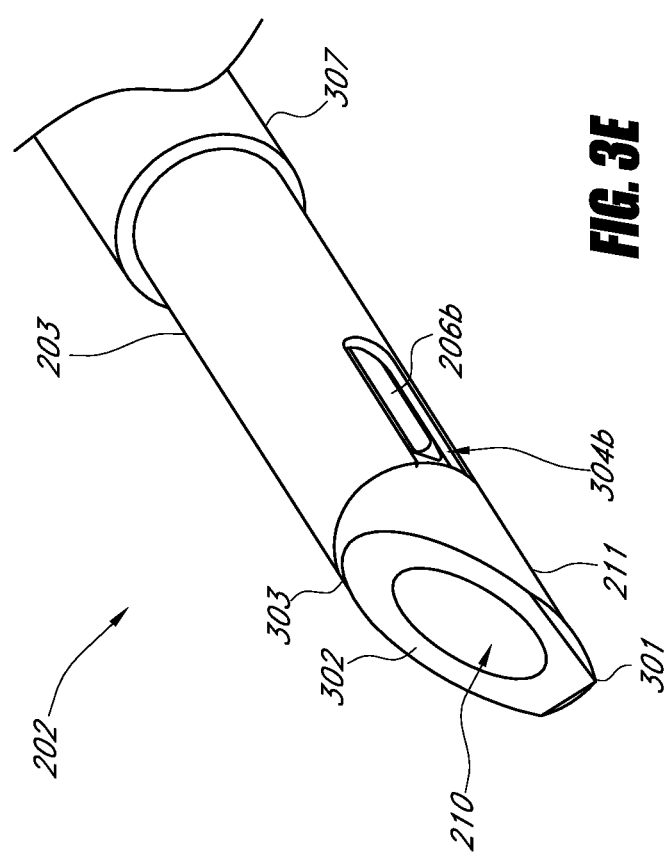

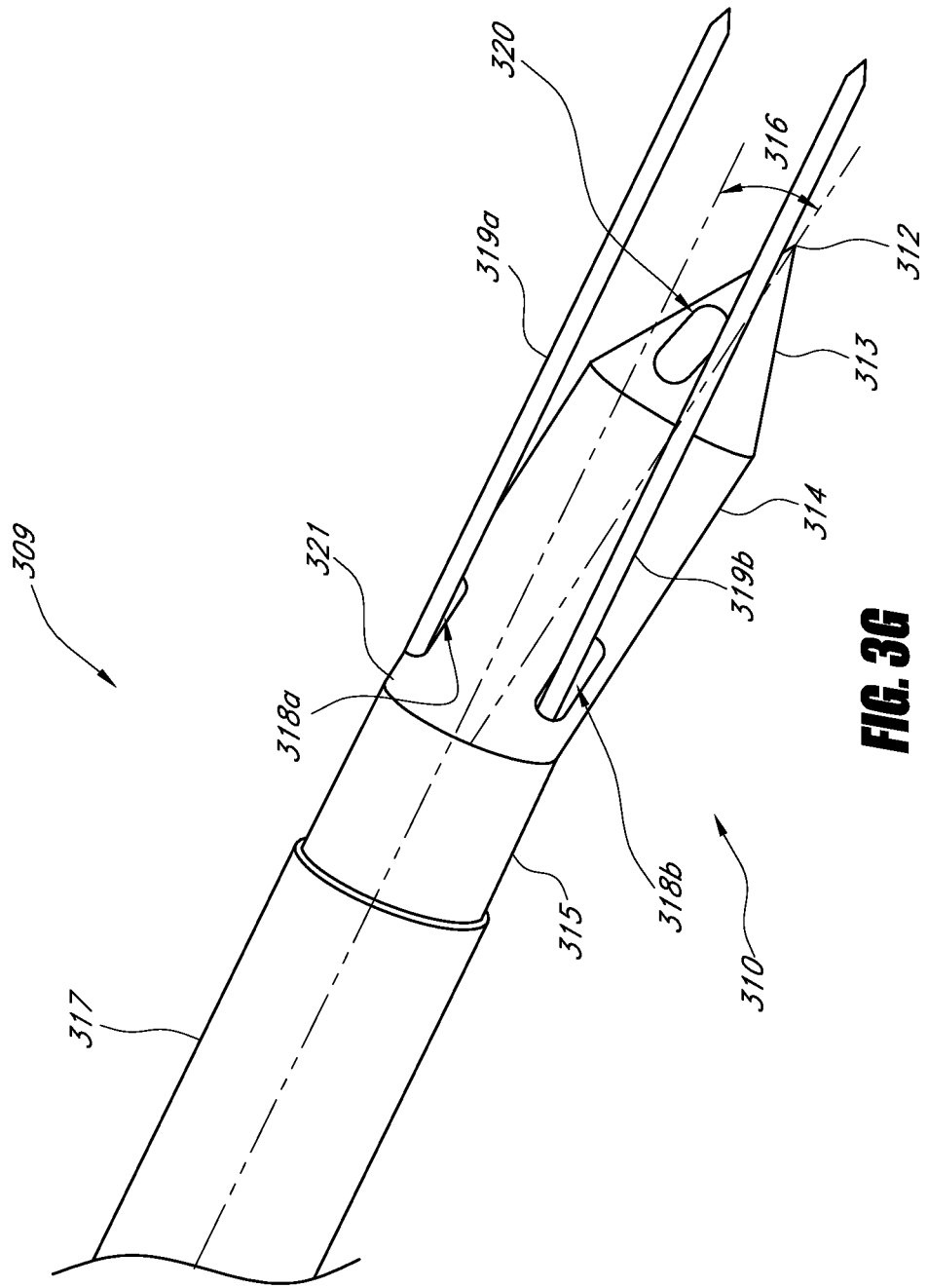

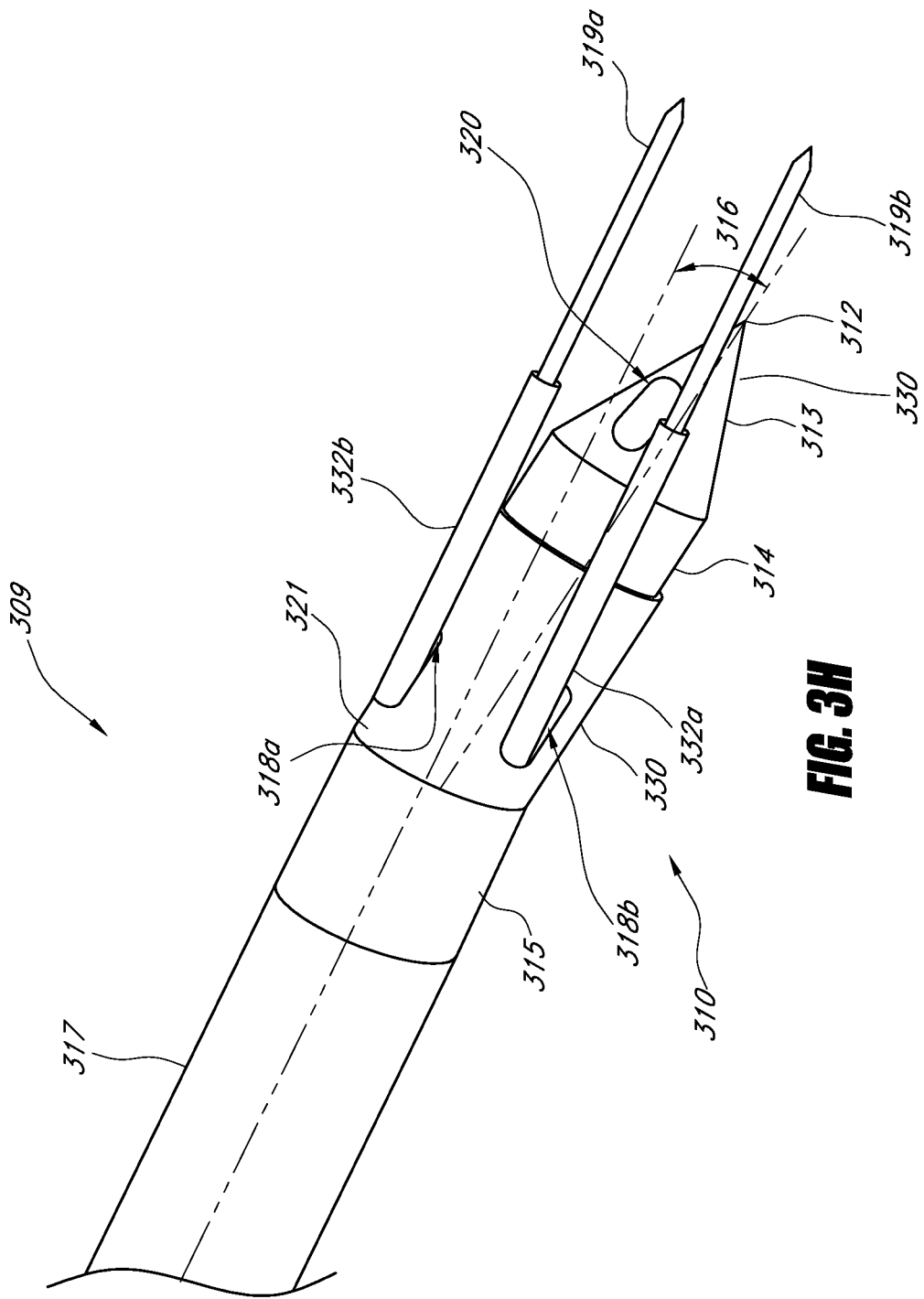

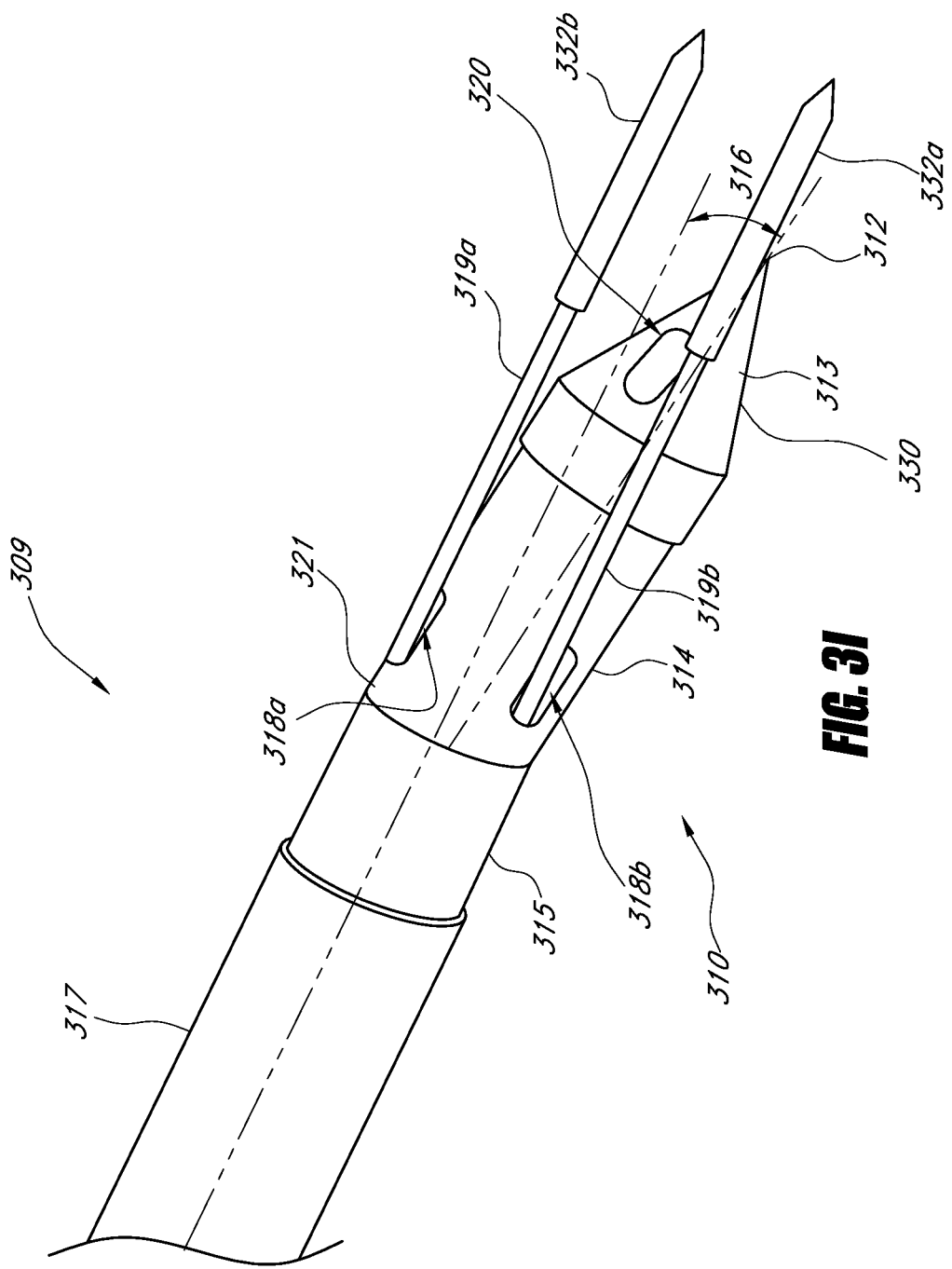

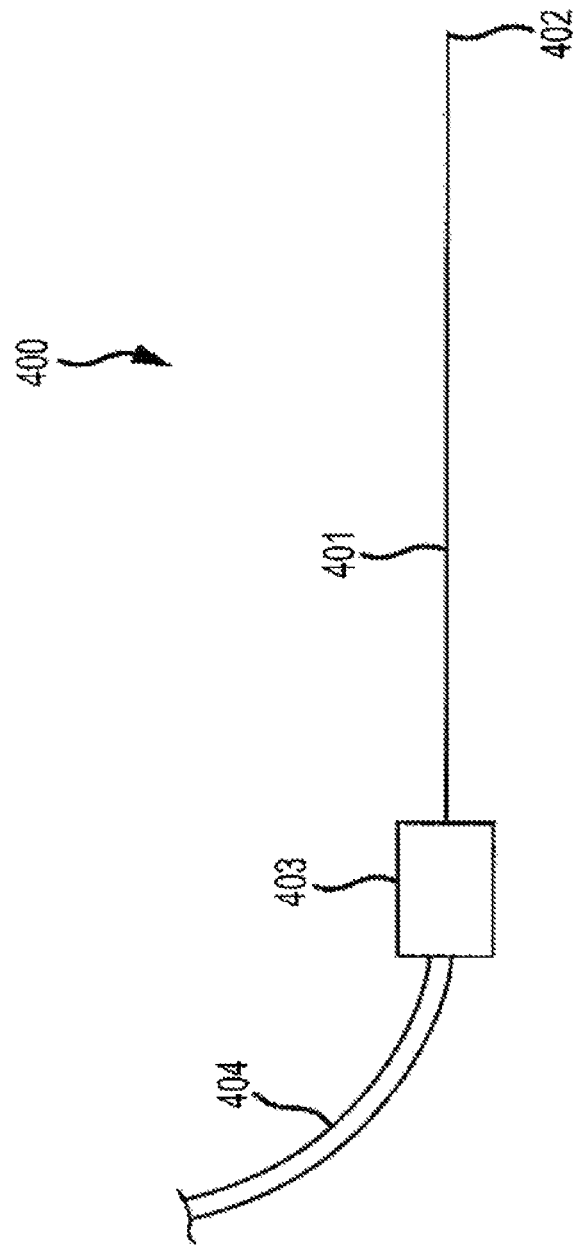

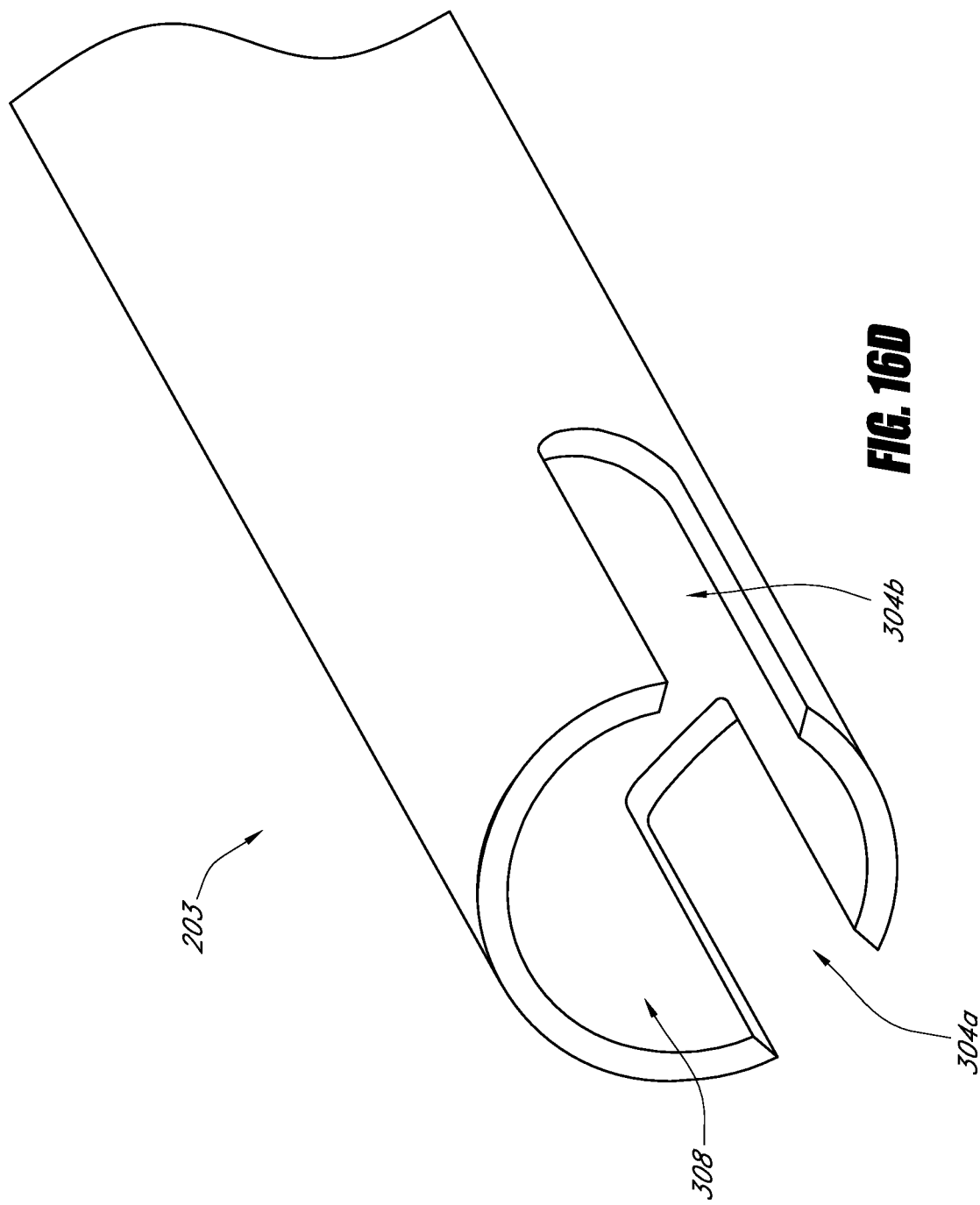

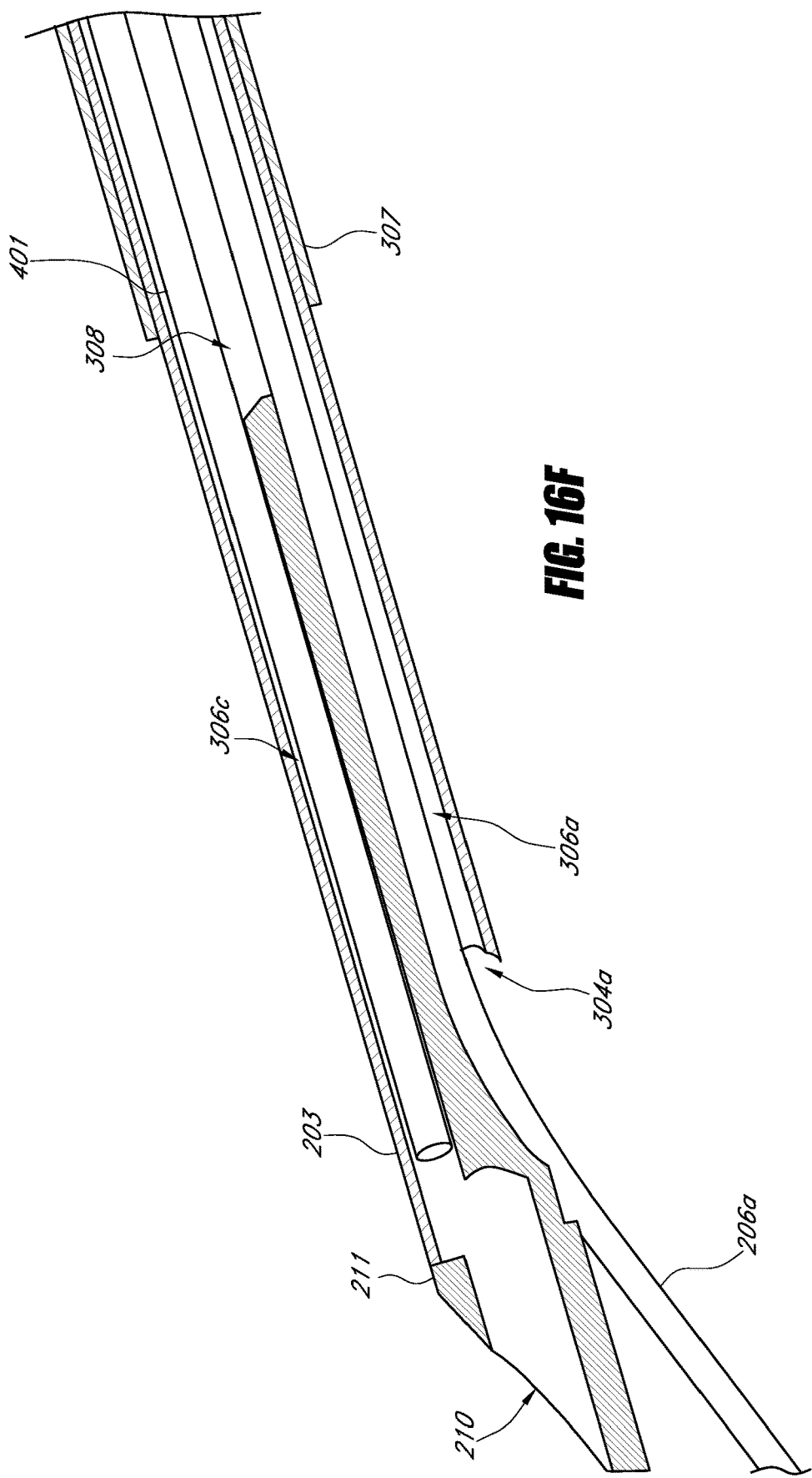

SYSTEMS AND METHODS FOR TISSUE ABLATION

CROSS-REFERENCE TO RELATED APPLICATIONS

This application is a continuation of U.S. patent application Ser. No. 13/101,009, filed May 4, 2011, which claims priority benefit under 35 U.S.C. § 119(e) of U.S. Provisional Patent Application No. 61/347,351, filed May 21, 2010, U.S. Provisional Patent Application No. 61/357,886, filed Jun. 23, 2010, and U.S. Provisional Patent Application No. 61/357,894, filed Jun. 23, 2010, each of which is incorporated herein by reference in its entirety.

BACKGROUND

Field

The present application generally relates to thermal ablation systems and methods, and more particularly to systems and methods for radio frequency (RF) neurotomy, such as spinal RF neurotomy.

Description of the Related Art

Thermal ablation involves the creation of temperature changes sufficient to produce necrosis in a specific volume of tissue within a patient. The target volume may be, for example, a nerve or a tumor. A significant challenge in ablation therapy is to provide adequate treatment to the targeted tissue while sparing the surrounding structures from injury.

RF ablation uses electrical energy transmitted into a target volume through an electrode to generate heat in the area of the electrode tip. The radio waves emanate from a non-insulated distal portion of the electrode tip. The introduced radiofrequency energy causes molecular strain, or ionic agitation, in the area surrounding the electrode as the current flows from the electrode tip to ground. The resulting strain causes the temperature in the area surrounding the electrode tip to rise. RF neurotomy uses RF energy to cauterize a target nerve to disrupt the ability of the nerve to transmit pain signals to the brain.

SUMMARY

This application describes example embodiments of devices and methods for tissue ablation, such as spinal radio frequency neurotomy. Systems include needles with deployable filaments capable of producing asymmetrical offset lesions at target volumes, which may include a target nerve. Ablation of at least a portion of the target nerve may inhibit the ability of the nerve to transmit signals, such as pain signals, to the central nervous system. The offset lesion may facilitate procedures by directing energy towards the target nerve and away from collateral structures. Example anatomical structures include lumbar, thoracic, and cervical medial branch nerves and rami and the sacroiliac joint.

In some embodiments, a needle comprises an elongate member having a distal end, a tip coupled to the distal end of the elongate member, and a plurality of filaments. The tip comprises a bevel to a point. The plurality of filaments is movable between a first position at least partially in the elongate member and a second position at least partially out of the elongate member. The plurality of filaments and the tip are configured to transmit radio frequency energy from a probe to operate as a monopolar electrode.

In some embodiments, a needle comprises an elongate member having a distal end, a tip coupled to the distal end of the elongate member, and a plurality of filaments. The tip comprises a bevel portion comprising a point on a side of the elongate member. The plurality of filaments is movable between a first position at least partially in the elongate member and a second position at least partially out of and proximate to the side of the elongate member. The plurality of filaments and the tip are configured to transmit radio frequency energy from a probe to operate as a monopolar electrode.

In some embodiments, a needle comprises an elongate member having a proximal end and a distal end, a tip coupled to the distal end of the elongate member, a plurality of filaments, and a filament deployment mechanism coupled to the proximal end of the elongate member. The tip comprises a bevel portion comprising a point. The plurality of filaments is movable between a first position at least partially in the elongate member and a second position at least partially out of the elongate member. The plurality of filaments and the tip are configured to transmit radio frequency energy from a probe to operate as a monopolar electrode. The filament deployment mechanism comprises an advancing hub, a spin collar, and a main hub. The advancing hub includes a stem coupled to the plurality of filaments. The spin collar includes a helical track. The stem of the advancing hub is at least partially inside the spin collar. The main hub comprises a stem comprising a helical thread configured to cooperate with the helical track. The stem of the main hub is at least partially inside the spin collar. The stem of the advancing hub is at least partially inside the main hub. Upon rotation of the spin collar, the filaments are configured to move between the first position and the second position.

In some embodiments, a needle comprises an elongate member having a distal end, a tip coupled to the distal end of the elongate member, and a plurality of filaments. The tip comprises a point. The plurality of filaments is movable between a first position at least partially in the elongate member and a second position at least partially out of the elongate member. The plurality of filaments and the tip are configured to transmit radio frequency energy from a probe to operate as a monopolar electrode. A single wire comprises the plurality of filaments.

In some embodiments, a needle comprises an elongate member having a distal end, a tip coupled to the distal end of the elongate member, and a plurality of filaments. The tip comprises a bevel to a point. The plurality of filaments is movable between a first position at least partially in the elongate member and a second position at least partially out of the elongate member. The plurality of filaments and the tip are configured to transmit radio frequency energy from a probe to operate as a monopolar electrode. The tip comprises a stem at least partially in the elongate member. The stem includes a first filament lumen, a second filament lumen, and a third lumen. The bevel portion comprises a fluid port in fluid communication with the third lumen.

In some embodiments, a needle comprises an elongate member having a proximal end and a distal end, a tip coupled to the distal end of the elongate member, a plurality of filaments, and a rotational deployment mechanism coupled to the proximal end of the elongate member. The tip comprises a bevel to a point. The plurality of filaments is movable between a plurality of positions between at least partially in the elongate member and at least partially out of the elongate member. The deployment mechanism comprises indicia of fractional deployment of the plurality of filaments relative to the tip. The plurality of filaments and the tip are configured to transmit radio frequency energy from a probe to operate as a monopolar electrode.

In some embodiments, a needle comprises an elongate member having a distal end, a tip, and a plurality of filaments. The tip comprises a first body portion and a second body portion. The first body portion includes a tapered portion and a point. The tapered portion includes a plurality of filament ports. The second body portion is coupled to the distal end of the tip. The second body portion is at an angle with respect to the first body portion. The plurality of filaments is movable between a first position at least partially in at least one of the tip and the elongate member and a second position at least partially out of the filament ports. The plurality of filaments and the tip are configured to transmit radio frequency energy from a probe to operate as a monopolar electrode.

In some embodiments, a method of heating a vertebral disc comprises: positioning a distal end of a needle in a posterior annulus; deploying a filament out of the needle; traversing the posterior annulus from lateral to medial; applying radio frequency energy to the tip and to the filament; and ablating pain fibers in the posterior annulus.

In some embodiments, a needle for insertion into a patient during an RF ablation procedure comprises a hub, an elongate member fixed to the hub, a tip fixed to the elongate member at a distal end of the needle, a plurality of filaments in at least a portion of the elongate member, an actuator interconnected to the plurality of filaments, and a lumen in the elongate member. The tip is shaped to pierce tissue of the patient. Movement of the actuator relative to the hub moves the plurality of filaments relative to the tip. The lumen and the tip are configured to accept an RF probe such that an electrode of an inserted RF probe, the tip, and the first and second filaments are operable to form a single monopolar RF electrode.

In some embodiments, a needle for insertion into a patient during an RF ablation procedure comprises a hub, an elongate member fixed to the hub, a tip fixed to the elongate member at a distal end of the needle, a plurality of filaments in at least a portion of the elongate member in a retracted position, and an actuator interconnected to the plurality of filaments. The actuator is operable to move the plurality of filaments relative to the hub, the elongate member, and the tip between the retracted position and a fully deployed position. In the fully deployed position, the plurality of filaments extends outwardly and away from the tip. Each filament comprises a distal end that defines a point in the fully deployed position. Each point is distal to the distal end of the needle. The average of all the points is offset from a central longitudinal axis of the elongate member.

In some embodiments, a needle for insertion into a patient during an RF ablation procedure comprises a hub, an elongate member fixed to the hub, a tip fixed to the elongate member at a distal end of the needle, a plurality of filaments in at least a portion of the elongate member in a retracted position, and an actuator interconnected to the plurality of filaments. The actuator is operable to move the plurality of filaments relative to the hub, the elongate member, and the tip between the retracted position and a deployed position. In the deployed position, the plurality of filaments extends outwardly and away from the tip. Each filament comprises a distal end that defines a point in the deployed position. Each point is distal to the distal end of the needle. Each point is on a common side of a plane that contains a central longitudinal axis of the elongate member.

In some embodiments, a needle for insertion into a patient during an RF ablation procedure comprises a hub, an elongate member fixed to the hub, a tip fixed to the elongate member at a distal end of the needle, a plurality of filaments in at least a portion of the elongate member in a retracted position, and an actuator interconnected to the plurality of filaments. The plurality of filaments consists of a first filament and a second filament, and the needle contains no filaments other than the first and second filaments. The actuator is operable to move the plurality of filaments relative to the hub, the elongate member, and the tip between the retracted position and a deployed position. In the deployed position, the plurality of filaments extends outwardly and away from the tip. Each filament comprises a distal end that defines a point in the deployed position. Each point is distal to the distal end of the needle. In the deployed position, a midpoint between the distal end of the first filament and the distal end of the second filament is offset from a central longitudinal axis of the needle.

In some embodiments, a needle for insertion into a patient during an RF ablation procedure comprises a hub, an elongate member fixed to the hub, a tip fixed to the elongate member at a distal end of the needle, a plurality of filaments in at least a portion of the elongate member in a retracted position, and an actuator interconnected to the plurality of filaments. The plurality of filaments consists of a first filament and a second filament, and the needle contains no filaments other than the first and second filaments. The actuator is operable to move the plurality of filaments relative to the hub, the elongate member, and the tip between the retracted position and a deployed position. In the deployed position, the plurality of filaments extends outwardly and away from the tip. Each filament comprises a distal end that defines a point in the deployed position. Each point is distal to the distal end of the needle. In their respective deployed positions, each distal end defines a vertex of a polygon. A centroid of the polygon is offset from a central longitudinal axis of the needle.

In some embodiments, a needle for insertion into a patient during an RF ablation procedure comprises a hub, an elongate member fixed to the hub, a tip fixed to the elongate member at a distal end of the needle, a plurality of filaments in at least a portion of the elongate member in a retracted position, and an actuator interconnected to the plurality of filaments. The plurality of filaments consists of a first filament and a second filament, and the needle contains no filaments other than the first and second filaments. The actuator is operable to move the plurality of filaments relative to the hub, the elongate member, and the tip between the retracted position and a deployed position. In the deployed position, the plurality of filaments extends outwardly and away from the tip. Each filament comprises a distal end that defines a point in the deployed position. Each point is distal to the distal end of the needle. In their respective deployed positions, each of the plurality of filaments points in an at least partially distal direction.

In some embodiments, a needle for insertion into a patient during an RF ablation procedure comprises a hub, an elongate member fixed to the hub, a tip fixed to the elongate member at a distal end of the needle, a plurality of filaments in at least a portion of the elongate member in a retracted position, and an actuator interconnected to the plurality of filaments. The plurality of filaments consists of a first filament and a second filament, and the needle contains no filaments other than the first and second filaments. The actuator is operable to move the plurality of filaments relative to the hub, the elongate member, and the tip between the retracted position and a deployed position. In the deployed position, the plurality of filaments extends outwardly and away from the tip. Each filament comprises a distal end that defines a point in the deployed position. Each point is distal to the distal end of the needle. When the plurality of filaments are in the deployed position, portions of each filament extend outwardly away from the tip. Each portion of each filament extending outwardly away from the tip is straight.

In some embodiments, a needle for insertion into a patient during an RF ablation procedure comprises a hub, an elongate member fixed to the hub, a tip fixed to the elongate member at a distal end of the needle, a plurality of filaments in at least a portion of the elongate member in a retracted position, and an actuator interconnected to the plurality of filaments. The plurality of filaments consists of a first filament and a second filament, and the needle contains no filaments other than the first and second filaments. The actuator is operable to move the plurality of filaments relative to the hub, the elongate member, and the tip between the retracted position and a deployed position. In the deployed position, the plurality of filaments extends outwardly and away from the tip. Each filament comprises a distal end that defines a point in the deployed position. Each point is distal to the distal end of the needle. When the plurality of filaments is in the deployed position, the tip comprises an angle of at least 200° about the central longitudinal axis of the elongate member that is free of filaments.

In some embodiments, a method of performing spinal RF neurotomy in a patient comprises moving a tip of a needle to a first position proximate to a target nerve along the spine of the patient, after achieving the first position, advancing a plurality of filaments relative to the tip to a deployed position, and after the advancing step, applying RF energy to the tip and plurality of filaments, wherein said applying generates heat that ablates a portion of the target nerve.

In some embodiments, a method of performing lumbar RF neurotomy on a medial branch nerve in a patient comprises: moving a tip of a needle to a first position between the transverse and superior articular processes of a lumbar vertebra such that an end point of the tip is proximate to a surface of the vertebra; after achieving the first position, advancing a plurality of filaments relative to the tip to a deployed position; and after advancing the plurality of filaments, applying RF energy to the tip and the plurality of filaments. Said applying generates heat that ablates a portion of the medial branch nerve.

In some embodiments, a method of performing sacroiliac joint RF neurotomy in a patient comprises: a. moving a tip of a needle to a first position proximate to a sacrum of the patient; b. advancing a plurality of filaments relative to the tip to a first deployed position; c. applying RF energy to the tip and plurality of filaments, wherein the applying generates heat that ablates a first volume; d. retracting the plurality of filaments; e. with the tip in the first position, rotating the needle about a central longitudinal axis of the needle to re-orient the plurality of filaments; f. re-advancing the plurality of filaments relative to the tip; and g. re-applying RF energy to the tip and plurality of filaments, wherein the re-applying comprises ablating a second volume proximate to the tip, wherein a center of the first volume is offset from a center of the second volume.

In some embodiments, a method of performing thoracic RF neurotomy on a medial branch nerve in a patient comprises: moving a tip of a needle to a first position proximate a superior surface of a transverse process of a thoracic vertebra such that an end point of the tip is proximate to the superior surface; after achieving the first position, advancing a plurality of filaments relative to the tip toward a vertebra immediately superior to the thoracic vertebra to a deployed position; and after advancing the plurality of filaments, applying RF energy to the tip and the plurality of filaments, wherein said applying generates heat that ablates a portion of the medial branch nerve between the thoracic vertebra and the vertebra immediately superior to the thoracic vertebra.

In some embodiments, a method of performing cervical medial branch RF neurotomy on a third occipital nerve of a patient comprises: a. positioning the patient in a prone position; b. targeting a side of the C2/3 Z-joint; c. rotating the head of the patient away from the targeted side; d. locating the lateral aspect of the C2/3 Z-joint; e. moving, after steps a, b, c and d, a tip of a needle over the most lateral aspect of bone of the articular pillar at the juncture of the C2/3 z-joint to a first position contacting bone proximate to the most posterior and lateral aspect of the z-joint complex; f. retracting, after step e, the tip of the needle a predetermined distance from the first position; g. extending, after step f, a plurality of filaments outwardly from the tip and towards the lateral aspect of the C2/3 z-joint such that the plurality of filaments are positioned straddling the lateral joint lucency and posterior to the C2/3 neural foramen; h. verifying, after step g, the position of the tip and filaments by imaging the tip and a surrounding volume; and i. applying, after step h, RF energy to the tip and the plurality of filaments, wherein the applying generates heat that ablates a portion of the third occipital nerve.

For purposes of summarizing the invention and the advantages achieved over the prior art, certain objects and advantages of the invention are described herein. Of course, it is to be understood that not necessarily all such objects or advantages need to be achieved in accordance with any particular embodiment. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

These and other features, aspects, and advantages of the present disclosure are described with reference to the drawings of certain embodiments, which are intended to illustrate certain embodiments and not to limit the invention.

FIG. 2D is a perspective view of another example embodiment of a needle that may be used in an RF neurotomy procedure.

FIG. 3B is a detailed view of the needle tip of FIG. 3A with filaments in a retracted position.

FIG. 3D is a detailed view of another example embodiment of a needle tip with filaments in a fully deployed position.

FIG. 3E is a detailed view of the needle tip of FIG. 3D with filaments in a retracted position.

FIG. 3G is a detailed view of yet another example embodiment of a needle tip with filaments in a deployed position.

FIGS. 3H and 3I are detailed views of still other example embodiments of a needle tip with filaments in a deployed position.

FIG. 4 is a schematic diagram of an example embodiment of an RF probe assembly.

FIG. 16D is a perspective view of an example embodiment of an elongate member.

FIG. 16F is a cross-sectional view of the needle tip and elongate member of FIG. 16E along the line 16F-16F of FIG. 16E and example embodiments of a filament and an RF probe.

DETAILED DESCRIPTION

Although certain embodiments and examples are described below, those of skill in the art will appreciate that the invention extends beyond the specifically disclosed embodiments and/or uses and obvious modifications and equivalents thereof. Thus, it is intended that the scope of the invention herein disclosed should not be limited by any particular embodiments described below.

In the following description, the invention is set forth in the context of apparatuses and methods for performing RF ablation. More particularly, the systems and methods may be used to perform RF neurotomy to ablate portions of target nerves. Even more particularly, the systems and methods may be used to perform spinal RF neurotomy to ablate portions of target nerves along the spine of a patient to relieve pain. For example, embodiments of methods and apparatuses described herein relate to lumbar RF neurotomy to denervate a facet joint between the L4 and L5 lumbar vertebrae. Denervation may be achieved by application of RF energy to a portion of a medial branch nerve to ablate or cauterize a portion of the nerve, thus interrupting the ability of the nerve to transmit signals to the central nervous system. In another example, embodiments described herein relate to sacroiliac joint RF neurotomy.

Figure 1:
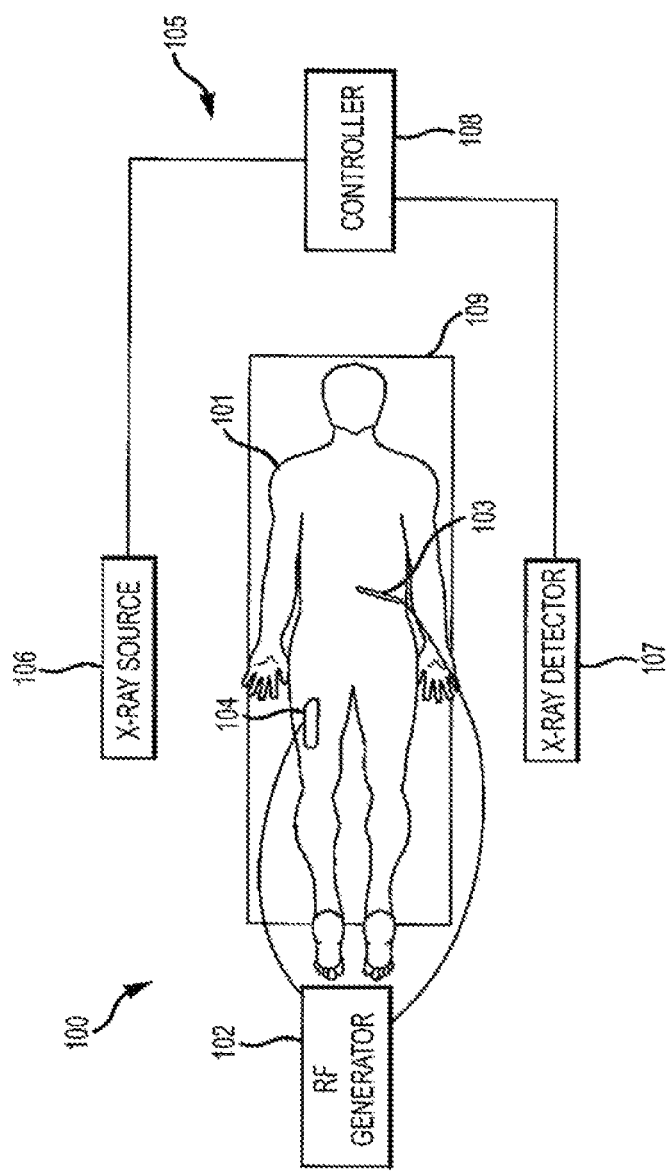
FIG. 1 is a schematic diagram of an RF neurotomy system being used to perform RF neurotomy on a patient.

FIG. 1 illustrates an example embodiment of a system 100 for performing RF neurotomy on a patient 101. The patient 101 may be positioned face down on a table or surface 109 to allow access along the spine of the patient 101. Other patient orientations are also possible depending on the procedure. The table 109 may comprise radiolucent materials substantially transparent to x-rays, such as carbon fiber.

The system 100 may include an RF generator 102 capable of generating an RF energy signal sufficient to ablate target tissue (e.g.: cause lesions in targeted volumes; cauterize targeted portions of target nerves). The RF generator 102 may, for example, be capable of delivering RF energy between about 1 W and about 200 W and between about 460,000 Hz and about 500,000 Hz. A needle 103 capable of conducting (e.g., transmitting or directing) RF energy may be interconnected to the RF generator 102 and may be used to deliver an RF energy signal to a specific site within the patient 101. In some embodiments in which the needle 103 is a monopolar device, a return electrode pad 104 may be attached to the patient 101 to complete a circuit from the RF generator 102, through the needle 103, through a portion of the patient 101, through the return electrode pad 104, and back to the RF generator 102. In some embodiments comprising a bipolar arrangement, the needle 103 may comprise at least one supply electrode and at least one return electrode to define the circuit.

The RF generator 102 may be operable to control the RF energy emanating from the needle 103 in a closed-loop fashion. For example, the needle 103 and/or an RF probe in the needle 103 may include a temperature measurement device, such as a thermocouple, configured to measure temperature at the target tissue. Data may also be available from the RF generator 102, such as power level and/or impedance, which may also be used for closed-loop control of the needle 103. For example, upon detection of a temperature, a parameter (e.g., frequency, wattage, application duration) of the RF generator 102 may be automatically adjusted.

FIG. 4 illustrates an example RF probe assembly 400 compatible with the needle 103. The RF probe assembly 400 includes an RF probe 401 that may be inserted into a patient (e.g., through the needle 103) and may direct RF energy to the target tissue. In some embodiments, the RF probe 401 may be in electrical communication with the needle 103 to direct RF energy to the target tissue, but is not inserted into the patient. The RF probe 401 may include a thermocouple operable to measure temperature at a distal end 402 of the RF probe 401. The RF probe assembly 400 may include a connector 403 and a cable 404 configured to connect the RF probe 401 to an RF generator (e.g., the RF generator 102).

Returning to FIG. 1, the system 100 optionally includes an imaging system 105 capable of producing internal images of the patient 101 and the needle 103, for example to facilitate navigation of the needle 103 during a procedure. The system 100 may further include a display device for displaying the generated images to a user performing the procedure. In some embodiments, the imaging system 105 comprises a fluoroscope capable of generating real-time two dimensional images of the needle 103 and internal structures of the patient 101. In certain such embodiments, the imaging system includes an X-ray source 106, an X-ray detector 107, and a controller 108 in electrical communication with the X-ray source 106 and/or the X-ray detector 107. The X-ray source 106 and X-ray detector 107 may be mounted on a movable structure (e.g., a C-arm), to facilitate capturing a variety of images of the patient 101 (e.g., at various angles or projection views). Other imaging systems 105 are also possible (e.g., a computed tomography (CT) scanner).

Figure 2A:
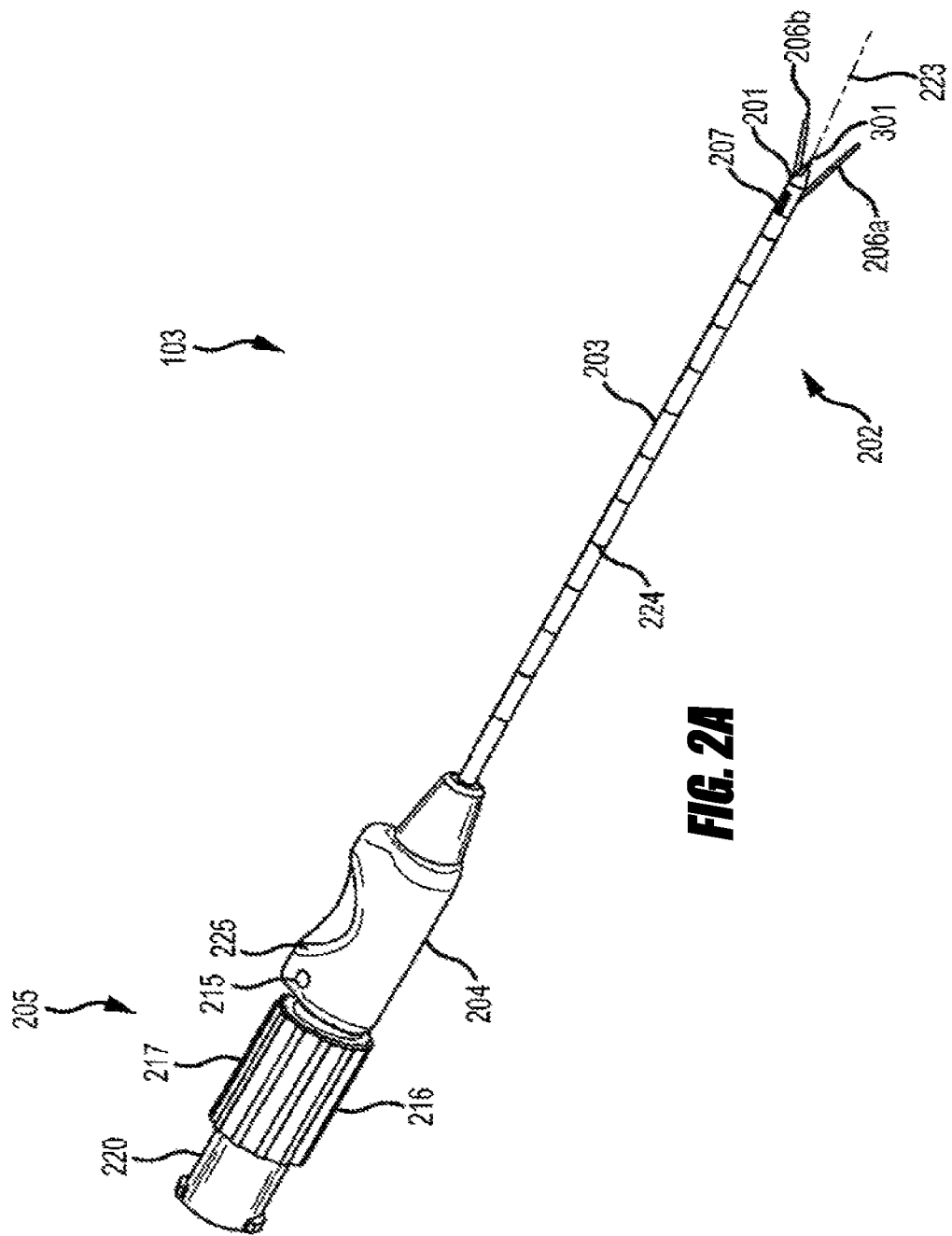
FIG. 2A is a perspective view of an example embodiment of a needle that may be used in an RF neurotomy procedure.

FIG. 2A illustrates an example embodiment of a needle 103 that may be used in the system 100 for performing RF neurotomy. The needle 103 includes a tip 201 that tapers to a point 301 capable of piercing the skin of a patient. In some embodiments, the tip point tapers to a point substantially at the center of the tip 201 (e.g., a "pencil-point" tip). In some embodiments, the tip point tapers to a point substantially at one side of the tip 201 (e.g., a "cutting" or "beveled" or "lancet" or "Quincke" tip). The needle 103 further includes an elongate member 203 connected to the tip 201 at a distal end 202 of the needle 103 and connected to a hub 204 at a proximal end 205 of the needle 103. The needle 103 includes a longitudinal axis 223 along the center of the elongate member 203.

FIG. 2D illustrates another example embodiment of a needle 103 that may be used in the system 100 for performing RF neurotomy. The needle 103 includes a tip 211 that tapers to a point 301 capable of piercing the skin of a patient. In some embodiments, the tip point tapers to a point substantially at the center of the tip 211 (e.g., a "pencil-point" tip). In some embodiments, the tip point tapers to a point substantially at one side of the tip 211 (e.g., a "cutting" or "beveled" or "lancet" or "Quincke" tip). The needle 103 further includes an elongate member 203 connected to the tip 211 at a distal end 202 of the needle 103 and connected to a hub 204 at a proximal end 205 of the needle 103. The needle 103 includes a longitudinal axis 223 along the center of the elongate member 203.

The needle 103 may include a self-contained mechanical mechanism, in the form of deployable filaments 206a, 206b, operable to expand the volume of effective RF energy delivery as compared to known single-electrode RF probes. The filaments 206a, 206b may be at least partially in the elongate member 203 and may be operable to emerge through one or more apertures of the needle 103 proximate to the distal end 202 of the needle 103. In some embodiments, the needle 103 includes a single filament or three or more filaments. The filaments 206a, 206b allow contraction/expansion, offsetting, and/or contouring of the effective RF energy delivery over a selected area of anatomy to adjust lesion geometry produced using the needle 103 to match a desired target volume (e.g., spherical, hemispherical, planar, spheroid, kidney-shaped, catcher's mitt-shaped, oblong, snowman-shaped, etc.). The filaments 206a, 206b may be deployable and/or retractable by moving (e.g., rotating) an actuator 216 relative to the hub 204.

As will be further described, the needle 103 may further include a tube 207 that includes a lumen 222 therethrough. The lumen 222 may be used to transport fluids to and/or from the target volume. The lumen 222 may also accept the RF probe 401 for delivery of RF energy to the target volume. The lumen 222 may also accept a dummy or temporary probe, for example to occlude the fluid port 210 during insertion. In some embodiments, the RF probe 401 is integrated with the needle 103. In certain such embodiments, the tube 207 need not be present for RF energy delivery, although it may be included to facilitate fluid delivery. In some embodiments, the filaments 206a, 206b include lumens therethrough for the transportation of fluid to and/or from the target volume. In some embodiments, the filaments 206a, 206b do not include lumens therethrough (e.g., being solid). The filaments 206a, 206b may function as thermocouples.

As RF energy penetrates biological tissue, protein and water molecules oscillate in response to the RF current and the tissue adjacent to the RF electrode is heated. As the tissue heats and coagulates, the biophysical properties of the tissue change. These tissue changes limit penetration of the RF energy beyond a leading edge defined by the shape and size of an active needle tip. Accordingly, the size of a radiofrequency lesion using conventional single needle technology is practically limited after achievement of a certain temperature delivered for a certain time.

A needle 103 with deployable filaments 206a, 206b can overcome this obstacle and expand the effective area of RF energy delivery by providing multiple locations (e.g., the tip 201, 211 the filament 206a, and/or the filament 206b) from which the RF energy emanates. The use of multiple filaments 206a, 206b provides additional conduits for RF energy, creating a multiple electrode RF field effect. The size, shape, and location of a lesion created with the needle 103 may be at least partially determined by, for example, the quantity, angle, length, location, and/or orientation of the filaments and RF energy parameters such as wattage, frequency, and/or application duration, one or all of which may be beneficially modified to suit a specific anatomical application by changing various aspects of the filaments as discussed below.

Where it is desired to create a lesion offset from the central longitudinal axis 223, the lesion may be offset in a desired direction from the central longitudinal axis 223 by rotationally orienting the needle 103. The needle 103 may be used to create a lesion offset from the central longitudinal axis 223 in a first direction. The filaments 206a, 206b may be retracted (e.g., after creating a first lesion), the needle 103 rotated, and the filaments 206a, 206b re-deployed to create a lesion offset from the central longitudinal axis 223 in a second direction (e.g., to create a second lesion).

Figure 3A:
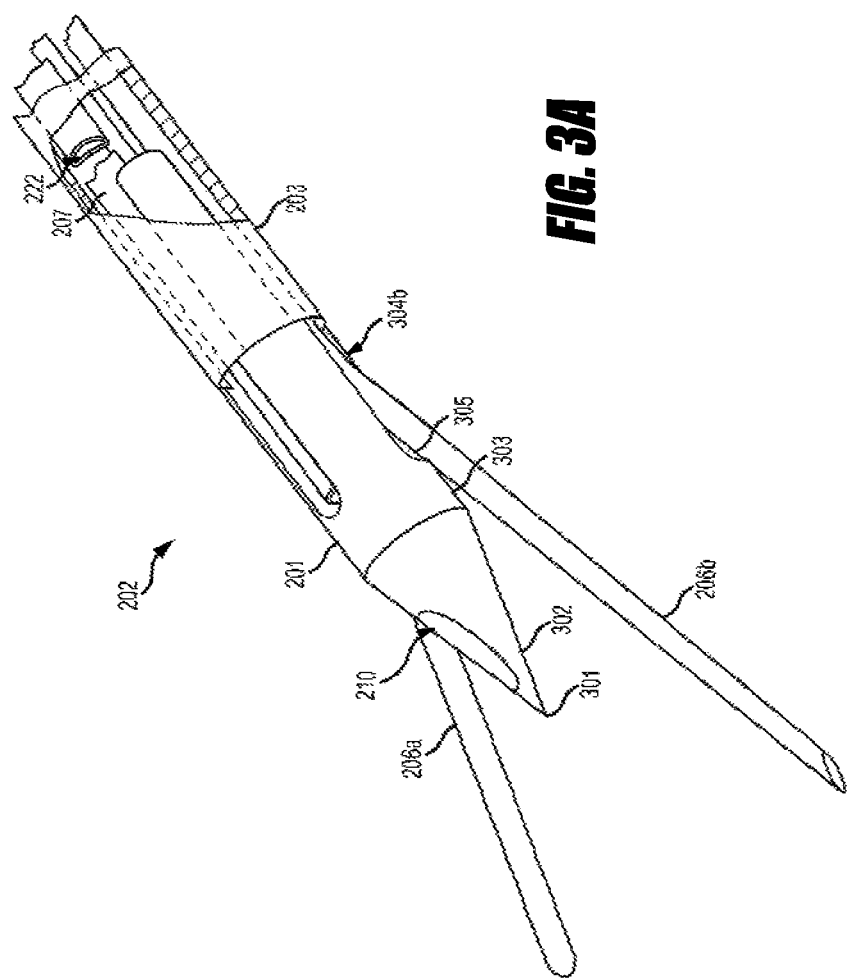
FIG. 3A is a detailed view of an example embodiment of a needle tip with filaments in a fully deployed position.

FIGS. 3A and 3B are detailed views of an example embodiment of a distal end 202 of a needle 103 that includes a tip 201. The tip 201 may include a sharpened point 301 (e.g., tapering to a point substantially at the center of the tip 201, a pencil-point tip) for piercing the skin of a patient and facilitating advancement through tissue. The tip 201 may include a tapered portion 302 that transitions the tip 201 from the point 301 to a body portion 303. The body portion 303 is the portion of the tip 201 that is proximal to the tapered portion 302. The body portion 303 may be cylindrical as illustrated, or may be other appropriate shapes. The body portion 303 may have a cross-section that coincides with (e.g., is coaxial with) the cross section of the elongate member 203.

Figure 16A:
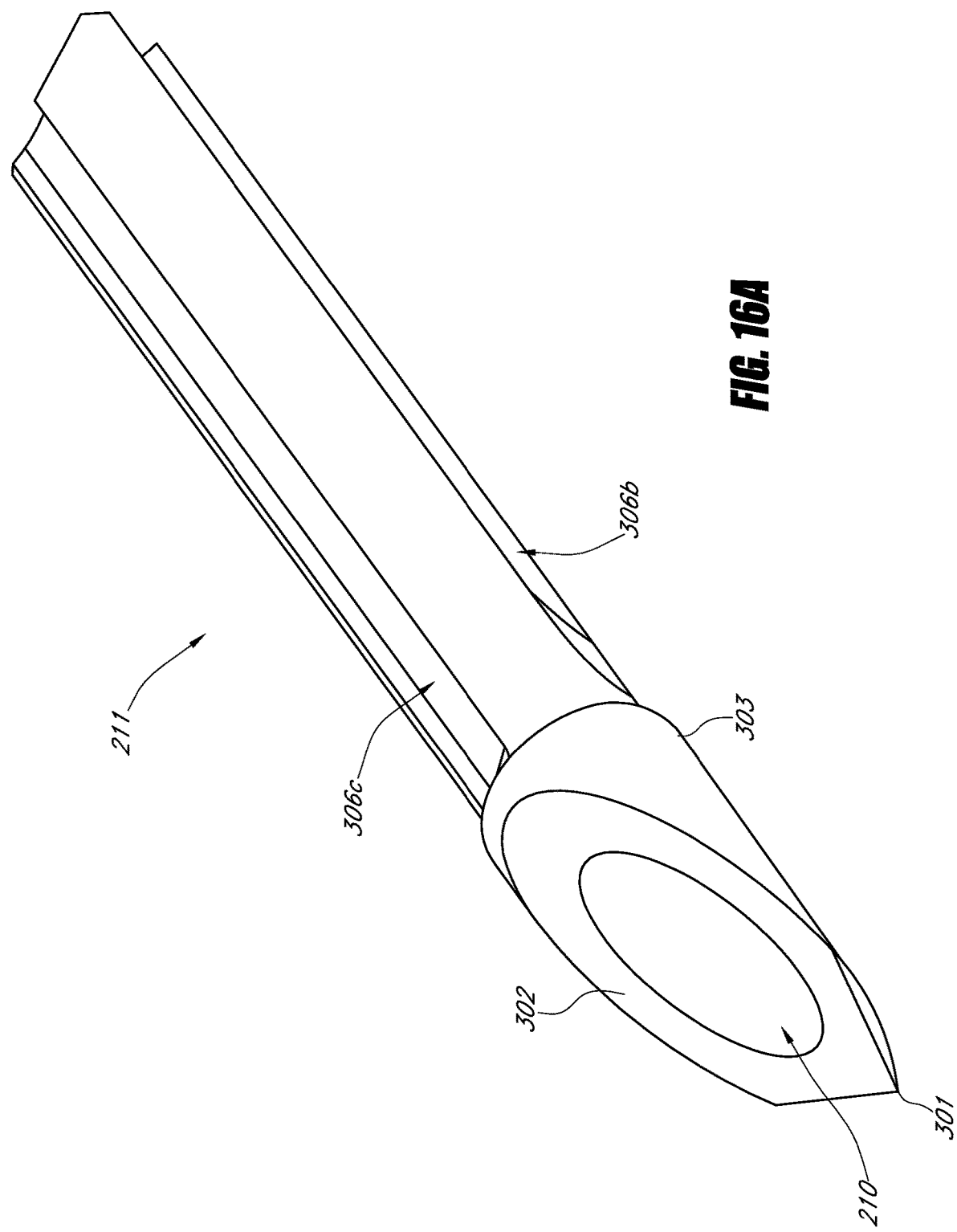
FIG. 16A is a perspective view of an example embodiment of a needle tip.

FIGS. 3D and 3E are detailed views of another example embodiment of a distal end 202 of a needle 103 that includes a tip 211. The tip 211 may include a sharpened point 301 (e.g., tapering to a point substantially at one side of the tip 201, a cutting or beveled or lancet or Quincke tip) for piercing the skin of a patient and facilitating advancement through tissue. The tip 211 may include a tapered portion 302 that transitions the tip 211 from the point 301 to a body portion 303. The body portion 303 is the portion of the tip 201 that is proximal to the tapered portion 302. The body portion 303 may be cylindrical as illustrated, or may be other appropriate shapes (e.g., as illustrated in FIG. 16A). The body portion 303 may have a cross-section that coincides with (e.g., is coaxial with) the cross section of the elongate member 203. In some embodiments, the tip 211 has a bevel angle between about 10° and about 45°, between about 15° and about 35°, between about 20° and about 30° (e.g., about 25°), combinations thereof, and the like. Other bevel angles are also possible. In some embodiments, the point 301 has an angle between about 40° and about 120°, between about 70° and about 90°, between about 75° and about 85° (e.g., about 79°), combinations thereof, and the like. Other angles are also possible.

The tip 201, 211, or a non-insulated portion thereof, may act as an RF energy delivery element. The tip 201, 211 may comprise (e.g., be made from) a conductive material such as, for example, stainless steel (e.g., 300 Series Stainless Steel). The tip 201, 211 may be at least partially coated (e.g., with an insulator). The material of the tip 201, 211 and the material of the optional coating may be selected, for example, to act as an insulator, improve radiopacity, improve and/or alter RF energy conduction, improve lubricity, and/or reduce tissue adhesion.

The tip 201, 211 includes a first filament port or slot 304a (not visible in the views of FIGS. 3A, 3B, 3D, and 3E) and a second filament port or slot 304b. The geometry of the filament slots 304a, 304b may be selected to allow filaments 206a, 206b to be adequately retracted (e.g., such that the filaments 206a, 206b are in a cross-sectional envelope of the body portion 303 of the tip 201, 211, as shown in FIG. 3F) while the needle 103 is inserted into the body, so that the filaments 206a, 206b do not cause any unintended damage to the patient. Such positioning of the filament slots 304a, 304b avoids having filament exit features on the tapered portion 302 and thus avoids potential coring that could be caused by such positioning.

Figure 10:
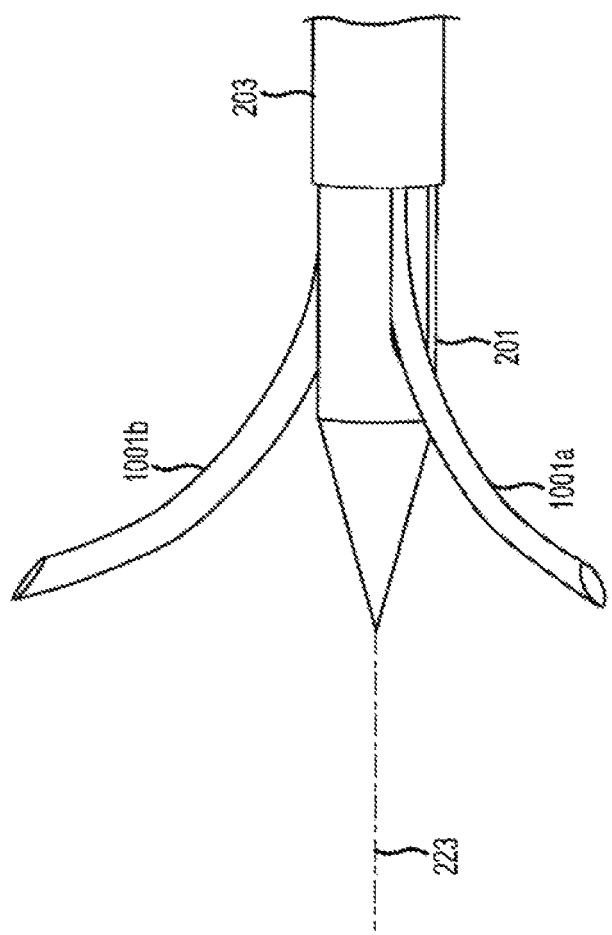
FIG. 10 is a side view of another example embodiment of a needle tip.

The internal geometry of the filament slots 304a, 304b may be designed such that the filaments 206a, 206b may be easily retracted and advanced. For example, the internal geometry of the filament slots 304a, 304b may include a transition region 305 that meets the outer surface of the body portion 303 at an angle of about 30°. The transition region 305 may, for example, be curved and/or planar. Advancement of filaments 206a, 206b without a pre-set bias (e.g., substantially straight) relative to the filament slots 304a, 304b can causes the filaments 206a, 206b to be deflected outwardly as the filaments 206a, 206b move distally along the transition region 305. Depending on the positioning of the transition region 305 relative to where the filaments 206a, 206b are confined (e.g., in the needle 103 of FIG. 3A, the filaments 206a, 206b are confined to only longitudinal movement where they enter into the elongate member 203) and on the mechanical properties of the filaments 206a, 206b, various deployment angles of the filaments 206a, 206b relative to the central longitudinal axis 223 may be achieved. Generally, the portions of the filaments 206a, 206b that extend outwardly away from the filament slots 304a, 304b may be unrestrained and thus may take any appropriate form. For example, where there is no pre-set bias, the portions of the filaments that extend outwardly away from the filament slots 304a, 304b (and therefore from the tip) may be substantially straight, such as shown in FIGS. 2A, 3A, 3C, 3D, 6, 11A-11C, and 14. For another example, when there is a pre-set bias, the portions of the filaments that extend outwardly away from the filament slots may take any appropriate shape, such as, for example, curved as shown in FIG. 10.

The radial orientation of the filament slots 304a, 304b may be selected such that a center point between the filament slots 304a, 304b does not coincide (e.g., is not coaxial with) with the central longitudinal axis 223. For example, as shown in FIGS. 2A, 3A, 3B, 3D, and 3E, the filament slots 304a, 304b may be positioned such that they are about 120° apart about the circumference of the tip 201, 211. Other filament slot configurations may be configured to achieve the filament placements discussed below. For example, the filament slots 304a, 304b may be between about 45° and about 180° apart about the circumference of the tip 201, 211, between about 90° and about 180° apart about the circumference of the tip 201, 211, between about 90° and about 150° apart about the circumference of the tip 201, 211, combinations thereof, and the like. Other angles are also possible. These configurations may be achieved by varying, for example, the quantity of filament slots, the placement of filament slots about the circumference of the tip 201, 211, and/or the placement of filament slots along the center longitudinal axis 223 to achieve the filament placements discussed below.

As noted herein, and illustrated in FIGS. 3A and 3B, the needle 103 may comprise a tube 207 that includes a lumen 222 therethrough. The lumen 222 may be employed to accept the RF probe 401 for delivery of RF energy, for the transport of fluids, and/or for occluding a fluid port 210. The tip 201, 211 may include a fluid port 210 that may be in fluid communication with the lumen 222 via a channel through the tip 201, 211. In certain embodiments, the lumen 222 is a dual-purpose lumen that can allow injection of fluids and that can receive the distal end 402 of the RF probe 401 to deliver RF energy to the tip 201, 211, the filament 206a, and/or the filament 206b. In some embodiments, the fluid port 210 is longitudinally spaced from the tip 301 (e.g., by between about 1 mm and about 3 mm). The fluid port 210 may be centrally located (e.g., as illustrated in FIG. 3D) or it may be located offset from the center longitudinal axis 223 (e.g., as shown in FIGS. 2A and 3A). The fluid port 210 may be used to transfer fluid between the region of the tip 201, 211 and the proximal end 205 of the needle 103. For example, during an RF neurotomy procedure, an anesthetic and/or an image enhancing dye may be introduced into the region of tissue around the tip 201, 211 through the fluid port 210. In some embodiments, the fluid port 210 is located along the tapered portion 302 of the tip 201, 211 (e.g., as illustrated in FIGS. 3A and 3D). In some embodiments, the fluid port 210 is located along the body portion 303 of the tip 201, 211.

FIG. 16A is a perspective view of an example embodiment of the needle tip 211. In some embodiments, the needle 103 does not comprise a tube 207, but the elongate member 203 comprises a lumen 308 therethrough and the tip 211 comprises a lumen 306c therethrough. The lumen 308 and the lumen 306c may be employed to accept the RF probe 401 for delivery of RF energy, for the transport of fluids, and or for occluding the fluid port 210. In certain embodiments, the lumen 308 and the lumen 306c are dual-purpose lumens that can allow injection of fluids and that can receive the distal end 402 of the RF probe 401 to deliver RF energy to the tip 211, the filament 206a, and/or the filament 206b. The filament lumens 306a, 306b may also allow liquid transfer from a proximal end of the needle to the filament ports 304a, 304b.

In some embodiments, the filament lumens 306a, 306b are sized to inhibit buckling and/or bending of the filaments in the tip 211. In some embodiments, the elongate member 203 may also include filament lumens (e.g., comprising tubes in the elongate member 203). In some embodiments, filament lumens in the elongate member 203 may be formed by an inner member (not shown) extending at least part of the length of the elongate member 203. For example, a transverse cross-section of the inner member may have the same cross-section as the portion of the tip 211 illustrated in FIG. 3F, including channels in which the filaments may lie and a lumen for passing fluid, an RF probe 401, and/or a dummy probe.

Figure 16B:
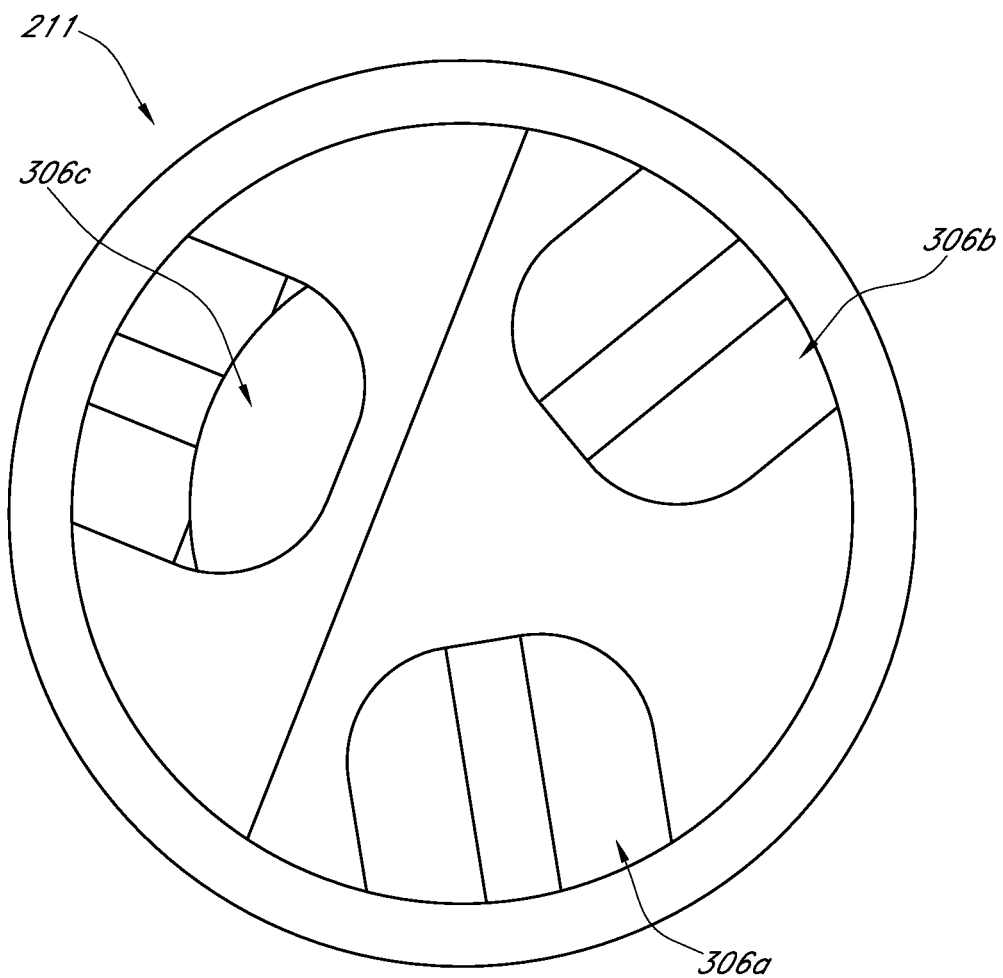
FIG. 16B is a back elevational view of the needle tip of FIG. 16A.
Figure 16C:
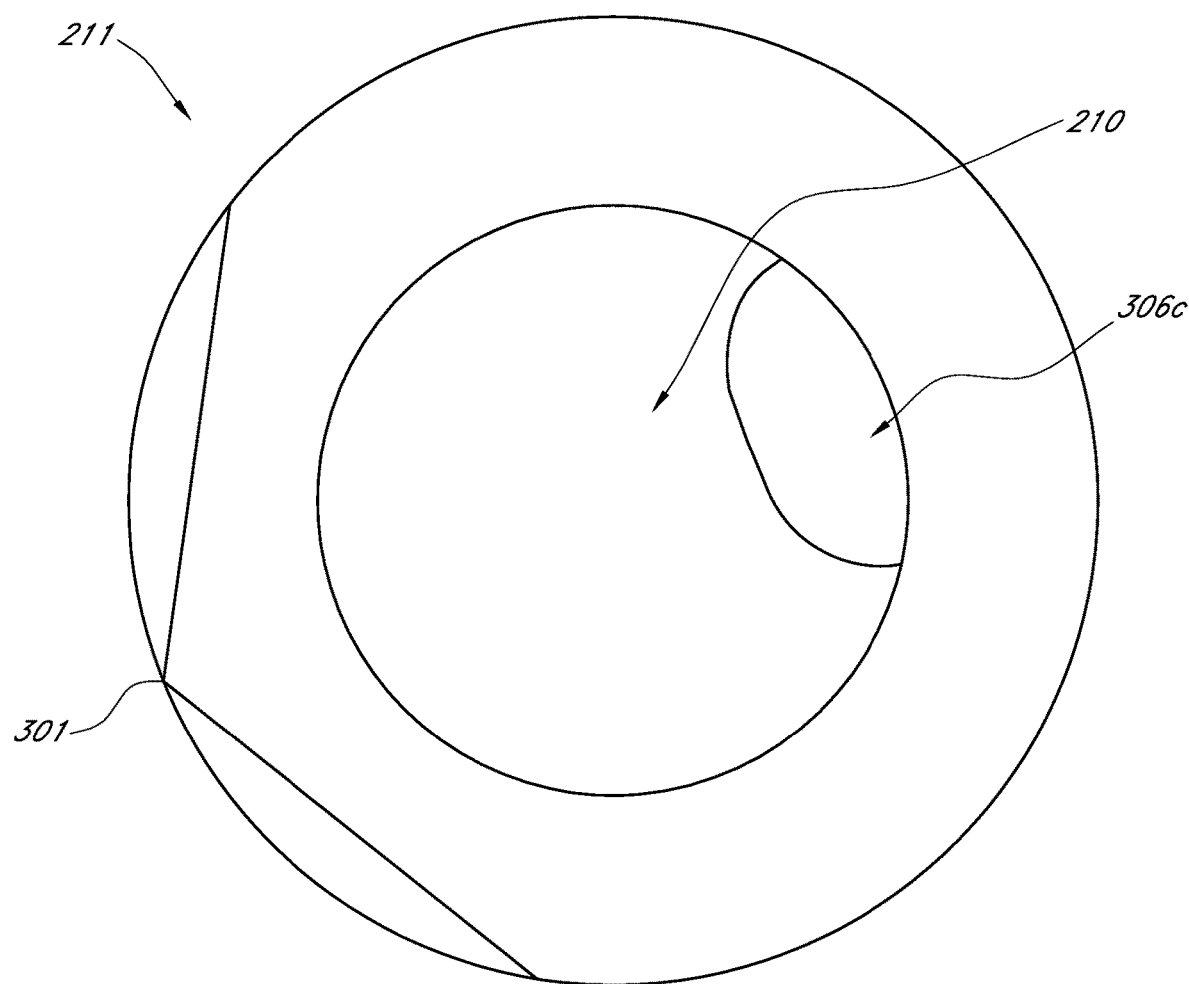
FIG. 16C is a front elevational view of the needle tip of FIG. 16A.

FIG. 16B is a back elevational view of the needle tip 211 of FIG. 16A. FIG. 16C is a front elevational view of the needle tip 211 of FIG. 16A. The needle tip 211 comprises a filament lumen 306a in fluid communication with and terminating at the filament slot 304a, a filament lumen 306b in fluid communication with and terminating at the filament slot 304b, and the lumen 306c. In some embodiments, the lumens 306a, 306b are spaced by about 120° along the circumference of the tip 211. Other angles are also possible. In some embodiments, the lumen 306c is spaced from each of the lumens 306a, 306b by about 120° along the circumference of the tip 211. Other angles are also possible. Referring again to FIG. 3F, the filament 206a may be in the filament lumen 306a and the filament 206b may be in the filament lumen 306b. The lumen 306c is in fluid communication with the fluid port 210. In some embodiments, the proximal end of the tip 211 includes a tapered surface, as shown in FIG. 16A. When filaments 206a, 206b are in the filament lumens 306a, 306b, the tapered surface may help to guide insertion of an RF probe 401 into the lumen 306c. In some embodiments, the tapered surface has an angle normal to the tip 211 between about 15° and about 75°, between about 30° and about 60°, between about 40° and about 50° (e.g., about 45°), combinations thereof, and the like. Other angles are also possible.

Figure 16E:
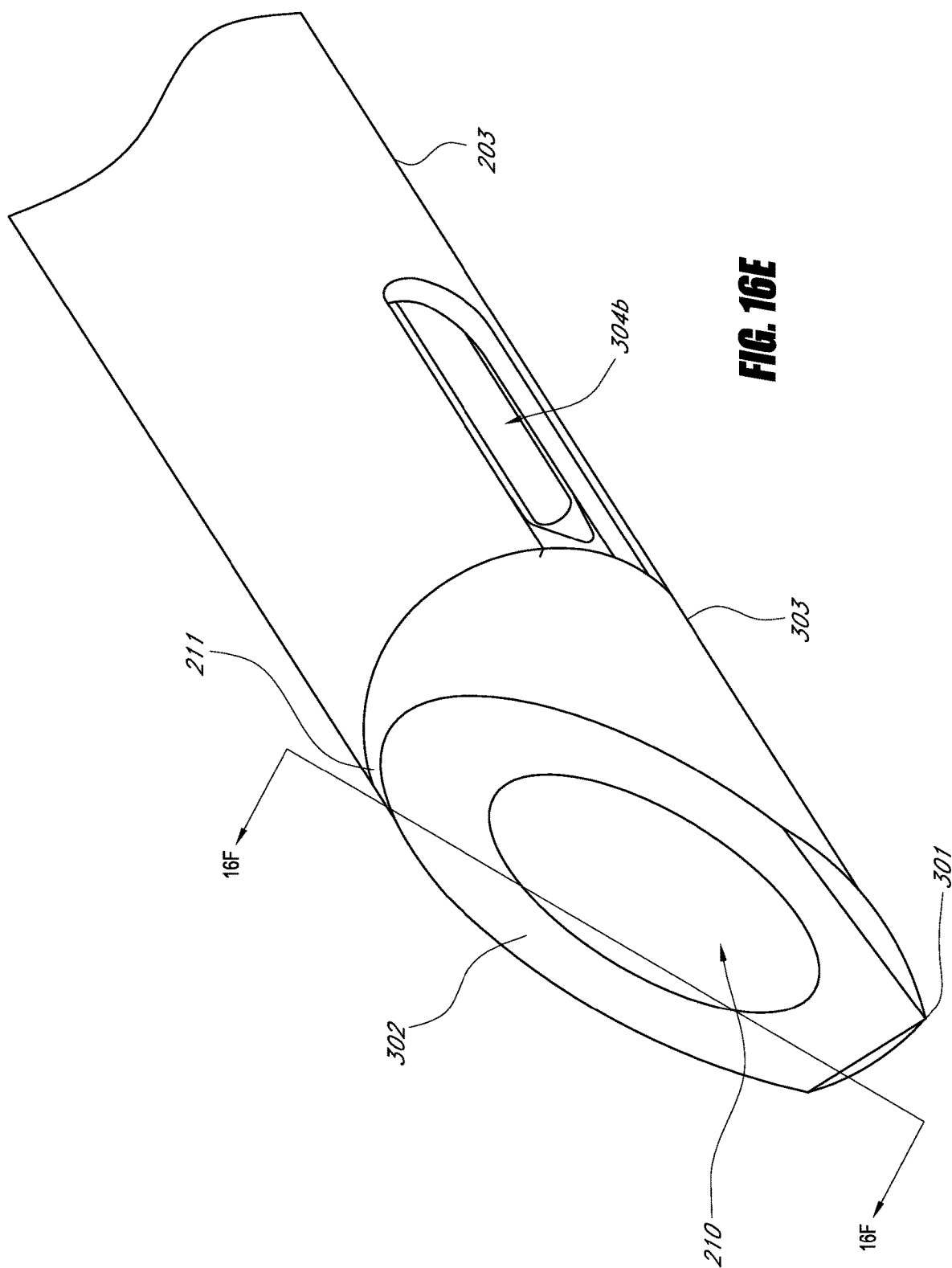
FIG. 16E is a perspective view of the needle tip of FIG. 16A and the elongate member of FIG. 16D.

FIG. 16D is a perspective view of an example embodiment of an elongate member 203. The elongate member 203 includes the lumen 308, the filament slot 304a, and the filament slot 304b. In some embodiments, the filament slots 304a, 304b are spaced by about 120° along the circumference of the elongate member 203. FIG. 16E is a perspective view of the needle tip 211 of FIG. 16A and the elongate member 203 of FIG. 16D. As described herein, the elongate member 203 may be coupled to the tip 211 by adhering with conductive epoxy, welding, soldering, combinations thereof, and the like. A proximal portion of the tip 211 can be inserted into the lumen 308 of the elongate member 203. The filament slot 304b of the elongate member 203 is substantially aligned with the lumen 306b of the tip 211, allowing the filament 206b to be deployed out of the lumen 306b. Although not illustrated, the filament slot 304a of the elongate member 203 is substantially aligned with the lumen 306a of the tip 211, allowing the filament 206a to be deployed out of the lumen 306a. In some embodiments, each of the filament slots 304a, 304b has a length between about 0.025 inches and about 0.2 inches (approx. between about 0.6 mm and about 3 mm), between about 0.05 inches and about 0.15 inches (approx. between about 1.3 mm and about 3.8 mm), between about 0.075 inches and about 0.125 inches (approx. between about 1.9 mm and about 3.2 mm) (e.g., about 0.105 inches (approx. about 2.7 mm)), combinations thereof, and the like. Other lengths are also possible. In some embodiments, each of the filament slots 304a, 304b has a width between about 0.01 inches and about 0.4 inches (approx. between about 0.25 mm and about 10 mm), between about 0.02 inches and about 0.03 inches (approx. between about 0.5 mm and about 0.76 mm), between about 0.015 inches and about 0.025 inches (approx. between about 0.38 mm and about 0.64 mm) (e.g., about 0.02 inches (approx. about 0.5 mm)), combinations thereof, and the like. Other widths are also possible. In some embodiments, the each of the transition regions 305 has a length between about 0.02 inches and about 0.2 inches (approx. between about 0.5 mm and about 5 mm), between about 0.05 inches and about 0.15 inches (approx. between about 1.3 mm and about 3.8 mm), between about 0.075 inches and about 0.125 inches (approx. between about 1.9 mm and about 3.2 mm) (e.g., about 0.104 inches (approx. about 2.6 mm)), combinations thereof, and the like. Other lengths are also possible. In some embodiments in which the transition regions include curved surfaces, the each of the transition regions 305 has a radius of curvature between about 0.01 inches and about 0.4 inches (approx. between about 0.25 mm and about 10 mm), between about 0.15 inches and about 0.35 inches (approx. between about 3.8 mm and about 8.9 mm), between about 0.2 inches and about 0.3 inches (approx. between about 5 mm and about 7.6 mm) (e.g., about 0.25 inches (approx. about 6.4 mm)), combinations thereof, and the like. Other radii of curvature are also possible. Certain combinations of dimensions of the transition regions 305 and filaments slots 304a, 304b described herein may cause deployment of the filaments 206a, 206b at desired angles (e.g., about 30°).

The lumen 308 is not visible in FIG. 16E because the elongate member 203 covers the lumen 308. Covering the lumen 308 causes fluid inserted into the lumen 308 to exit the fluid port 210, and possibly the filament slots 304a, 304b. In some embodiments, for example as illustrated in FIGS. 3A and 3B, the elongate member 203 may also include a slot proximate to the tube 207. In certain such embodiments, the tube 207 may extend distal to the slot and substantially all fluid inserted into the lumen 222 exits the fluid port 210.

In the embodiment illustrated in FIG. 16E, the body portion 303 of the tip 211 and the elongate member 203, excluding the sleeve 307, have substantially equal diameters, for example to provide a smooth transition between the tip 211 and the elongate member 203. In some embodiments, the elongate member 203 has an inner diameter between about 0.01 inches and about 0.04 inches (approx. between about 0.25 mm and about 1 mm), between about 0.015 inches and about 0.035 inches (approx. between about 0.38 mm and about 0.89 mm), between about 0.02 inches and about 0.03 inches (approx. between about 0.5 mm and about 0.76 mm) (e.g., about 0.025 inches (approx. about 0.64 mm)), combinations thereof, and the like. Other diameters are also possible. In some embodiments, the elongate member 203 has an outer diameter between about 0.01 inches and about 0.05 inches (approx. between about 0.25 mm and about 1.3 mm), between about 0.02 inches and about 0.04 inches (approx. between about 0.5 mm and about 1 mm), between about 0.025 inches and about 0.035 inches (approx. between about 0.64 mm and about 0.89 mm) (e.g., about 0.029 inches (approx. about 0.74 mm)), combinations thereof, and the like. Other diameters are also possible. In some embodiments, the proximal portion of the tip has an outer diameter between about 0.01 inches and about 0.04 inches (approx. between about 0.25 mm and about 1 mm), between about 0.015 inches and about 0.035 inches (approx. between about 0.38 mm and about 0.89 mm), between about 0.02 inches and about 0.03 inches (approx. between about 0.5 mm and about 0.76 mm) (e.g., about 0.025 inches (approx. about 0.64 mm)), combinations thereof, and the like. Other diameters are also possible. In some embodiments, the tip 211 has an outer diameter between about 0.01 inches and about 0.05 inches (approx. between about 0.25 mm and about 1.3 mm), between about 0.02 inches and about 0.04 inches (approx. between about 0.5 mm and about 1 mm), between about 0.025 inches and about 0.035 inches (approx. between about 0.64 mm and about 0.89 mm) (e.g., about 0.029 inches (approx. about 0.74 mm)), combinations thereof, and the like. Other diameters are also possible.

FIG. 16F is a cross-sectional view of the needle tip 211 and the elongate member 203 along the line 16F-16F of FIG. 16E. FIG. 16F also illustrates an example embodiment of a filament 206a in the lumen 308 and the lumen 306a, then exiting via the filament slot 304a, and an RF probe 401 in the lumen 308. In some embodiments, the elongate member 203 and the tip each 211 comprise (e.g., are each made from) a conductive material (e.g., 300 Series Stainless Steel), and can conduct electrical signals from the RF probe 401 to the tip 211 and the filaments 206a, 206b (e.g., due to physical contact of conductive components) to form a monopolar electrode. In some embodiments, the RF probe 401, the filaments 206a, 206b, the tip 211, and/or the elongate member 203 may include features configured to increase physical contact between the components. The cross-sectional view shows the lumen 308 in fluid communication with the lumen 306c and the fluid port 210.

Figure 16G:
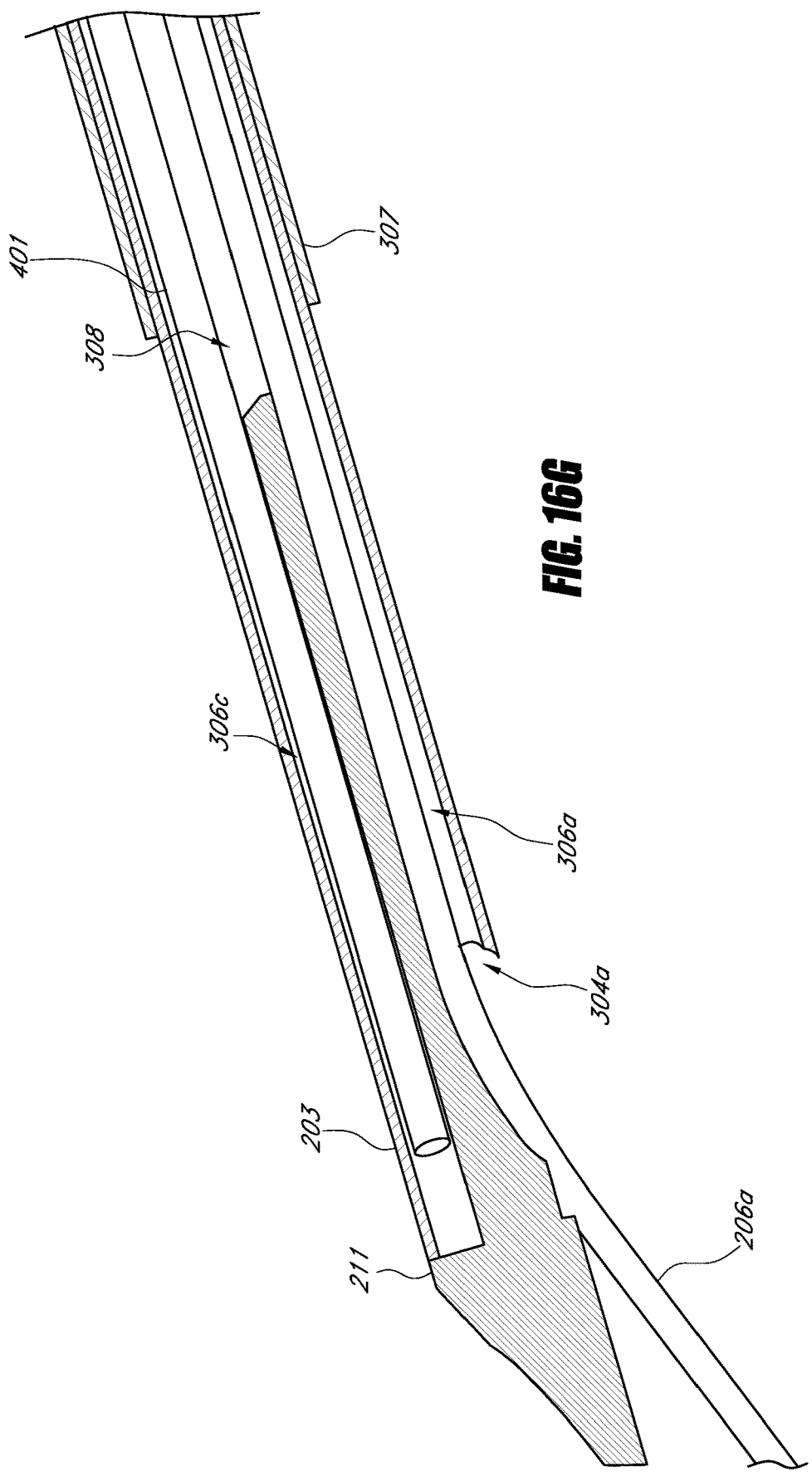
FIG. 16G is a cross-sectional view of another example embodiment of a needle tip and elongate member and example embodiments of a filament and an RF probe.

FIG. 16G is another cross-sectional view of an example embodiment of a needle tip 211 and the elongate member 203 along a line similar to the line 16F-16F in FIG. 16E. The tip 211 in FIG. 16G does not include a fluid port 210, but fluid can permeate out of the filament slots 304a, 304b because the filament slots are in fluid communication with the lumen 308. In some embodiments, the tip 211 includes a lumen 306c, for example to assure placement of or contact with the probe 401 (e.g., as illustrated in FIG. 16G). In some embodiments, the tip 211 does not include a lumen 306c, for example to reduce manufacturing costs if the lumen 306c is cut from a solid tip stem.

As may be appreciated, the channel through the tip 201, 211 may be sized to accommodate a tip of the RF probe 401 that may be inserted into the needle 103. The channel may be sized such that RF energy from the inserted RF probe 401 is satisfactorily communicated from the RF probe 401 to the tip 201, 211, the filament 206a, and/or the filament 206b.

Figure 3C:
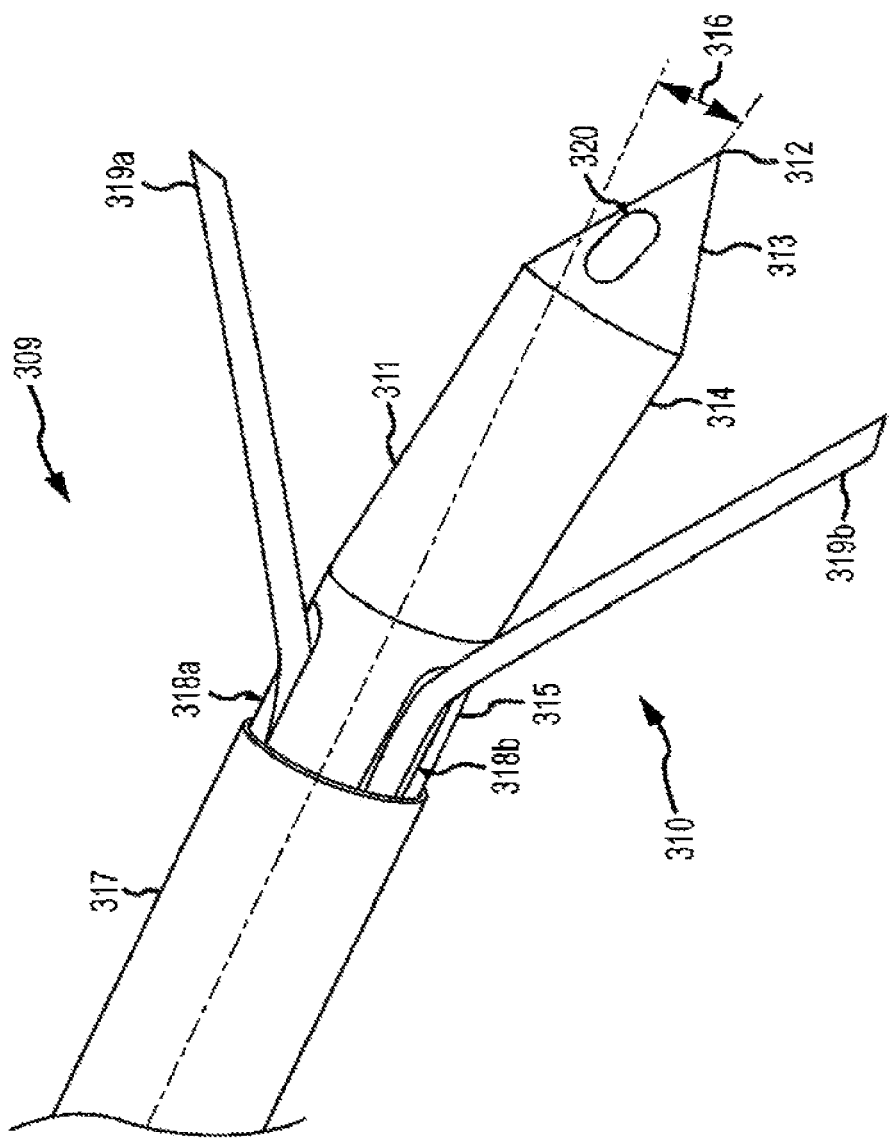
FIG. 3C is a detailed view of another example embodiment of a needle tip with filaments in a deployed position.
Figure 3F:
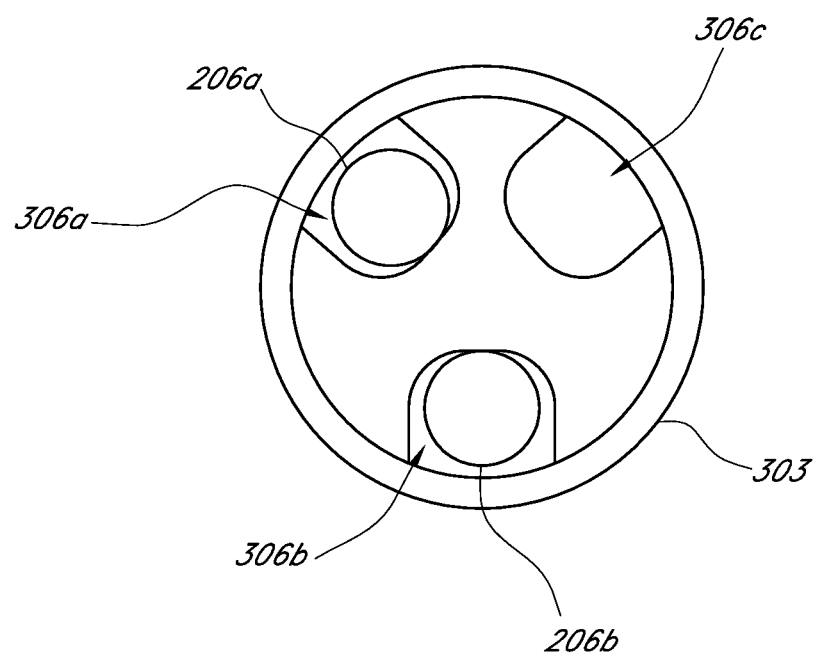
FIG. 3F is a cross-sectional view of the needle tip of FIG. 3D with filaments in a retracted position.

FIGS. 3C and 3G are each a detailed view of the distal end 310 of a needle 309 that is an alternate embodiment of the needle 103. The distal end 310 includes a tip 311, 321 that may include a sharpened point 312 for piercing the skin of a patient and facilitating advancement through tissue. The tip 311, 321 may include a tapered portion 313 that transitions the tip 311, 321 from the point 312 to a first body portion 314. The first body portion 314 may be connected to a second body portion 315 at an angle 316. In some embodiments, the angle 316 is about 15°. Other angles 316 are also possible. For example, the angle 316 may be between about 5° and about 90°, between about 10° and about 60°, between about 10° and about 45°, between about 10° and about 20°, combinations thereof, and the like. Other angles are also possible. The second body portion 315 may be aligned with an elongate member 317. The elongate member 317 may be similarly configured as the elongate member 203 of FIGS. 3A, 3B, 3C, and 3D. The angle 316 between the first body portion 314 and the second body portion 315 may aid the user in navigating the needle 309 to a desired position. For example, by rotating the needle 309 such that the first body portion 314 is pointing in a desired direction, subsequent advancement of the needle 309 may result in the needle 309 following a non-straight path biased toward the desired direction.

The first and second body portions 314, 315 may be cylindrical as illustrated, or they may be of any other appropriate shape. The first and second body portions 314, 315 may have cross-sections that coincide with (e.g., is coaxial with) the cross section of the elongate member 317.

The tip 311, 321, or a non-insulated portion thereof, may act as an RF energy delivery element. The tip 311, 321 may comprise (e.g., be made from) a conductive material such as, for example, stainless steel (e.g., 300 Series Stainless Steel). The tip 311, 321 may be coated (e.g., with an insulator). The material of the tip 311, 321 and the material of the optional coating may be selected, for example, to act as an insulator, improve radiopacity, improve and/or alter RF energy conduction, improve lubricity, and/or reduce tissue adhesion.

The filaments 319a, 319b may also act as RF energy delivery elements. The filaments 319a, 319b may be constructed in a manner similar to as described with respect to the filaments 206a, 206b.

The tip 311 of FIG. 3C includes a filament slot 318a and a filament slot 318b. The geometry of the filament slots 318a, 318b may be selected to allow filaments 319a, 319b to be adequately retracted (e.g., such that they are in a cross-sectional envelope of the second body portion 315) while the needle 309 is inserted into the body, so that the filaments 319a, 319b do not cause any unintended damage to the patient (e.g., by being along the second body portion 315). Such positioning of the filament slots 318a, 318b may avoid having filament exit features on the tapered portion 313 and on the first body portion 314, which may avoid potential coring. The internal geometry of the filament slots 318a, 318b may include a transition region that meets the outer surface of the second body portion 315 at an angle, and advancement of filaments 319a, 319b without a pre-set bias (e.g., substantially straight) relative to the filament slots 318a, 318b can causes the filaments 319a, 319b to be deflected outwardly as the filaments 319a, 319b move distally along the transition region.

The configuration and orientation of the filament slots 318a, 318b may be selected such that deployed filaments 319a, 319b may achieve the positioning illustrated in FIG. 3C. In FIG. 3C, the filaments 319a, 319b are generally positioned in a plane that is perpendicular to a plane that includes the angle 316 between the first and second body portions 314, 315. As illustrated, the filaments 319a, 319b may be positioned such that they extend at an angle (e.g., about 15°, between about 10° and about 90°, between about 10° and about 60°, between about 10° and about 45°, between about 10° and about 20°, combinations thereof, and the like) relative to the plane that includes the angle 316. Other angles are also possible. Other filament slot 318a, 318b configurations may be configured to achieve other desired filament 319a, 319b placements. These configurations may be achieved, for example, by varying the quantity of filament slots and filaments, the placement of filament slots about the circumference of the tip 311, the angle at which the filaments extend away from the first and second body portions 314, 315, and/or the placement of filament slots along the first and second body portions 314, 315.

FIG. 3G illustrates an example embodiment of a tip 321 that includes a filament slot 318a and a filament slot 318b along the first body portion 314. The geometry of the filament slots 318a, 318b may be selected to allow filaments 319a, 319b to be adequately retracted (e.g., such that they are in a cross-sectional envelope of the second body portion 315) while the needle 309 is inserted into the body, so that the filaments 319a, 319b do not cause any unintended damage to the patient. Positioning of the filament slots 318a, 318b along the first body portion 314 may potentially cause coring, so the filaments 319a, 319b may be configured to substantially occlude the filament slots 318a, 318b, which may avoid potential coring. The internal geometry of the filament slots 318a, 319b may lack a transition region and, due to being positioned on the first body portion 314, advancement of the filaments 319a, 319b without a pre-set bias (e.g., substantially straight) can cause the filaments 319a, 319b to continue to advance substantially straight (e.g., along the longitudinal axis of the elongate member 317 and/or the second body portion 315) as the filaments move distally out of the filament slots 318a, 318b. Although not illustrated, placement of filament slots along the tapered portion 313 is also possible (e.g., the filaments continuing to advance along the longitudinal axis of the first body portion 314). Although not illustrated, the embodiments depicted in FIGS. 3A and 3D may be adapted so the filaments 206a, 206b exit along the tapered portion 302.

The needle 309 may comprise a tube that includes a lumen therethrough, for example as described herein with respect to FIGS. 3A, 3B, 3D, and 3E. The lumen may be employed to accept an RF probe for delivery of RF energy and/or for the transport of fluids. In this regard, the tip 311 may further include a fluid port 320 that may be in fluid communication via a channel through the tip 311 with the lumen. The fluid port 320 may be used to transfer fluid between the region of the tip 311 and a proximal end of the needle 309.

In the deployed position as shown in FIG. 3C, the distal ends of the filaments 319a, 319b are disposed away from the point 312. In the deployed position as shown in FIG. 3G, the distal ends of the filaments 319a, 319b are disposed away from the point 312. In a retracted position (not shown, but similar to as shown in FIGS. 3B and 3E), the distal ends of the filaments 319a, 319b are entirely within an outer perimeter (e.g., circumference where the second body portion 315 of the tip 311, 321 is round) of the tip 311, 321. In the deployed position, the filaments 319a, 319b act as broadcast antennae for an RF probe inserted into the needle 309. The tip 311 or 321, the filament 319a, and/or the filament 319b may form a monopolar electrode for application of RF energy to the target volume. The filaments 319a, 319b may allow the RF energy from the RF probe to be dispersed over a larger volume than would be possible with the tip 311, 321 alone.

In general, any or all of the herein variables may be incorporated into a particular embodiment of a needle to yield a needle capable of producing a lesion with a particular size, position and shape relative to the tip of the needle. Such custom sizes, positions and shapes may be designed for specific procedures. For example, a particular lesion size, position and shape may be selected to enable a user to navigate the needle to a particular landmark (e.g., proximate to or touching a bone visible using fluoroscopy) and then orient the needle such that deployed filaments will be operable to produce a lesion at a particular location relative to the landmark. By navigating to a particular internal landmark, as opposed to attempting to visualize a relative position of a needle offset from a landmark, a more accurate and/or consistent positioning of the needle may be achieved. In this regard, the skill level required to accurately position the needle for a particular procedure may be reduced.

The lesion shapes achievable through selection of the herein variables may include, for example, generally spherical, oblong, conical, and pyramidal shapes. The orientation relative to, and the amount of offset from, the tip of such shapes may be selectable. In an embodiment, the tips of the deployed filaments may be positioned distally relative to the point of the tip to provide for a facile positioning of the lesion relative to the tip. Such capability may allow for the needle to be inserted directly toward a target volume. In other embodiments, the tips of the deployed filaments may be positioned at the same axial position along the central longitudinal axis as the point of the tip or the tips of the deployed filaments may be positioned proximally relative to the point of the tip. In other embodiments, some filament endpoints may be located distal to the point of the tip while others are proximal to the point of the tip.

The elongate member 203 may be in the form of a hollow tube (e.g., sheath, cannula) interconnecting the tip 201, 211 with the hub 204. The elongate member 203 may be configured with adequate strength to allow the needle 103 to pierce a patient's skin and advance to a target area through various tissue types, including, for example, fat and muscle tissue. The elongate member 203 may also be capable of resisting kinking as it is advanced. In some embodiments, the elongate member 203 comprises a rod with a plurality of lumens along its length to accommodate the filaments 206a, 206b, the RF probe 401, and/or a fluid passage.

The elongate member 203 houses portions of the filaments 206a, 206b and the tube 207, and allows for relative movement of the filaments 206a, 206b. The elongate member 203 may be of any appropriate size and internal configuration to allow insertion into a patient and to house componentry therein. In some embodiments, the elongate member 203 is a 16 gauge round tube or smaller. For example, the elongate member 203 may be 18 gauge or 20 gauge. In some embodiments, the elongate member 203 has a maximum cross-sectional dimension of about 1.7 mm. In some embodiments, the elongate member 203 has a maximum cross-sectional dimension of about 1 mm. The elongate member 203 may have a length selected for performing a specific spinal RF neurotomy procedure on a particular patient. In some embodiments, the elongate member 203 has a length of about 10 cm.

In certain embodiments, the elongate member 203 comprises (e.g., is constructed from) an insulative material to reduce (e.g., eliminate) the amount of RF energy emitted along the length of the elongate member 203 when the RF probe 401 is disposed therein. For example, the elongate member 203 may comprise (e.g., be constructed from) polymeric, ceramic, and/or other insulative material. In certain embodiments, the elongate member 203 includes an insulating coating or sleeve 307 (FIGS. 2D and 16D). In some embodiments, the elongate member is insulated (e.g., constructed from insulative material and/or having an insulating coating 307) except for a distal part having a length between about 5 mm and about 10 mm. FIG. 3H illustrates an example embodiment of a needle 309 comprising an insulating coating 330 covering a proximal portion of the tip 321 and coatings 332a, 332b covering a proximal portion of the filaments 319a, 319b. The coating 330 insulates, inter alia, the bent area between the first body portion 314 and the second body portion 315 of the tip 321.

In some embodiments, the elongate member is insulated (e.g., constructed from insulative material and/or having an insulating coating) except for a proximal part. FIG. 3I illustrates an example embodiment of a needle 309 comprising an insulating coating 330 covering a distal portion of the tip 321 and coatings 332a, 332b covering a distal portion of the filaments 319a, 319b. In some embodiments in which the distal portion of the tip 321 is, the needle 309 may create a kidney or catcher's mitt shaped lesion, which may be useful, for example, for ablating tissue where the active tip is pressed against the wall of a structure with the device staying in the lumen of a structure. For example, when ablating endocardial lesions in which the device accesses the target through a cardiac chamber, insulating the distal portion of the tip 321, which stays in the chamber, can make the biophysics of the lesion (e.g., impedance, power, heat) more precise because the insulated distal portion of the tip 321 that is surrounded by blood in the chamber will not be part of the field.

FIGS. 3H and 3I illustrate example embodiments of insulation of parts of the tip 321 and the filaments 319a, 319b illustrated in FIG. 3G. Parts of components of the distal ends of other needle tips described herein may also be insulated (e.g., those illustrated in FIGS. 3A, 3C, and 3D). In some embodiments, only parts of the tip 321, and not parts of the filaments 319a, 319b, are insulated. In some embodiments, only parts of the filaments 319a, 319b, and not parts of the tip 321, are insulated. In some embodiments, a distal portion of the tip 321 is insulated (e.g., as illustrated in FIG. 3I) and proximal portions of the filaments 319a, 319b are insulated (e.g., as illustrated in FIG. 3H). In some embodiments, a distal portion of the filaments 319a, 319b are insulated (e.g., as illustrated in FIG. 3I) and a proximal portion of the tip 321 is insulated (e.g., as illustrated in FIG. 3H). In some embodiments, the insulative coating or sleeve 330, 332a, 332b may be adjustable. For example, one or all of the sleeves 330, 332a, 332b may be advanced or retracted relative to the tip 321, the filament 319a, and the filament 319b, respectively, to increase or decrease the amount of exposed conductive area.

The elongate member 203 may include a coating that may improve radiopacity to aid in visualization of the position of the needle 103 using fluoroscopy. The elongate member 203 may include a lubricious coating to improve its ability to be inserted and positioned in the patient and/or to reduce tissue adhesion. The elongate member 203 may include markers 224 along its length to assist in determining the depth to which the needle 103 has entered into the anatomy. The markers 224 may be radiopaque so that they may be viewed under fluoroscopy. A collar (not shown) may be disposed about the elongate member 203 to assist in placement of the tip 201, 211 of the needle 103. For example, the tip 201, 211 may be positioned in a first position, the collar may then be placed against the patient's skin, and then the needle 103 may be advanced and/or withdrawn a certain distance. Such a distance may be indicated, for example, by the distance between the collar and a patient's skin or other anatomy.

The elongate member 203 may be fixedly interconnected to the tip 201, 211 and the hub 204 in any appropriate manner. For example, the tip 201, 211 may be press fit into the elongate member 203 and the elongate member 203 may be press fit into the hub 204. Other example methods of attachment include adhesive bonding and welding. In some embodiments, the elongate member 203 and the tip 201, 211 are a single unitary structure. The elongate member 203 may be steerable and incorporate controlling mechanisms allowing the elongate member 203 to be deflected or steered after insertion into the anatomy.

The tube 207 containing the lumen 222 may comprise (e.g., be constructed from) any appropriate material. For example, the tube 207 comprise a conductive material, such as stainless steel (e.g., 300 Series Stainless Steel), such that when the RF probe 401 is inserted in the tube 207, the RF energy emitted by the RF probe 401 may be conducted through the tube 207 and into and through the tip 201, 211, the filament 206a, and/or the filament 206b. The tube 207 may be interconnected to the tip 201, 211 such that the lumen 222 is in sealed, fluid communication with the channel through the tip 201, 211. This may be accomplished by a press fit, weld, or any other appropriate method.

As noted, the lumen 222 may be in fluid communication with the tip 201, 211 at the distal end 202. A proximal end of the lumen 222 may be disposed at the proximal end 205 of the needle 103. In this regard, the lumen 222 may extend from the distal end 202 to the proximal end 205, with the only access being at the distal and proximal ends 202, 205. In some embodiments, the lumen 222 is the only lumen of the needle 103 disposed along the elongate member 203.

The RF probe 401 inserted into the lumen 222 may be positioned such that an end of the RF probe 401 is proximate to the tip 201, 211. For example, the RF probe 401 may be positioned such that the distal end 402 of the RF probe 401 is in the lumen 222 near the tip 201, 211 or in the channel through the tip 201, 211. RF energy transmitted through the RF probe 401 may then be conducted by the tip 201, 211, the filament 206a, and/or the filament 206b. The size of the lumen 222 may be selected to accommodate a particular size of RF probe 401. For example, the lumen 222 may be configured to accommodate at least a 22 gauge RF probe 401, at least a 21 gauge RF probe 401, or a larger or smaller RF probe 401. For another example, the lumen 222 may have a maximum cross-sectional dimension of less than about 0.85 mm.

The proximal end of the tube 207 may be operable to receive the RF probe 401. The proximal end of the tube 207 and the actuator 216 may be configured to accept a connector, such as a Luer fitting, such that a fluid source may be connected to the tube 207 (e.g., to deliver fluid through the lumen 222 and out the fluid port 210).

The needle 103 includes two filaments 206a, 206b in and along elongate member 203. Distal ends of the filaments 206a, 206b are proximate to the tip 201, 211, and proximal ends of the filaments 206a, 206b are fixed to a filament hub 221 discussed below. The filaments 206a, 206b are movable along the central longitudinal axis 223 between a fully deployed position as illustrated in FIGS. 3A, 3C, 3D, and 3F and a retracted position illustrated in FIGS. 3B and 3E. Moving the filaments 206a, 206b distally from the retracted position moves the filaments 206a, 206b toward the fully deployed position, while moving the filaments 206a, 206b proximally from the deployed position moves the filaments 206a, 206b toward the retracted position. The filaments 206a, 206b may be deployed in intermediate positions between the fully deployed positions and the retracted positions. For example, a mechanism for advancement and/or retraction of the filaments 206a, 206b may include detents indicating partial deployment and/or retraction and a stop indicating full deployment and/or retraction.

In the fully deployed position, the distal ends of the filaments 206a, 206b, 319a, 319b are disposed away from the tip 201, 211, 311, 321. In the retracted position, the distal ends of the filaments 206a, 206b, 319a, 319b are entirely within an outer perimeter (e.g., circumference where the body portion 303 of the tip 201, 211, 311, 321 is round) of the tip 201, 211, 311, 321. In the deployed position, the filaments 206a, 206b, 319a, 319b can act as broadcast antennae for the RF probe 401 (e.g., RF energy passes from the RF probe 401 to the tip 201, 211, 311, 321 and to the filaments 206a, 206b, 319a, 319b, and into a target volume within a patient). In this regard, together, the RF probe 401 inserted into the lumen 222, the tip 201, 211, 311, 321, and the filaments 206a, 206b, 319a, 319b, may form a monopolar electrode for application of RF energy to the target volume. The filaments 206a, 206b, 319a, 319b allow the RF energy from the RF probe 401 to be dispersed over a larger volume than would be possible with the tip 201, 211, 311, 321 alone.

The filaments 206a, 206b, 319a, 319b may be constructed from a material operable to conduct RF energy, e.g., a metal such as stainless steel (e.g., 303 Stainless Steel), Nitinol, or shape memory alloy. The filaments 206a, 206b may be coated, for example to enhance and/or inhibit their ability to conduct RF energy. The filaments 206a, 206b may include a lubricious coating to aid in insertion and/or reduce tissue adhesion.

Figure 2B:
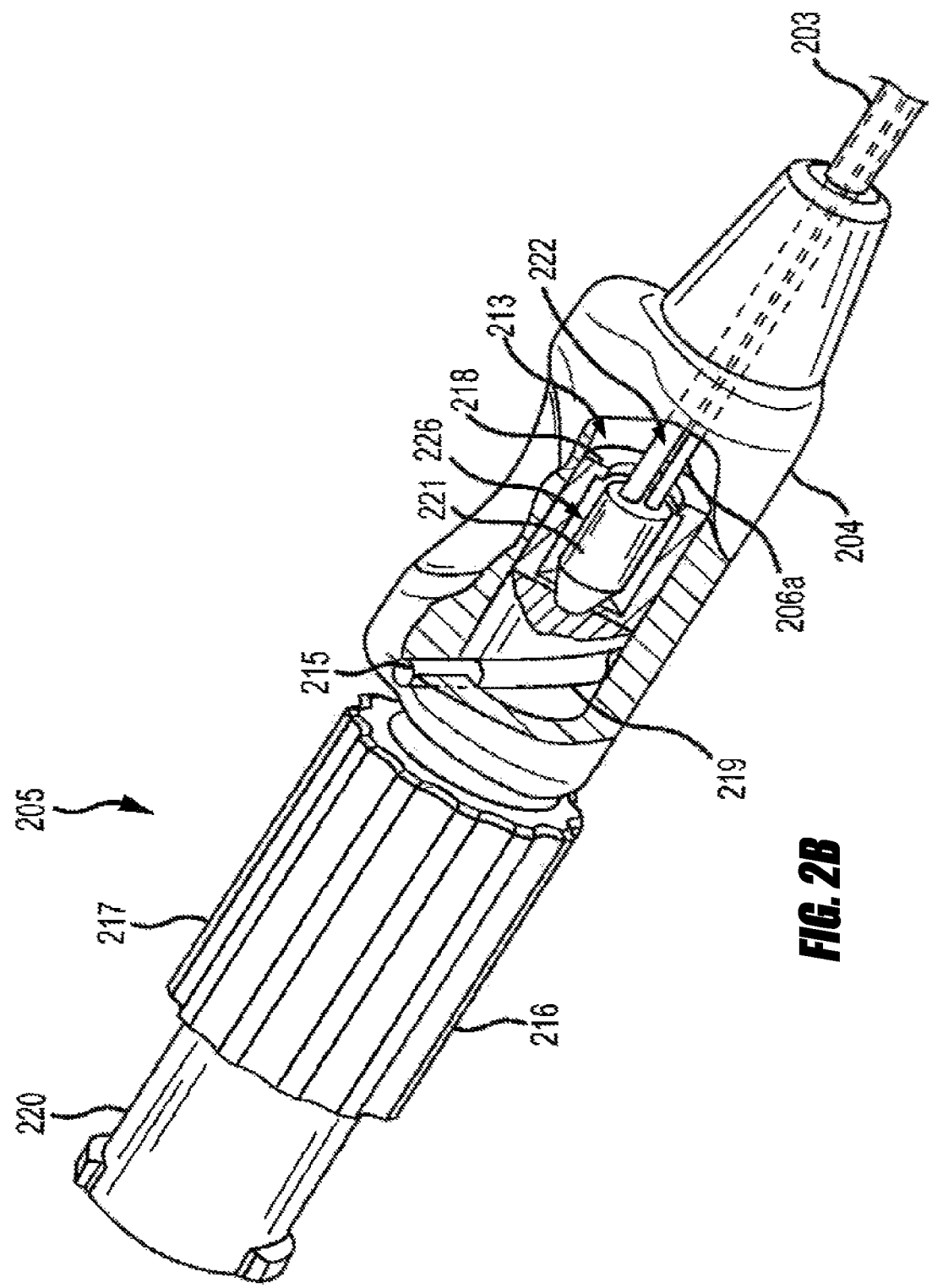
FIG. 2B is a cut away perspective view of a portion of the needle of FIG. 2A.
Figure 2C:
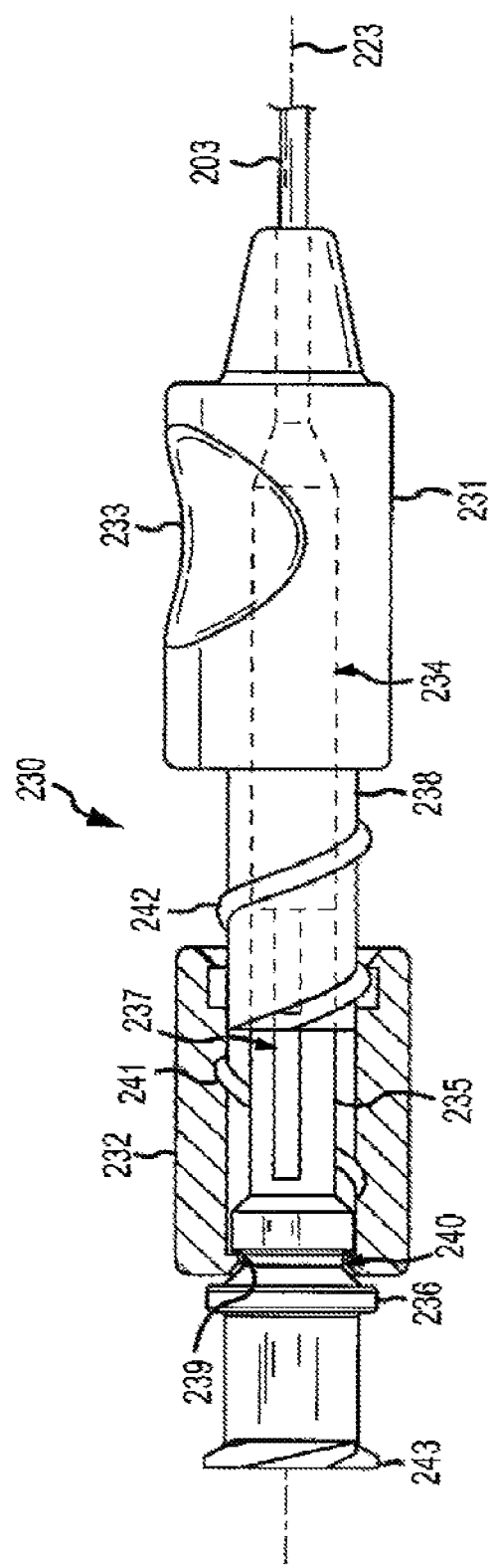
FIG. 2C is a partial cut away and partial cross-sectional view of a portion of another example embodiment of a needle that may be used in an RF neurotomy procedure.
Figure 2E:
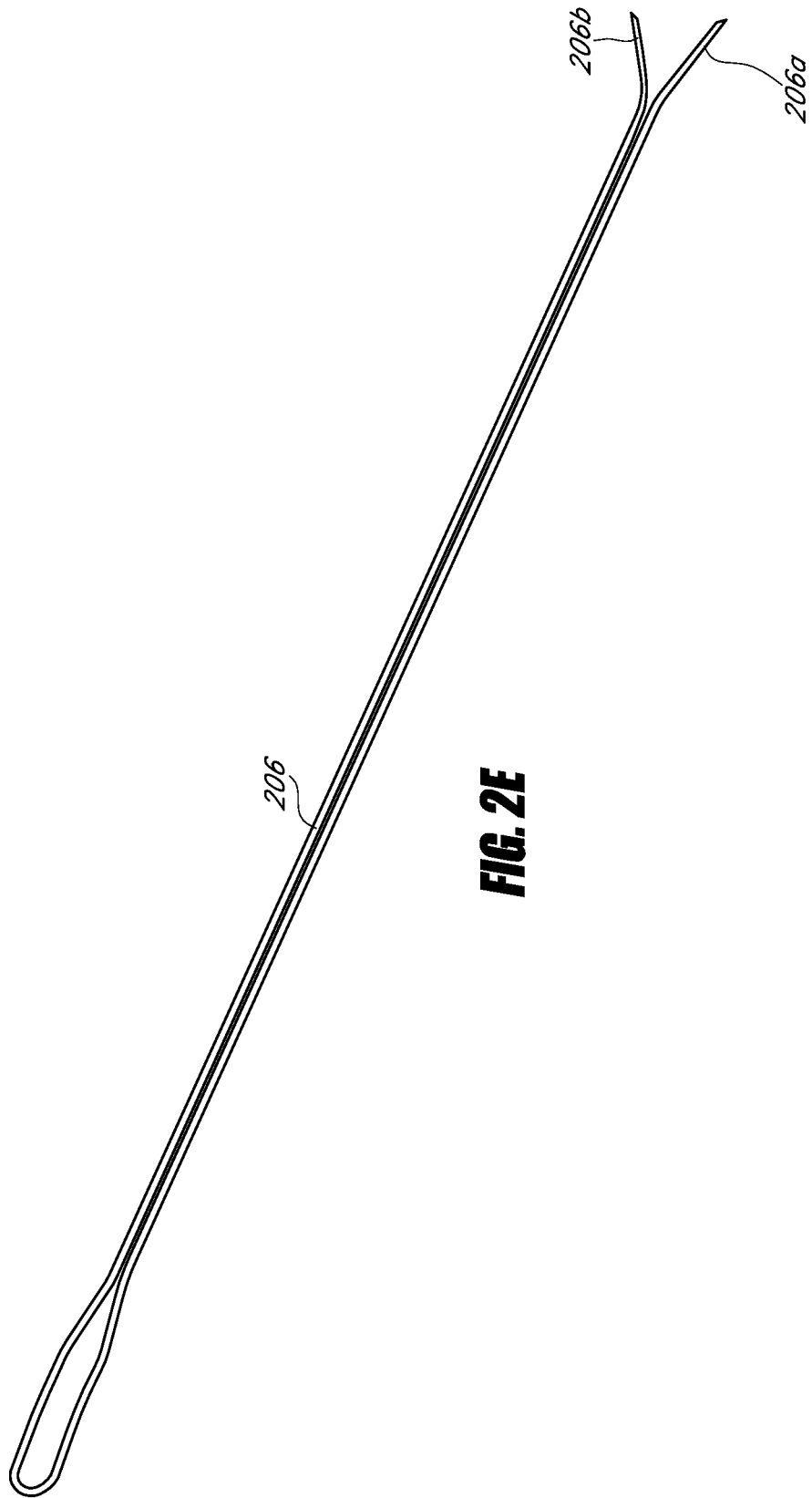
FIG. 2E is a perspective view of an example embodiment of filaments formed from a single wire.

FIG. 2E illustrates an embodiment in which the filaments 206a, 206b are formed from a single wire 206 that is bent at the proximal end. The distal ends of the filaments 206a, 206b are shown as bent, which can be the result of deflection upon exit from a tip 201, 211, shape memory, combinations thereof, and the like. Forming the filaments 206a, 206b from a single wire 206 may provide advantages such as, for example, coherent activation of the filaments 206a, 206b, simultaneous deployment of the filaments 206a, 206b, and/or simultaneous retraction of the filaments 206a, 206b. It will be appreciated that the wire 206 may be a single wire or a plurality of wire segments joined together (e.g., via adhering with conductive epoxy, welding, soldering, combinations thereof, and the like). Other filaments described herein may also be coupled or bent at the proximal end. The filaments 206a, 206b illustrated in FIG. 2E are substantially parallel, and taper outwards before being bent at the proximal end. In some embodiments, the filaments 206a, 206b are substantially parallel and do not taper out before being bent at the proximal end. In certain such embodiments, the proximal end of the wire 206 is a semi-circle, for example having a radius between about 0.03 inches and about 0.07 inches (approx. between about 0.76 mm and about 1.8 mm), between about 0.04 inches and about 0.06 inches (approx. between about 1 mm and about 1.5 mm), between about 0.05 inches and about 0.055 inches (approx. between about 1.3 mm and about 1.4 mm) (e.g., about 0.052 inches (approx. about 1.32 mm)), combinations thereof, and the like. In some embodiments, the filaments 206a, 206b are parallel and spaced by a distance between about 0.025 inches and about 0.125 inches (approx. between about 0.64 mm and about 3.2 mm), between about 0.05 inches and about 0.1 inches (approx. between about 1.3 mm and about 2.5 mm) (e.g., about 0.075 inches (approx. about 1.9 mm)), combinations thereof, and the like. In some embodiments, the filaments 206a, 206b in the elongate member 203 may be braided, wrapped, or twisted together. Such embodiments may increase column strength, providing resistance to buckling and/or bending in the elongate member 203. In some embodiments, the wire 206 has a diameter between about 0.0025 inches and about 0.04 inches (approx. between about 0.06 mm and about 1 mm), between about 0.005 inches and about 0.025 inches (approx. between about 0.13 mm and about 0.64 mm), between about 0.01 inches and about 0.02 inches (approx. between about 0.25 mm and about 0.5 mm) (e.g., about 0.014 inches (approx. about 0.36 mm)), combinations thereof, and the like. Other diameters are also possible. In some embodiments, the filaments 206a, 206b each have a diameter between about 0.0025 inches and about 0.04 inches (approx. between about 0.06 mm and about 1 mm), between about 0.005 inches and about 0.025 inches (approx. between about 0.13 mm and about 0.64 mm), between about 0.01 inches and about 0.02 inches (approx. between about 0.25 mm and about 0.5 mm) (e.g., about 0.014 inches (approx. about 0.36 mm)), combinations thereof, and the like. Other diameters are also possible. In some embodiments, the filaments 206a, 206 have different diameters (e.g., by being formed from different wires, by being formed from portions of wires with different diameters that are coupled to form the wire 206, etc.).

The distal ends of the filaments may be shaped (e.g., pointed) to improve their ability to move through tissue. For example, the tips of the filaments 206a, 206b in FIG. 3A have an outward-facing bevel. In some embodiments, the bevel is at an angle between about 15° and about 45°, between about 20° and about 40°, between about 25° and about 35° (e.g., about 30°), combinations thereof, and the like. In embodiments in which the filaments 206a, 206b each have a diameter of about 0.014 inches (approx. about 0.36 mm) and a bevel of about 30°, the length of the bevel is about 0.024 inches (approx. about 0.61 mm). The tips of the filaments 206a, 206b may have the same shape (e.g., beveled) or different shapes. For another example, the tips of the filaments 206a, 206b in FIG. 3D have an inward-facing bevel. In certain embodiments, bevels (e.g., inward-facing bevels) can help to induce splay between the tips of the filaments 206a, 206b (e.g., splay of between about 15° and about 20°) by tracking to one side (e.g., away from the beveled side) upon deployment, which can improve placement of the filaments 206a, 206b. For yet another example, the tips of the filaments 319a, 319b in FIG. 3G have a pencil-point. In certain embodiments, a pencil-point tip can help to reduce splay between the tips of the filaments 206a, 206b by substantially straight tracking deployment, which can improve placement of the filaments 206a, 206b. In some embodiments, the filaments 206a, 206b comprise materials with different tensile strength and/or rigidity, and the filaments 206a, 206b, which can affect their ability to flex due to contact with tissue and thus the amount of splay, if any. In certain embodiments in which the filaments 206a, 206b comprise a shape memory material, the deflection to an unconfined state may work with or against the shapes of the tips. In some embodiments, certain filament tips may help to occlude filaments slots, improve interaction with a transition region, etc. Although certain combinations of filament tips are illustrated with respect to certain embodiments herein, the various shapes of the filament tips described herein and otherwise may be selected for any of these embodiments (e.g., the filaments 206a, 206b of FIG. 3A may have inwardly-facing bevels or pencil-point tips, the filaments 206a, 206b of FIG. 3D may have outwardly-facing bevels or pencil-point tips, the filaments 319a, 319b of FIG. 3C may have inwardly-facing bevels or pencil-point tips, the filaments 319a, 319b of FIG. 3G may have inwardly-facing bevels or outwardly-facing bevels, etc.).

Figure 5:
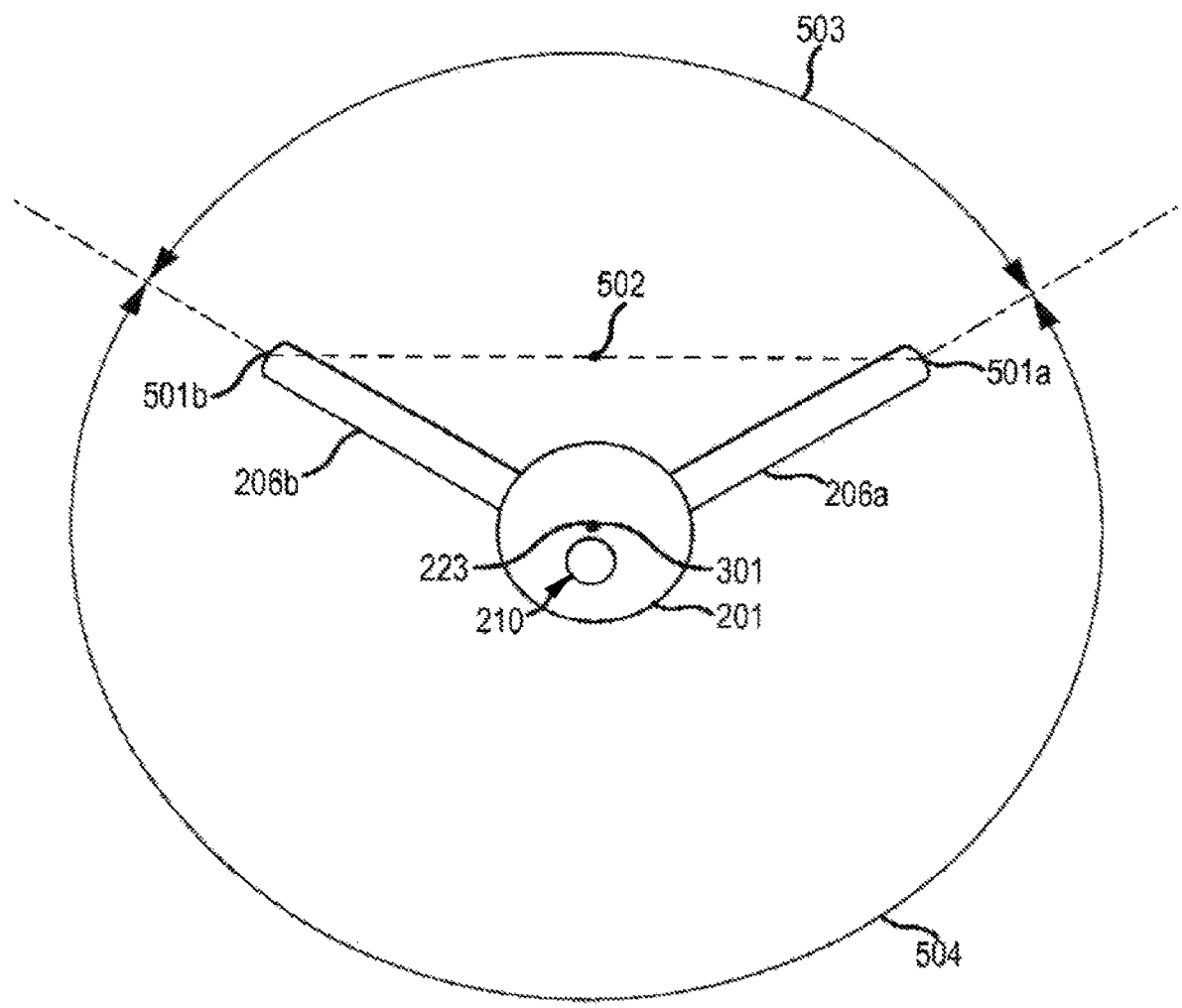
FIG. 5 is a proximal-facing end view of an example embodiment of a needle tip.

The positioning of the filaments 206a, 206b of the embodiments illustrated in FIGS. 3A and 3D will now be described in relation to FIG. 5. FIG. 5 is an end view of the tip 201 and deployed filaments 206a, 206b of the embodiment illustrated in FIGS. 2A and 3A. The filaments 206a, 206b are positioned at a filament angle 503 of about 120° apart from each other about the central longitudinal axis 223. This coincides with the positions of the filament slots 304a, 304b discussed herein since the filaments 206a, 206b emerge from the filament slots 304a, 304b. Other filament angles 503 are also possible. For example, the filament angle 503 may be between about 90° and about 180°, between about 90° and about 150°, between about 100° and about 140°, between about 110° and about 130°, combinations thereof, and the like. A filament-free angle 504 of about 240° is defined as the largest angle about the circumference of the tip 201, 211 that is free of filaments. In an embodiment consisting of two filaments 206a, 206b, the filament angle 503 may be less than 180° and the filament-free angle 504 may be correspondingly greater than 180° (e.g., greater than 200° or greater than 240°).

In FIG. 5, the central longitudinal axis 223 is perpendicular to the plane of the illustration. A midpoint 502 is defined between distal ends 501a, 501b of the filaments 206a, 206b, respectively. The midpoint 502 is offset from the central longitudinal axis 223. For example, in some embodiments, the midpoint 502 is offset from the central longitudinal axis 223 by about 2 mm. Other offset values are also possible. For example, the offset may be between about 0.5 mm and about 5 mm, between about 1 mm and about 4 mm, between about 1 mm and about 3 mm, greater than about 0.5 mm, less than about 5 mm, combinations thereof, and the like. When RF energy is transmitted from the tip 201 and both of the filaments 206a, 206b, the RF energy will be transmitted asymmetrically with respect to the central longitudinal axis 223 the cause the RF energy will be emitted from the tip 201 and the filaments 206a, 206b. As oriented in FIG. 5, the energy will be biased in an upward direction in the direction from the point 301 toward the midpoint 502. Thus, when RF energy is transmitted during an RF neurotomy procedure, a lesion will be created that is correspondingly offset from the central longitudinal axis 223 in the direction from the point 301 toward the midpoint 502.

Referring again to the asymmetric nature of the lesion, the lesion may be substantially a three-dimensional polygon (e.g., with rounded edges) of known dimensions and volume that is offset from the central cannula in a known and predictable way. Different embodiments may have different three-dimensional polygonal structures adapted to the intended ablation target. By contrast, needles without deployable filaments may be used to create asymmetric planar lesions by varying needle insertion during the ablation procedure, and may require substantial ablation volume overlap.

Figure 6:
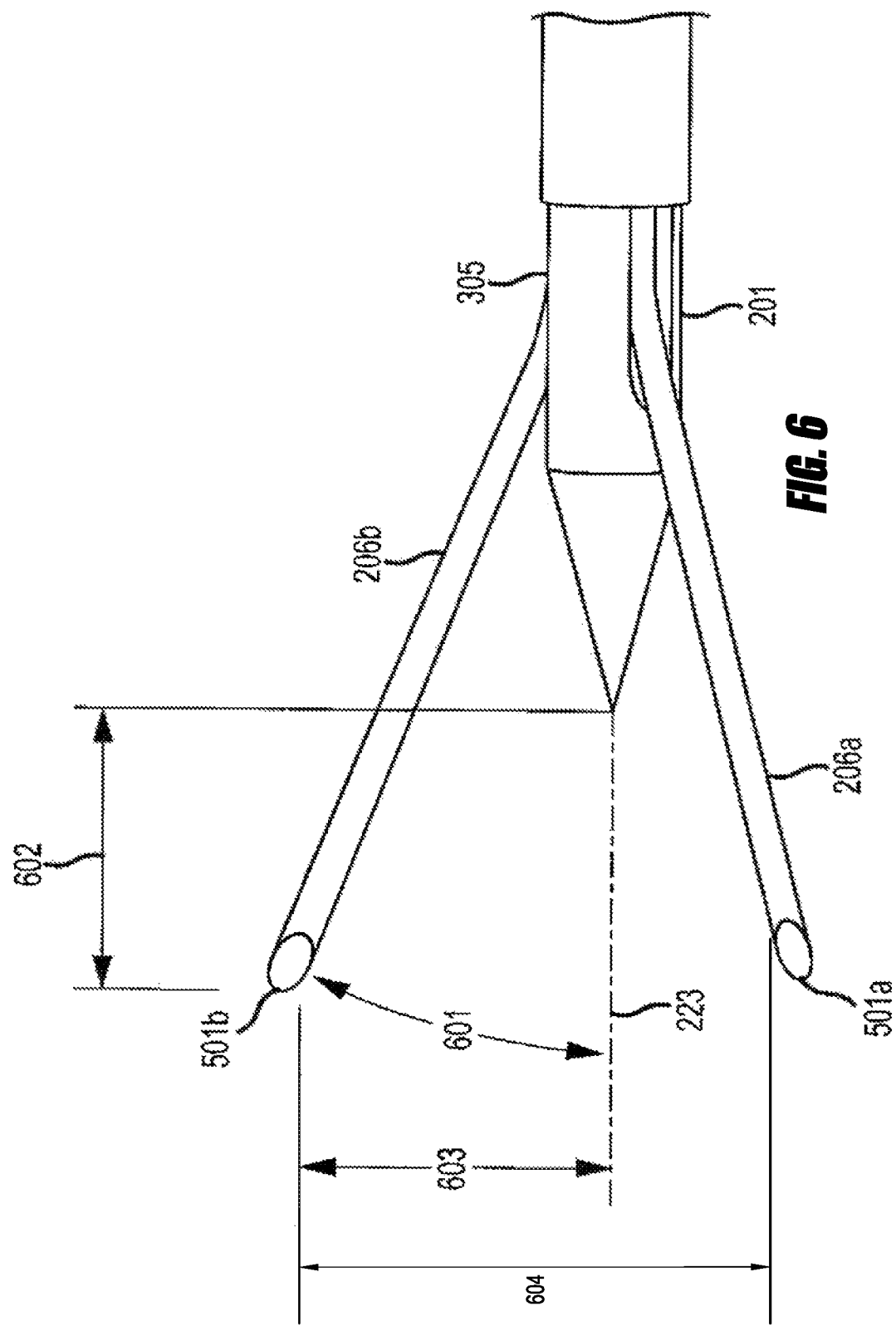
FIG. 6 is a side view of an example embodiment of a needle tip.

FIG. 6 is a side view of the tip 201 and the filaments 206a, 206b, oriented such that the deployed filament 206b is entirely within the plane of the figure. The filaments 206a, 206b extend from the tip 201 at a common distance, or location, along the central longitudinal axis 223. In some embodiments, the filaments 206a, 206b may extend different distances. The filament 206b is deflected radially outwardly from the central longitudinal axis 223. The filament 206b emerges from the tip 201 at an angle 601 of about 30° from the central longitudinal axis 223, which is parallel to the longitudinal axis of the elongate member 203. The angle 601 may vary, for example, based at least partially on positioning of a transition region 305, mechanical properties of the filament 206b (e.g., shape-memory properties or lack thereof), and the like. In some embodiments, the angle 601 is between about 5° and about 85°, between about 10° and about 60°, between about 20° and about 40°, greater than about 5°, less than about 85°, combinations thereof, and the like. In some embodiments, the angle 601 is related to the angle 503. For example, the angle 601 may be a fraction of the angle 503, such as about ¼. In some embodiments, the angle 601 is unrelated to the angle 503, for example both being independently chosen to produce a certain lesion size or shape. In some embodiments, the distal tips 501a, 501b are positioned distally beyond the point 301 by a distance 602, are disposed at a distance 603 from the central longitudinal axis 223, and/or are disposed at a distance 604 from each other. In some embodiments, the distance 602 is about 3.5 mm, the distance 603 is about 3 mm, and/or the distance 604 is about 4.5 mm. Other distances are also possible. For example, in some embodiments, the distance 602 is between about 0.5 mm and about 6 mm, between about 1 mm and about 5 mm, between about 3 mm and about 4 mm, combinations thereof, and the like. Other distances are also possible. For another example, in some embodiments, the distance 603 is between about 0.5 mm and about 6 mm, between about 1 mm and about 5 mm, between about 2 mm and about 4 mm, combinations thereof, and the like. Other distances are also possible. For yet another example, in some embodiments, the distance 604 is between about 2 mm and about 7 mm, between about 3 mm and about 6 mm, between about 4 mm and about 5 mm, combinations thereof, and the like. Other distances are also possible.

The angles described herein (e.g., the angles 503, 601) may be measured with respect to a needle 103 in a deployed state outside of a patient's body, and that the angles may when the needle is inside a patient's body, for example based at least in part on splay of filaments due to beveling.

The tip 211 and deployed filaments 206a, 206b of the embodiment illustrated in FIG. 3D may also have a filament angle 503, a filament-free angle 504, a midpoint 502, an angle 601, distances 602, 603, 604, and other features described herein, for example with respect to FIGS. 5 and 6. In some embodiments, the portion of the lesion based at least partially on RF energy emitted by the tip 211, and thus the shape of the lesion, may vary based on the position of the point 301 (e.g., in FIG. 3d, the point 301 is on the side of the tip 211 that comprises the filaments 206a, 206b).

The configuration of the filaments 206a, 206b illustrated in FIGS. 2A, 3A, 3D, 5, and 6 may be operable to produce lesions that are radially offset from the central longitudinal axis 223 and distally offset from the point 301 as compared to a lesion created by the tip 201, 211 without the filaments or a lesion created with the needle 103 with the filaments 206a, 206b in the retracted position.

Variations in the relative shapes, positions, and sizes of lesions created with the needle may be achieved by repositioning the filaments. For example, as noted herein, the lesion produced by the needle will be in different positions depending on whether the filaments are in the deployed or retracted positions. Lesions having intermediate shapes, positions, and/or sizes may be achieved by positioning the filaments in intermediate positions between the fully deployed (e.g., as illustrated in FIGS. 3A, 3C, 3D, and 3G) and fully retracted positions (e.g., as illustrated in FIGS. 3B and 3E). As noted herein, the needle with deployed filaments is operable to produce larger lesion volumes than the needle with retracted filaments. For example, the needle with fully deployed filaments may be operable to produce lesion volumes of about 500 mm$^3$. Other lesion volumes are also possible. For example, the needle with fully deployed filaments may be operable to produce lesion volumes between about 100 mm$^3$ and about 2,000 mm$^3$, between about 200 mm$^3$ and about 1,000 mm$^3$, between about 250 mm$^3$ and about 750 mm$^3$, between about 400 mm$^3$ and about 600 mm$^3$, combinations thereof, and the like.

Further variation in the shape, position, and/or size of lesions created by needles with deployable filaments may be achieved by different configurations of filaments. Variations may include, for example, variations in materials, the number of filaments, the radial positioning of the filaments, the axial positioning of the filaments, the length of the filaments, the angle at which the filaments exit the tip, the shape of the filaments, etc. By varying these parameters, the needle may be configured to produce lesions of various sizes and shapes that are positioned at various locations relative to the tip. Such variations may be specifically tailored to be used in specific procedures, such as RF neurotomy procedures of particular nerves adjacent to particular vertebrae.

Variations of the materials used for the tip and/or the filaments may be selected to achieve particular lesion sizes, positions, and/or shapes. For example, the tip may comprise (e.g., be made form) a material that does not conduct RF energy, in which case RF energy from the RF probe 401 may be conducted by substantially only the deployed filaments. In certain such embodiments, emitting RF energy from the filaments may provide for a lesion with a larger offset from the central longitudinal axis 223 than would be produced if the tip conducts RF energy and acts as an electrode along with the filaments.

Another material-related variation that may affect lesion shape, size, and/or position is the addition and placement of insulation over the tip and/or over the filaments. For example, by placing a layer of insulation over a proximal part of the portions of the filaments that extend from the tip when in the deployed position, the shape of the lesion may be altered since RF energy may primarily emanate from the distal, non-insulated part of the filaments. For another example, by placing a layer of insulation over a proximal part of the tip, the shape of the lesion may be altered since RF energy may primarily emanate from the distal, non-insulated part of the tip. Other parts of the filaments and/or tip may also be covered by an insulating material, for example a distal part of the filaments and/or tip, an intermediate part of the filaments and/or tip, combinations thereof, and the like, for example as described with respect to FIGS. 3H and 3I.

Moreover, the materials used in making the filaments and tip may be selected based on RF conductivity. For example, by using a material for the tip that is less conductive of RF energy, the proportion of RF energy emanating from the tip as compared to that emanating from the filaments may be altered resulting in a corresponding change in lesion size, position and/or shape.

The RF needles and RF probes discussed herein may be constructed from materials that are Magnetic Resonance Imaging (MRI) compatible (e.g., titanium, aluminum, copper, platinum, non-magnetic 300 Series Stainless Steel, etc.). In certain such embodiments, MRI equipment may be used to verify the positioning of the needles and/or portions thereof and/or monitor the progress of an ablation procedure (e.g., RF neurotomy).

Figure 7:
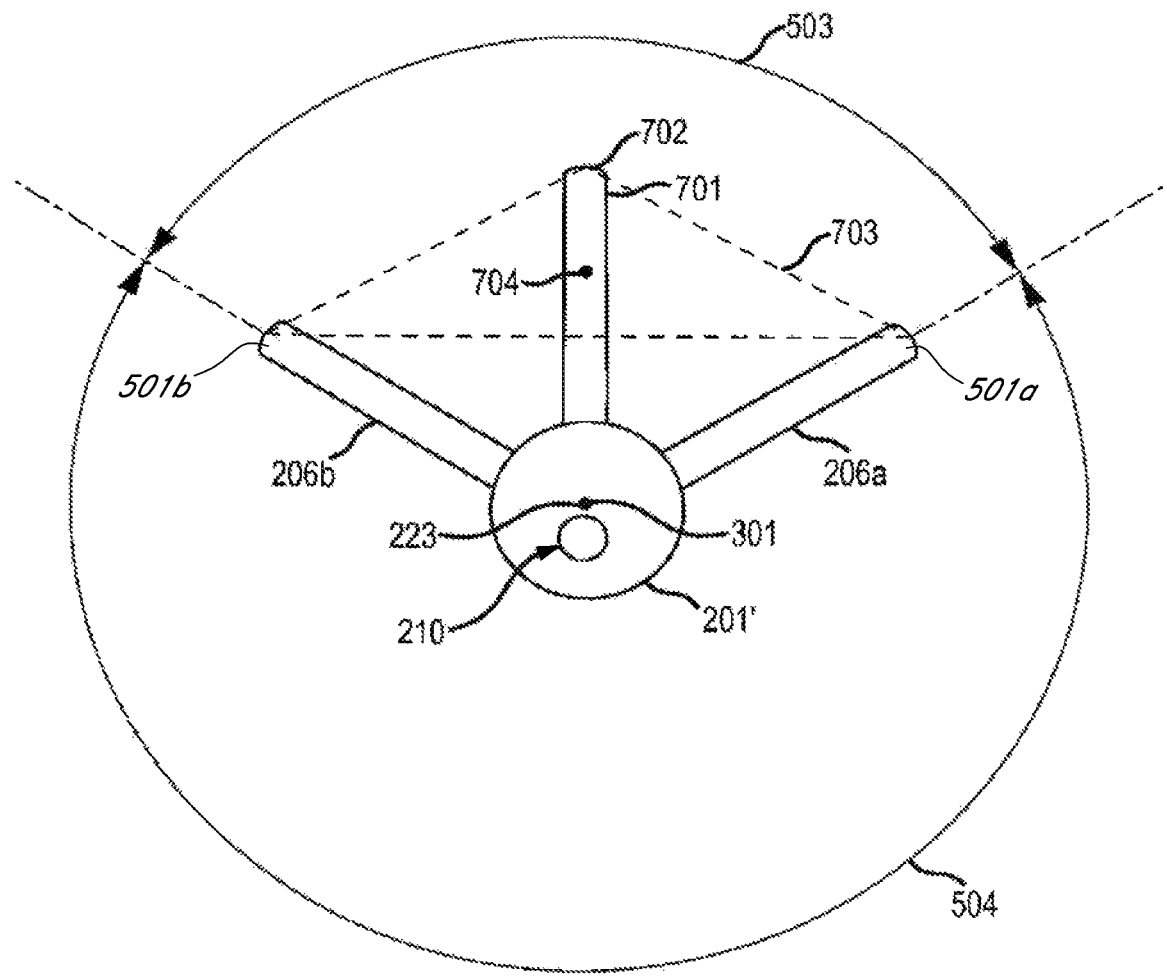
FIG. 7 is a proximal-facing end view of another example embodiment of a needle tip.

Variations of the number of filaments used for needle may be selected to achieve particular lesion sizes, positions and/or shapes. For example, as illustrated in FIG. 7, a third filament 701 may extend from the tip 201' (or other tips described herein such as the tip 211) in a position between filaments 206a, 206b. The tips 501a, 501b of the filaments 206a, 206b and a tip 702 of filament 701 may form a polygon 703 that has a centroid 704. The centroid 704 is offset from the central longitudinal axis 223. Such an arrangement may produce a lesion that is offset from the central longitudinal axis 223 to a different degree than, and shaped differently than, a lesion created by the needle of FIG. 5. In general, where a centroid of a polygon formed by the tips of filaments (or, in the case where there are two filaments, the midpoint between them) is offset from the central longitudinal axis 223, a lesion created by such a configuration will be correspondingly offset from the central longitudinal axis 223. The filaments 206a, 206b, 702 are positioned at the same filament angle 503 of about 120° as in the embodiment of FIG. 5. Other filament angles 503, in either FIG. 5 or FIG. 7, are also possible. The embodiment illustrated in FIG. 7 has a filament-free angle 504 of about 240°, also the same as in the embodiment of FIG. 5. Other filament-free angles 504, in either FIG. 5 or FIG. 7, are also possible. In general, in embodiments in which the filaments are positioned in a filament angle 503 that is less than about 180°, resultant lesions will be offset from the central longitudinal axis 223 in the direction of the filaments. In embodiments in which the filaments are positioned in a filament angle 503 that is less than about 180°, the filament-free angle is correspondingly greater than about 180° (e.g., greater than about 200° or greater than about 240°).

Figure 8:
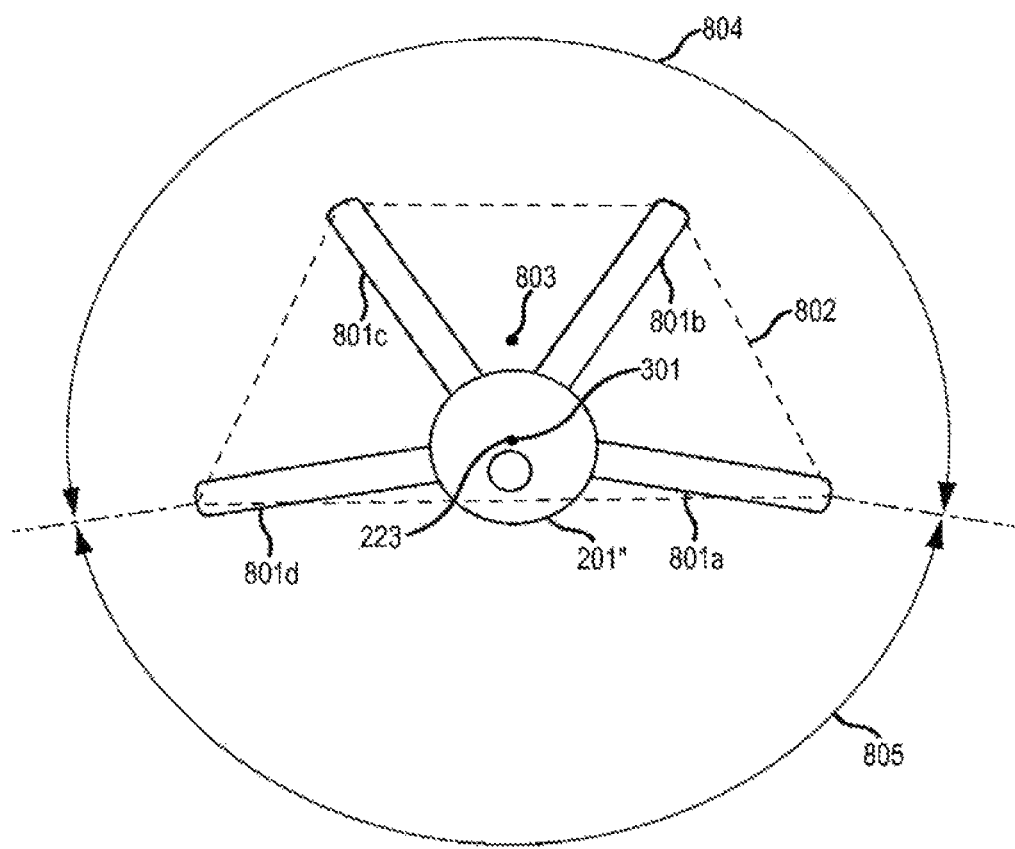
FIG. 8 is a proximal-facing end view of yet another example embodiment of a needle tip.

For another example, as illustrated in FIG. 8, four filaments 801a-801d are positioned about a tip 201" (or other tips described herein such as the tip 211). The tips of the filaments 801a-801d may form a polygon 802 that has a centroid 803. The centroid 803 is offset from the central longitudinal axis 223. Such an arrangement may produce a lesion that is offset from the central longitudinal axis 223 in the direction of the centroid 803. The filaments 801a-801d are positioned at a filament angle 804 of about 200°. Other filament angles 804 are also possible. The embodiment illustrated in FIG. 8 has a filament-free angle 805 of about 160°. Other filament-free angles 805 are also possible. FIG. 8 illustrates an embodiment in which the filament-free angle 805 is less than about 180°, but which is capable of producing a lesion offset from the central longitudinal axis 223.

In the herein-described embodiment of FIGS. 2A, 3A, 3B, 5, and 6 with two filaments, a midpoint 502 between the filaments was discussed. In embodiments with more than two filaments, a centroid of a polygon formed by the distal ends of the filaments was discussed. Both the midpoints and the centroids may be considered to be "average" points of the filaments for their particular configurations. In such embodiments, the midpoint between filaments in two-filament embodiments and the centroid of the polygon in embodiments with more than two filaments may be offset from the central longitudinal axis of the elongate member. For example, the midpoint or centroid may be offset from the central longitudinal axis by 1 mm or more. In embodiments, the polygon may lie in a plane perpendicular to the central longitudinal axis.

As illustrated in, for example, FIGS. 2A, 2D, 3A, 3C, 3D, 3G-3I, 5, 7, 8, 9, and 10, the distal ends of the filaments when fully deployed may be in a common plane. In some embodiments, the common plane is perpendicular or transverse to the central longitudinal axis. In some embodiments, the common plane is distal to the point 301, 312.

As illustrated in, for example, FIGS. 2A, 2D, 3A, 3C, 3D, 3G-3I, 5, 7, and 10, the filaments of the needle may all be deployed on a common side of a central plane of the needle (where the central longitudinal axis is entirely within the central plane). In certain such embodiments, the distal ends of the filaments are all on a common side of the central plane. Such a configuration may enable the needle to be used to create a lesion that is offset from the tip of the needle to the same side of the central plane as the deployed filament ends.

As illustrated, for example, in FIGS. 2A, 2D, 3A, 3C, 3D, 3G-3I, and 10, the filaments when fully deployed may point in an at least partially distal direction. In this regard, a vector extending longitudinally from the distal end of a filament and coinciding with a central axis of the portion of the filament out of the tip 211 has at least some distal component. The fully deployed filaments in the embodiments illustrated in FIGS. 2A, 2D, 3A, 3C, 3D, 3G-3I, and 10 all point in an at least partially distal direction.

Figure 9:
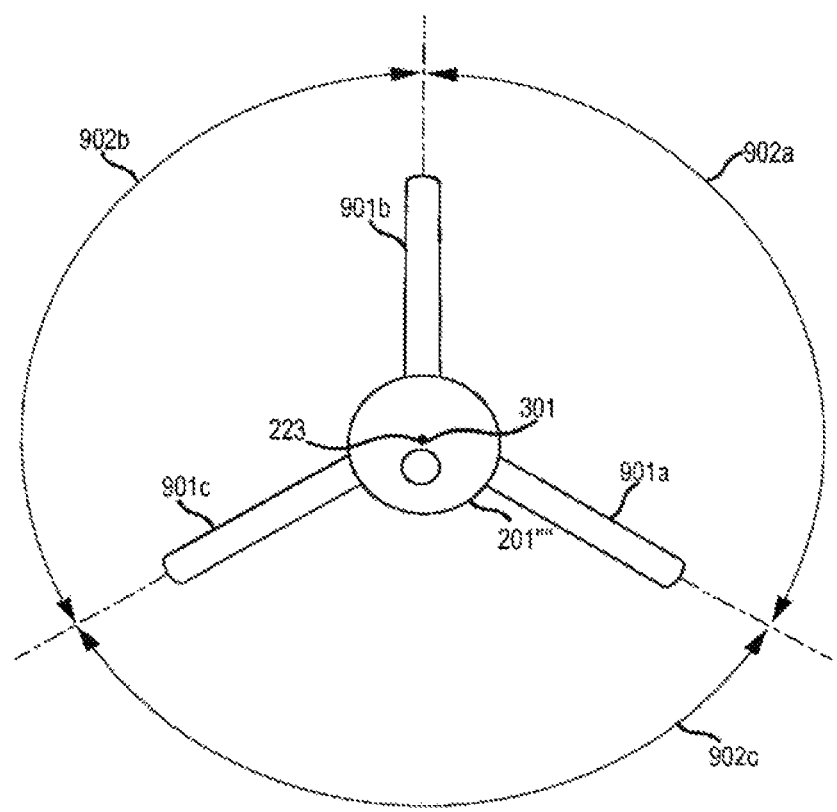
FIG. 9 is a proximal-facing end view of still another example embodiment of a needle tip.

FIG. 9 illustrates an embodiment in which the filaments are uniformly distributed about the circumference of the tip 201''''. The needle of FIG. 9 includes three filaments 901a, 901b, 901c distributed substantially equally about the circumference of the tip 201'''', the angles 902a, 902b, 902c between the filaments 901a, 901b, 901c each being about 120°. Such a needle may be operable to produce a lesion that is generally centered along the central longitudinal axis 223. However, the position of the produced lesion longitudinally along the central longitudinal axis 223 may be determined by the configuration (e.g., length, deployment angle, etc.) of the filaments. For example, relatively longer filaments may be operable to produce lesions that are positioned distal to lesions produced by configurations with relatively shorter filaments. For another example, in an embodiment in which the filament 901b is longer than the filaments 901a, 901c, the needle may be operable to create a lesion that is offset from the tip of the needle towards the filament 901b. For yet another example, in an embodiment in which the filaments 901a, 901b are longer than the filament 901c, the needle may be operable to create a lesion that is offset from the tip of the needle towards the filaments 901a, 901b.

Referring again to FIG. 7, if the filament 701 was distal to the filaments 206a, 206b, the resultant lesion may be longer along the central longitudinal axis 223 than lesions resulting from an embodiment in which the filaments 206a, 206b, 701 are each positioned along substantially the same plane perpendicular or transverse to the central longitudinal axis 223. In another variation, as deployed, two or more filaments may be at the same radial position and at different axial positions. Such embodiments may include multiple rows of filaments.

Referring again to FIGS. 5 and 6, if the lengths of the deployed portions of the filaments 206a, 206b were increased, the needle may be capable of producing lesions that are more distally positioned than lesions created by the embodiment as shown in FIGS. 5 and 6. The effects of lengthening or shortening the deployed length of the filaments may be similar to those discussed herein with respect to partially deploying filaments.

In some embodiments, the needle includes filaments having deployed portions with different lengths. In certain embodiments in which all of the filaments are deployed and/or retracted by a common actuator and/or are part of the same wire, variations in filament lengths may be achieved by varying the overall length of the filaments. For example, the distal end of a shorter filament may be retracted further into the tip or elongate member than the distal end of a longer filament. The effects of lengthening or shortening the length of the deployed portions of the filaments may be similar to those discussed herein with respect to variations in the axial positioning of filaments emergence from the tip of the needle and/or with respect to partially deploying filaments.

The angle at which a filament exits a tip (e.g., the angle 601 of FIG. 6) may be varied to achieve particular lesion sizes, positions, and/or shapes. For example, if the angle 601 in FIG. 6 was about 60°, the needle may be operable to produce a lesion that has a larger maximum cross-sectional dimension in a plane perpendicular to the central longitudinal axis 223 than if the angle 601 was about 30°, for example because the filaments can emanate RF energy at a distance further away from the central longitudinal axis. In some embodiments, the filaments can be deployed at different angles 601 relative to the central longitudinal axis 223.

Referring again to FIG. 10, the deployed portions of the filaments 1001a, 1001b may be curved. As described herein, the term "curved" may mean a continuous curve, a curve in combination with a straight section, a plurality of curves in different directions, combinations thereof, and the like. Such curvatures may be achieved, for example, by filaments 1001a, 1001b comprising shape memory material (e.g., Nitinol) or spring material. When the filaments 1001a, 1001b are retracted, the shape of the tip 201 and/or the elongate member 203 may cause the filaments 1001a, 1001b to be in constrained straightened configurations. As the filaments 1001a, 1001b are advanced toward the fully deployed position, they become unconstrained and return to their curved shapes as shown in FIG. 10. The deployed shape of the filaments 1001a, 1001b may be predetermined, or the filaments 1001a, 1001b may comprise (e.g., be made from) a material that may be shaped by a user prior to insertion. The filaments of other embodiments described herein (e.g., FIGS. 3A, 3C, 3D, and 3G-3I) may also be curved. In some embodiments, one filament is curved and one filament is straight.

The curved filaments 1001a, 1001b of FIG. 10 are positioned in planes that include the central longitudinal axis 223. In other embodiments, the filaments 1001a, 1001b may be curved in other directions, such as in a corkscrew arrangement. This may be beneficial to assist the filaments in remaining anchored to the tissue during delivery of RF energy. The curved filaments 1001a, 1001b of FIG. 10 may be operable to produce a lesion that is flatter in a plane perpendicular to the central longitudinal axis 223 than, for example, the straight filaments 206a, 206b of FIG. 6.

In the embodiment illustrated in FIGS. 2A and 2B, the filaments 206a, 206b are illustrated as running the entire length of the elongate member 203 from the filament hub 221 to the tip 201. In some embodiments, a single member may run along at least part of the elongate member 203 and the filaments 206a, 206b may be interconnected to the single member at a point proximal to the tip 201.

The illustrated embodiments show all of the filaments of a given embodiment as commonly deployed or retracted. In some embodiments, one or more filaments may be individually deployed and/or retracted. In some embodiments, a plurality of filaments may exit from the tip at a common location and form a fan-like arrangement as they are deployed.

Deployment of filaments discussed herein has been described as movement of the filaments relative to a stationary tip. In some embodiments, the filaments may be deployed by pulling the tip back relative to the filaments (e.g., movement of the tip relative to stationary filaments). Movement of the tip rather than the filaments may be advantageous, for example, in embodiments in which the needle is initially advanced until in contact with bone to ensure proper positioning relative to target tissue, and then the tip may be retracted, leaving the filaments (e.g., curved shape memory filaments) in a precise, known position. In some embodiments, the filaments may be deployed by advancing the filaments and retracting the tip.

Referring again to FIGS. 2A and 2B, the hub 204 may be fixedly attached to the elongate member 203. The hub 204 may be the primary portion of the needle 103 gripped by the user during insertion and manipulation of the needle 103. The hub 204 may include an asymmetric feature, such as an indicator 225, that is in a known orientation relative to the asymmetry of the tip 201. In this regard, the indicator 225 may be used to communicate to the user the orientation of the tip 201 within a patient. For example, in the embodiment illustrated in FIG. 2A, the indicator 225 is fixed at an orientation circumferentially opposite to the filament slots 304a, 304b. Internally, the hub 204 may include a cavity 213 sized to house a longitudinal protrusion 218 of the actuator 216. The hub 204 may include a hole through which a projection 215 may project into the interior of the cavity 213 to control the motion of the actuator 216 relative to the hub 204 and to secure the actuator 216 to the hub 204. The hub 204 may comprise (e.g., be made from) any appropriate material (e.g., a thermoset plastic, Makrolon® 2548, available from Bayer).

The actuator 216 may be used to control the motion to deploy and/or retract the filaments 206a, 206b. The actuator 216 is operable to move relative to the hub 204, the elongate member 203, and the tip 201 (e.g., parallel to the central longitudinal axis 223). The actuator 216 includes the longitudinal protrusion 218 extending into the cavity 213 of the hub 204. The outer surface of the longitudinal protrusion 218 includes a helical track 219 sized to accommodate the projection 215. In this regard, as the actuator is rotated relative to the hub 204 (e.g., by a user to deploy the filaments 206a, 206b), the helical track 219 and the projection 215 combine to cause the actuator 216 to move longitudinally (e.g., parallel to the central longitudinal axis 223). The actuator 216 comprises an interface portion 217 that may be gripped by a user when rotating the actuator 216. The interface portion 217 may be knurled or otherwise textured to enhance the user's ability to rotate the actuator 216. The hub 204 may also include a textured or shaped feature (e.g., the indicator 225) configured to enhance the user's ability to rotate the actuator 216 relative to the hub 204. The longitudinal protrusion 218 of the actuator 216 may include an inner cavity 226 sized to accept a filament hub 221 and to allow the filament hub 221 to rotate freely relative to the actuator 216. In this regard, the linear motion of the actuator 216 may be transmitted to the filament hub 221 while the rotational motion of the actuator 216 may not be transmitted to the filament hub 221.

The actuator 216 may include a Luer fitting 220 or any other appropriate fitting type on a proximal end thereof. The Luer fitting 220 may be in fluid communication with the lumen 222 and provide a connection such that fluid may be delivered into the lumen 222 and to the fluid port 210 of the tip 201, 211. The Luer fitting 220 may also be configured to allow for the insertion of the RF probe 401 into the lumen 222. The actuator 216 may comprise any appropriate material (e.g., Pro-fax 6523 polypropylene homopolymer, available from LyondellBasell Industries).

The filaments 206a, 206b may be fixedly interconnected to the filament hub 221. In this regard, the longitudinal movement of the filament hub 221 due to the actuator 216 may be communicated to the filaments 206a, 206b to deploy and retract the filaments 206a, 206b upon rotation of the actuator 216. The filament hub 221 may comprise any appropriate material (e.g., Pro-fax 6523 polypropylene homopolymer, available from LyondellBasell Industries).

The user can deploy or retract the filaments 206a, 206b by twisting or rotating the actuator 216. For example, as illustrated, a counterclockwise (as seen from the viewpoint of FIG. 5) rotation of the actuator 216 relative to the hub 204 will result in the deployment (extension) of the filaments 206a, 206b, while a clockwise rotation of the actuator 216 relative to the hub 204 will result in the retraction of the filaments 206a, 206b.

The filaments 206a, 206b may be partially deployed or retracted by partially rotating the actuator 216 relative to the hub 204. The actuator 216 and/or the hub 204 may include markings to indicate the position of the filaments 206a, 206b (e.g., the depth or extent of deployment). The actuator 216 and/or the hub 204 may include detents to provide audible and/or tactile feedback of the position of the filaments 206a, 206b.

In some embodiments, the filaments may be deployed at the user's discretion to a deployed position proximal to, at, or distal to a plane perpendicular or transverse to the central longitudinal axis 223 at the point 301, 312. For example, in some embodiments, full (e.g., 3/3) rotation of the actuator 216 may deploy the filaments in a fully deployed position that is distal to a plane perpendicular or transverse to the central longitudinal axis 223 at the point 301, 312, partial (e.g., ⅔) rotation of the actuator 216 may deploy the filaments in a partially deployed position that is at a plane perpendicular or transverse to the central longitudinal axis 223 at the point 301, 312, and partial (e.g., ⅓) rotation of the actuator 216 may deploy the filaments in a partially deployed position that is proximal to a plane perpendicular or transverse to the central longitudinal axis 223 at the point 301, 312. The actuator 216 and/or the hub 204 may include features such as stops or detents to provide audible and/or tactile feedback regarding the extent of deployment (e.g., at 0/3, ⅓, ⅔, and 3/3) and/or the position of the filaments 206a, 206b (e.g., fully retracted, ⅓ deployed, ⅔ deployed, and fully deployed). Other fractions are also possible, including fractions at uneven intervals (e.g., a combination of ⅓, ½, and ⅘). In certain embodiments, selectable controlled partial deployment allows for controlled adaptation of the lesion to any particular shape and/or conformance of the filaments to a specific anatomy (e.g., boney anatomy).

FIGS. 17A-17E illustrate components of the mechanism at the proximal end 205 of the needle 103 of FIG. 2D. The mechanism may also be used, for example, with the needle 103 of FIG. 2A and other needles described herein. The components described with respect to FIGS. 17A-17E may include features described herein with respect to FIGS. 2B and 2C, and the components described herein, for example with respect to FIGS. 2B and 2C may include features described herein with respect to FIGS. 17A-17E. Combinations of components are also possible.

Figure 17A:
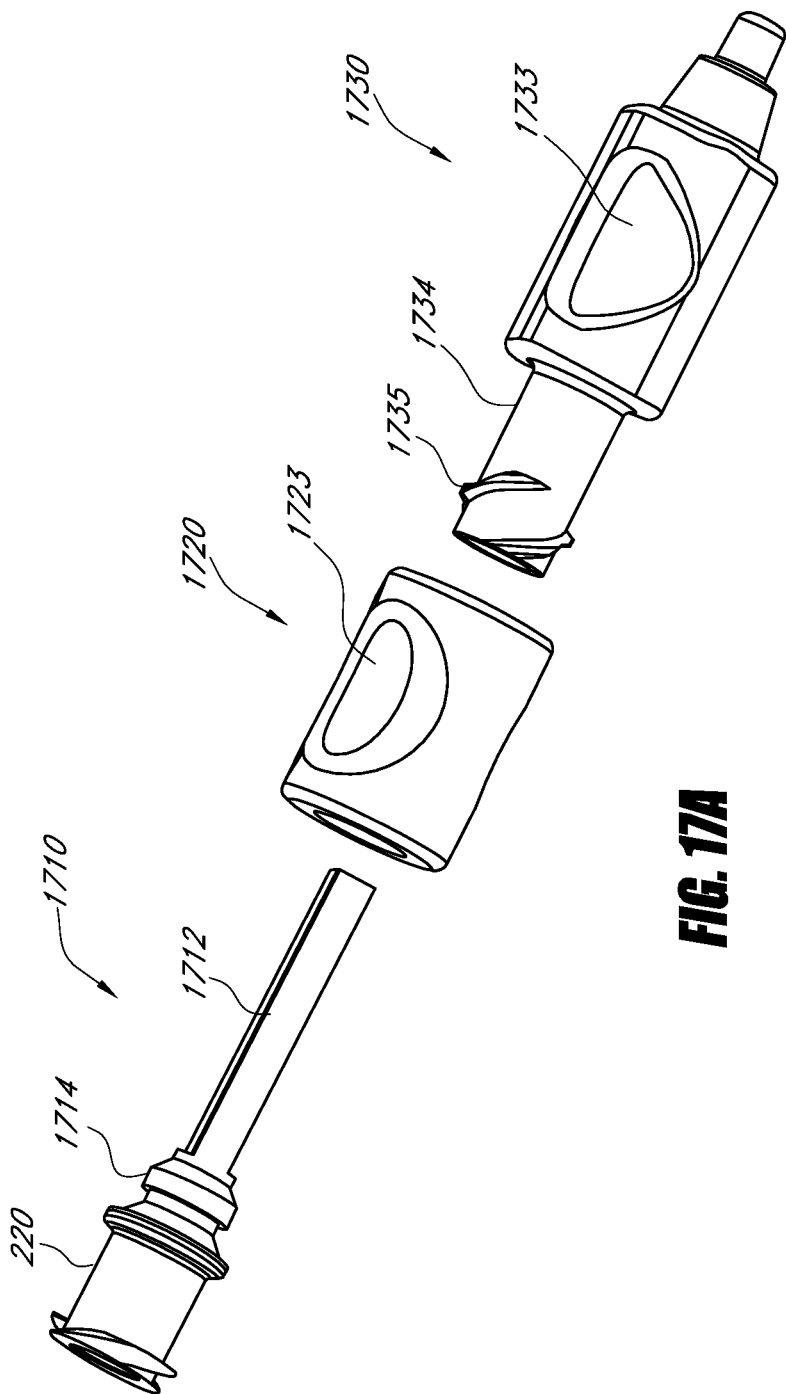
FIG. 17A is an exploded view of components of the deployment mechanism of FIG. 2D.
Figure 17B:
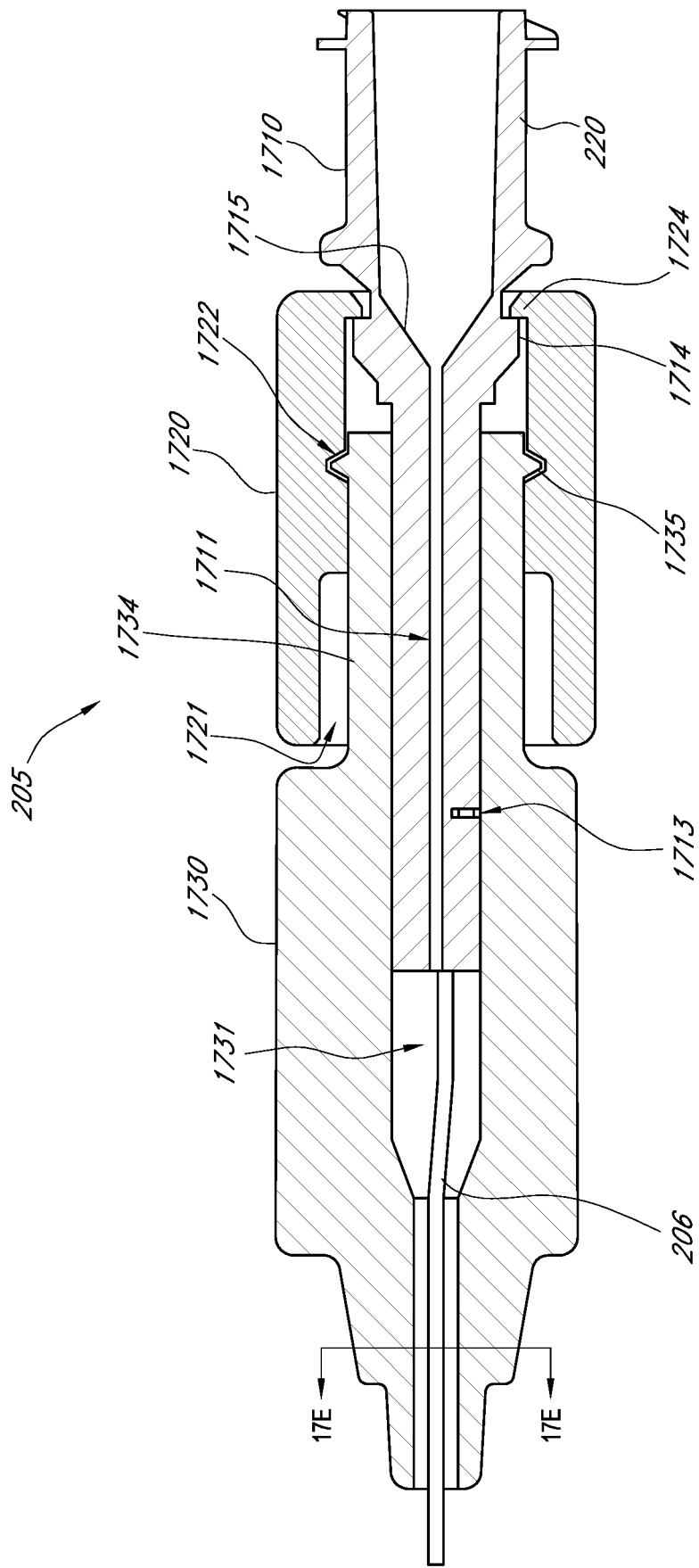
FIG. 17B is a cross-sectional view of components of the deployment mechanism of FIG. 2D.

FIG. 17A is an exploded view of components of the deployment mechanism of FIG. 2D. The mechanism comprises an advancing hub or slide member 1710, a spin collar or actuator 1720, and a main hub 1730. FIG. 17B is a cross-sectional view of the advancing hub 1710, the spin collar 1720, and the main hub 1730 assembled together, as well as half of the wire 206 illustrated in FIG. 2E. The advancing hub 1710 includes a stem or longitudinal protrusion 1712. The spin collar 1720 includes a lumen 1721 extending from the proximal end to the distal end. The main hub 1730 includes a lumen 1731 extending from the proximal end to the distal end. When assembled, the stem 1712 of the advancing hub 1710 is in the lumen 1721 of the spin collar 1720 and in the lumen 1731 of the main hub 1730. The advancing hub 1710 may include an annular protrusion 1714 that may interact with an annular protrusion of the spin collar 1720 (e.g., the annular protrusion 1714 having a larger diameter than the annular protrusion 1724) to inhibit the stem 1712 from exiting the proximal end of the lumen 1721. In some embodiments, the annular protrusions 1714, 1724 include tapered surfaces that may interact to allow insertion of the stem 1712 and the annular protrusion 1714 into the lumen 1721 and perpendicular surfaces to inhibit the annular protrusion 1714 and the stem 1712 from exiting the proximal end of the lumen 1721. The main hub 1730 includes a stem or longitudinal protrusion 1734. When assembled, the stem 1734 of the main hub 1730 is in the lumen 1721 of the spin collar 1720. Other interactions between the advancing hub 1710, the spin collar 1720, and the main hub 1730 are described herein, for example with respect to FIGS. 17C-17E.

Figure 17C:
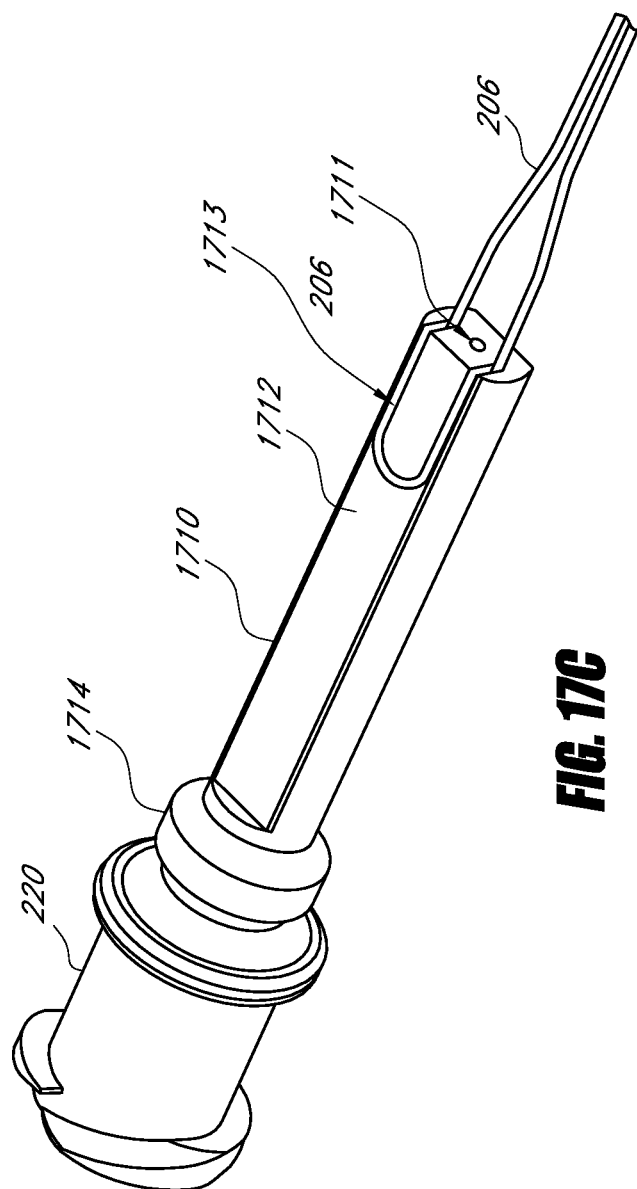
FIG. 17C is a perspective view of an example embodiment of an advancing hub and the wire of FIG. 2E.

FIG. 17C is a perspective view of an example embodiment of the advancing hub 1710 and the wire 206 of FIG. 2E. The stem 1712 of the advancing hub 1710 comprises a U-shaped recess 1713 configured to interact with the bent proximal portion of the wire 206. Other shapes of the recess 1713 are also possible (e.g., V-shaped). The recess 1713 may complement the shape of the proximal end of the wire 206. In some embodiments, the width of the recess 1713 is slightly smaller (e.g., about 0.001 inches (approx. about 0.025 mm) smaller) than the diameter of the wire 206 such that after being press-fit, the wire 206 is fixedly interconnected to the advancing hub 1710.

In some embodiments, the stem 1712 is shaped as illustrated in FIG. 17C, including a perpendicular or transverse cross-section that includes flat surfaces (e.g., the surface comprising the top of the recess 1713) and arcuate surfaces, for example an ellipse with squared ends. The lumen 1731 of the main hub 1730 may comprise complementary surfaces, for example in a wider proximal portion, such that when the stem 1712 is in the lumen 1731, the advancing hub 1710 is in a fixed rotational position relative to the main hub 1710. Other shapes and rotational fixation configurations are also possible.

The proximal end of the advancing hub 1710 comprises a fitting 220 (e.g., a Luer fitting or any other appropriate fitting). When assembled, the fitting 220 is proximal to the spin collar 1720. The advancing hub 1710 comprises a lumen 1711 extending from the proximal end to the distal end. A fluid delivery device such as a syringe may be attached to the fitting 220 to deliver fluid through the lumen 1711 and then through the lumen 1731 of the main hub, the lumen 308 of the elongate member 203, the lumen 306c of the tip 211, and out the fluid port 210 of the tip 211. The RF probe 401 may be inserted into the lumen 1711, then into the lumen 1731 of the main hub, then into the lumen 308 of the elongate member 203, then into the lumen 306c of the tip 211. The RF probe 401 may include a fitting configured to interact with the fitting 220. The lumen 1711 may include a wide diameter portion in the area of the fitting 220 and a narrow diameter portion in the area of the stem 1712, and a tapered surface 1715 transitioning from the wide diameter portion to the narrow diameter portion. The tapered surface 1715 may help direct fluid and/or an RF probe 401 into the narrow diameter portion. In some embodiments, the narrow diameter portion of the lumen 1711 has a diameter between about 0.005 inches and about 0.05 inches (approx. between about 0.13 mm and about 1.3 mm), between about 0.01 inches and about 0.03 inches (approx. between about 0.25 mm and about 0.76 mm), between about 0.015 inches and about 0.025 inches (approx. between about 0.38 mm and about 0.64 mm) (e.g., about 0.02 inches (approx. about 0.5 mm)), combinations thereof, and the like. In some embodiments, the narrow diameter portion of the lumen 1711 has a diameter that is no larger than the diameter of any other lumen of the needle 103 such that fluid pressure will default to the distal end of the needle 103. For example, the narrow diameter portion of the lumen 1711 may have a diameter of about 0.02 inches (approx. about 0.5 mm), the narrow diameter portion of the lumen 1731 may have a diameter of about 0.05 inches (approx. about 1.3 mm), the lumen 308 of the elongate member 203 may have a diameter of about 0.05 inches (approx. about 1.3 mm), and the lumen 306c may have a width of about 0.02 inches (approx. about 0.5 mm). In some embodiments, the lumen 306c may be slightly smaller than the narrow diameter portion of the lumen 1711 and have the same effect, for example due to small losses of fluid through the lumens 306a, 306b and out the filament ports 304a, 304b, which may be acceptable because anesthesia and dye, for example, may permeate through fluid and proximate to the filament ports 304a, 304b even if substantially only dispensed from the fluid port 210. In some embodiments, the advancing hub 1710 comprises a polymer (e.g., Pro-fax 6523 polypropylene homopolymer, available from LyondellBasell Industries).

Figure 17D:
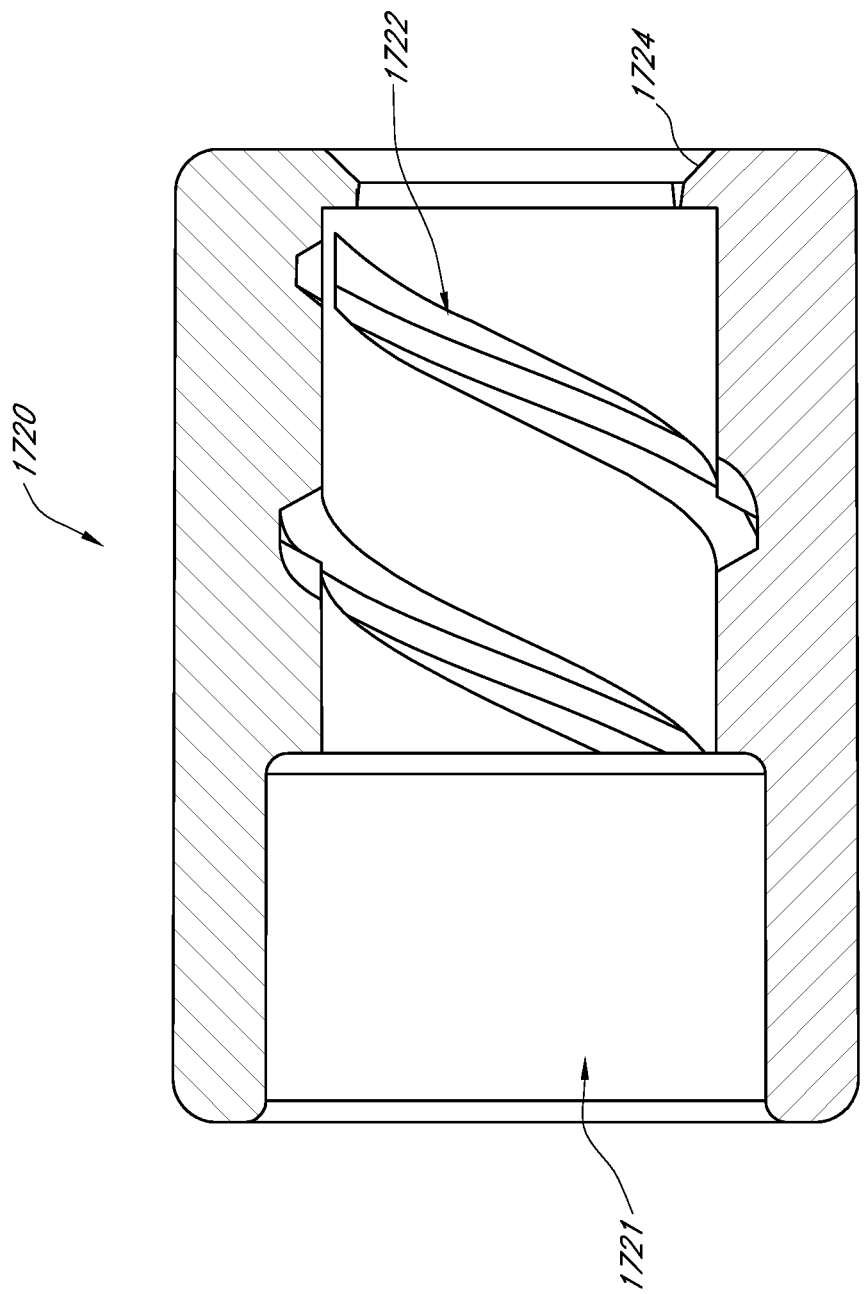
FIG. 17D is a cross-sectional view of an example embodiment of a spin collar.

FIG. 17D is a cross-sectional view of an example embodiment of a spin collar 1720. The cross-section is along the same line as in FIG. 17B, but further features are visible because not blocked by the advancing hub 1710 or the main hub 1730. As illustrated in FIG. 17B, the lumen 1721 is configured to at least partially contain the stem 1712 and the stem 1734, and not to contact fluid or an RF probe 401. The lumen 1721 comprises a helical track 1722 sized to interact with a corresponding helical thread 1735 (FIG. 17A) on the stem 1734 of the main hub 1730. As the spin collar 1720 is rotated relative to the main hub 1730 (e.g., by a user stabilizing the needle and gripping the main hub 1730 with the non-dominant hand and manipulating the spin collar 1720 with the dominant hand), for example, to deploy the filaments 206a, 206b, the helical track 1722 and the helical thread 1735 interact to cause the spin collar 1720 and the advancing hub 1710 to move longitudinally parallel to the central longitudinal axis 223. In this regard, a linear motion of the advancing hub 1710 relative to the main hub 1730 may be created while the rotational motion of the spin collar 1720 may not be transmitted to the advancing hub 1710 and the main hub 1730. In some embodiments, between about 1.25 turns and about 1.5 turns of the spin collar 1720 fully deploys the filaments 206a, 206b. In some embodiments, between about 0.75 turns and about 1.25 turns (e.g., one 360° rotation) of the spin collar 1720 fully deploys the filaments 206a, 206b. The configuration of the helical track 1722 and the helical thread 1735 may be adjusted to provide varying levels of filament deployment with varying levels of rotation of the spin collar 1720. An outer surface of the spin collar 1720 may be textured or include features 1723 to assist the user in gripping and twisting or rotating the spin collar 1720 relative to the main hub 1730. In some embodiments, the spin collar comprises the helical thread 1735 and the main hub 1730 comprises the helical track 1722. In some embodiments, the spin collar 1720 comprises a polymer (e.g., Pro-fax 6523 polypropylene homopolymer, available from LyondellBasell Industries).

Figure 17E:
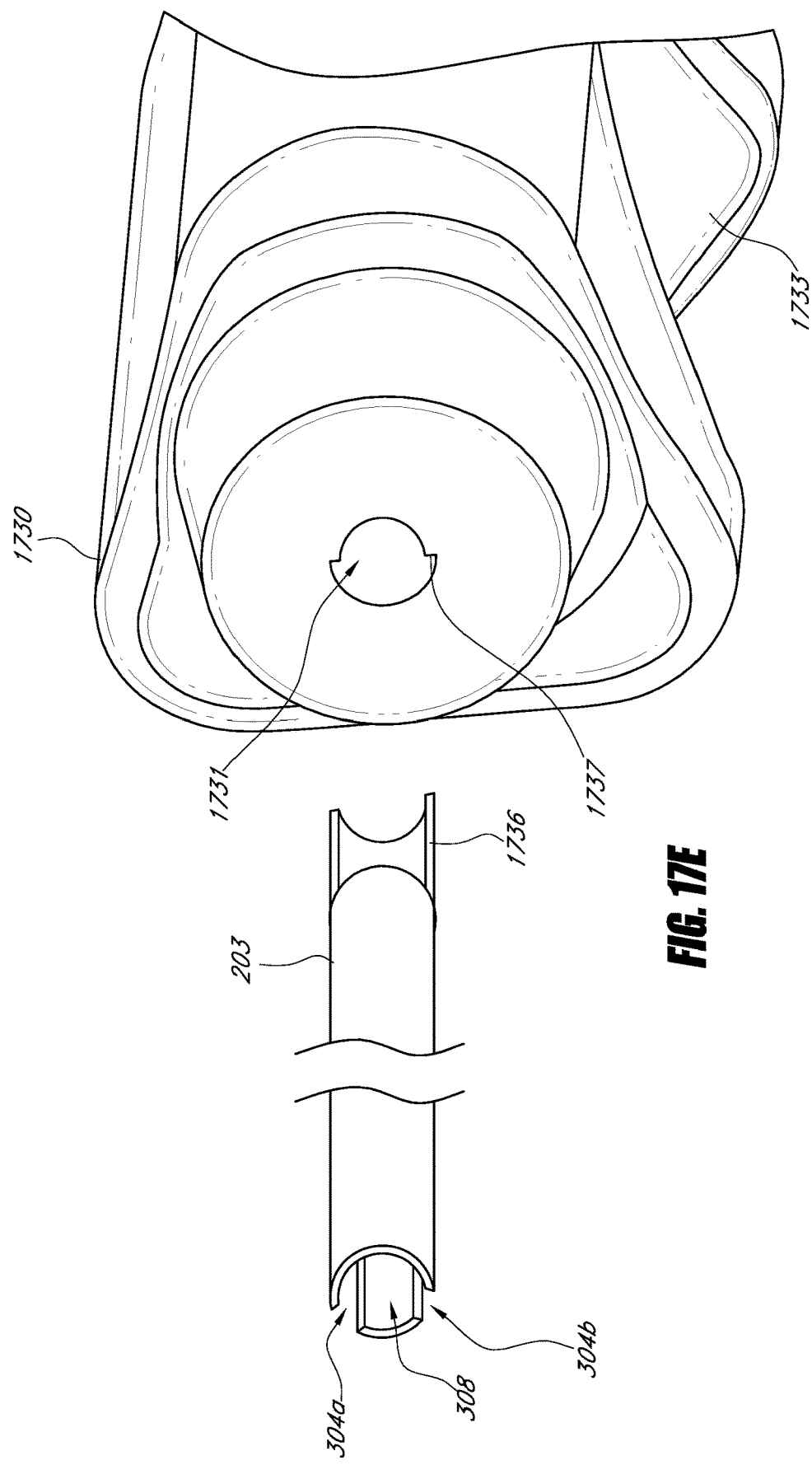
FIG. 17E is a cross-sectional view of an example embodiment of a main hub, taken along the line 17E-17E of FIG. 17B, in exploded view with an example embodiment of an elongate member.

FIG. 17E is a cross-sectional view of an example embodiment of the main hub 1730, taken along the line 17E-17E of FIG. 17B, in exploded view with an example embodiment of an elongate member 203. The proximal end of the elongate member 203, to the right in FIG. 17E, includes a partial circumferential portion 1736. The distal end lumen 1731 of the main hub 1730 includes a complementary partial circumferential portion 1737. The partial circumferential portions 1736, 1737 can cause the elongate member 203 to be in a fixed and known rotational orientation with the main hub 1730, for example after assembly because the relative position of the indicator 1733 and the partial circumferential portion 1737 is known. For example, the distal end of the elongate member 203, to the left in FIG. 17E, includes the filament ports 304a, 304b on the same side as the partial circumferential portion 1736. Other partial circumferential portions and other complementary shapes are also possible. For example, the partial circumferential portions may comprise interlocking teeth. In some embodiments, the thickness of the partial circumferential portion 1737 is substantially the same as the thickness of the walls of the elongate member 1736 to provide a smooth transition between the lumen 1731 and the lumen 308. In some embodiments, the main hub 1730 comprises clear polycarbonate (e.g., thermoset plastic such as Makrolon® 2548, available from Bayer). In some embodiments, the elongate member comprises a hypotube (e.g., comprising 300 Series Stainless Steel) with features such as the filament ports 304a, 304b and the partial circumferential portion 1736 cut out (e.g., by laser, mechanical, chemical, or other cutting methods).

Other types of mechanisms may be used to control deployment and retraction of the filaments. For example, in some embodiments, the mechanism includes a spring configured to bias the filaments 206a, 206b toward a predetermined position (e.g., fully deployed, fully retracted), analogous to a spring loaded mechanism used in retractable ballpoint pens. For another example, the mechanism may include a roller wheel, for example incorporated into the hub 204, that would advance or retract the filaments 206a, 206b upon rotation, for example with a user's thumb. For yet another example, the hub 204 and the actuator 216 may interact via complimentary threaded features. As the actuator 216 is threaded into the hub 204, the filaments 206a, 206b would advance, and as the actuator 216 is threaded out of the hub 204, the filaments 206a, 206b would retract. For still another example, a Touhy-Borst type mechanism could be incorporated to control the deployment and retraction of the filaments 206a, 206b. Any other appropriate mechanism for controlling linear motion of the filaments 206a, 206b may be incorporated into the needle 103. Any of the mechanisms described herein may be used for controlling deployment and retraction of the filaments of any of the embodiments described herein. For example, the mechanisms illustrated in FIGS. 2A-2D and 17A-17E may be used to deploy and retract the filaments in FIGS. 3A, 3C, 3D, 3G-3I, and 5-10.

FIG. 2C is a partial cut away and partial cross-sectional view of a portion of an alternate embodiment of a mechanism 230 comprising a hub 231 and actuator 232 that may be part of a needle 103 used in an RF neurotomy procedure. The hub 231 may be fixedly attached to the elongate member 203. The hub 231 may be the primary portion of the needle 103 gripped by the user during insertion and manipulation of the needle 103. The hub 231 may include an asymmetric feature, such as an indicator 233, that is in an known orientation relative to the asymmetry of the tip 201. In this regard, the indicator 233 may be used to communicate to the user the orientation of the tip 201 within a patient. Internally, the hub 231 may include a cavity 234 sized to house a longitudinal protrusion 235 of a slide member 236. The longitudinal protrusion 235 may include a keyway or key slot 237 that may run along a longitudinal direction of the longitudinal protrusion 235. The internal surface of the hub 231 through which the longitudinal protrusion 235 moves may include a mating key (not shown) configured to fit and slide in the key slot 237. Together, the key slot 237 and mating key of the hub 231 may limit the slide member 236 to a linear motion parallel to the central longitudinal axis 223.

The filaments 206a, 206b may be fixedly connected to the longitudinal protrusion 235 of the slide member 236 for longitudinal movement therewith. In this regard, distal movement (e.g., movement to the right as shown in FIG. 2C) of the longitudinal protrusion 235 relative to the hub 231 may cause extension of the filaments 206a, 206b relative to the hub 231, the elongate member 203, and the tip 201. For example, distal movement of the longitudinal protrusion 235 may move the filaments 206a, 206b from a retracted position to a deployed position. For another example, proximal movement (e.g., movement to the left as shown in FIG. 2C) of the longitudinal protrusion 235 relative to the hub 231 may result in retraction of the filaments 206a, 206b relative to the hub 231, the elongate member 203, and the tip 201.

The hub 231 may be made from any appropriate material (e.g., a thermoset plastic, Makrolon® 2548, available from Bayer). The hub 231 may be at least partially transparent such that the position of the longitudinal protrusion 235 and/or other components of the hub 231 may be observable by a user. The hub 231 may further include demarcations (e.g., molded or printed marks) such that the amount of extension of the filaments 206a, 206b may be determined from the position of the longitudinal protrusion 235 and/or other components relative to the demarcations.

An actuator 232 may be used to control the motion to deploy and/or retract the filaments 206a, 206b fixedly connected to the longitudinal protrusion 235. The actuator 232 may be generally tubular such that it fits around a longitudinal hub projection 238 projecting from the proximal end of the hub 231. At least a portion of the cavity 234 may be in the longitudinal hub projection 238. The actuator 232 may also include an annular feature 239 configured to fit in an annular slot 240 in the slide member 236. The annular feature 239 may be sized relative to the annular slot 240 such that the actuator 232 may rotate relative to the slide member 236 about the central longitudinal axis 223 or an axis parallel thereto while the position of the actuator 232 relative to the slide member 236 along the central longitudinal axis 223 remains fixed. In this regard, the actuator 232 and the slide member 236 may be configured to move in tandem relation along the central longitudinal axis 223. The annular feature 239 and annular slot 240 may be configured such that, during assembly, the actuator 232 may be pressed onto the slide member 236 and the annular feature 239 may snap into the annular slot 240.

The inner surface of the actuator 232 may include a helical track 241 sized to accommodate a corresponding mating helical thread 242 on the longitudinal hub projection 238. In this regard, as the actuator 232 is rotated relative to the slide member 236 and the hub 231 (e.g., by a user to deploy the filaments 206a, 206b), the helical track 241 and the helical thread 242 interact to cause the actuator 232 and the slide member 236 to move longitudinally along the central longitudinal axis 223. In this regard, a linear motion of the slide member 236 relative to the hub 231 may be created while the rotational motion of the actuator 232 may not be transmitted to the slide member 236 and the hub 231. An outer surface of the actuator 232 may be textured or include features to assist the user in gripping and twisting or rotating the actuator 232 relative to the hub 231. In some embodiments, the longitudinal hub projection 238 comprises the helical track 241 and the inner surface of the actuator 232 comprises the helical thread 242.

The proximal end of the slide member 236 may include a Luer fitting 243 or any other appropriate fitting type. The Luer fitting 243 may be in fluid communication with a lumen passing through the slide member 236 and may provide a connection such that fluid may be delivered through the Luer fitting 243 and into the lumen of the slide member 236. In turn, the lumen of the slide member 236 may be in fluid communication with the cavity 234 of the hub 231, which may in turn be in fluid communication with a lumen in the elongate member 223 (e.g., the lumen 222). The lumen in the elongate member 223 may be in fluid communication with the tip 201 (e.g., the fluid port 210). In this regard, fluid may flow into the Luer fitting 243, into and through the lumen in the slide member 236, into and through the cavity 234 of the hub 231, into and through the elongate member 223, and out from fluid portion 210 of the tip 201. The Luer fitting 243, the lumen in the slide member 236, the cavity 234 of the hub 231, and the lumen of the elongate member 223 may all also be configured to allow for the insertion of the RF probe 401 therethrough. The protrusion 235 and the cavity 234 of the longitudinal hub projection 238 may be sized and/or configured to form a fluid seal therebetween, allowing fluid delivered under pressure through the Luer fitting 220 to flow through the cavity 238 and into the elongate member 203 substantially without leaking past the interface between the protrusion 235 and the cavity 234 of the longitudinal hub projection 238.

As described herein, the filaments 206a, 206b may be fixedly interconnected to the slide member 236. Axial movement of the slide member 236 due to the actuator 232 may be thereby communicated to the filaments 206a, 206b to deploy and retract the filaments 206a, 206b upon rotation of the actuator 232. The slide member 236 may be made from any appropriate material (e.g., Pro-fax 6523 polypropylene homopolymer, available from LyondellBasell Industries). The actuator 232 may be made from any appropriate material (e.g., Pro-fax 6523 polypropylene homopolymer, available from LyondellBasell Industries).

The user can deploy or retract the filaments 206a, 206b by twisting or rotating the actuator 232. By partially rotating the actuator 232 relative to the hub 231, the filaments 206a, 206b may be partially deployed or retracted. The actuator 232 and/or hub 231 may include detents to provide audible and/or tactile feedback of the position of the filaments 206a, 206b. The detents may be configured such that audible and/or tactile feedback associated with engagement of a detent coincides with a predetermined amount of deployment or retraction of the filaments 206a, 206b, as described herein. In this regard, such audible and/or tactile feedback may be used in determining filament position.

In some embodiments, the needle 103 is a multipolar (e.g., bipolar) device in contrast to the monopolar devices described herein. In certain such embodiments, the filaments are isolated from each other and/or from the tip to enable bipolar operation (e.g., the filaments having one polarity and the tip having a second polarity, one filament having one polarity and one filament and the tip having a second polarity, one filament having one polarity and one filament having a second polarity, etc.). In embodiments in which the needle 103 comprises more than two filaments, elements may be included to allow for selection of the polarity of the certain filaments to aid in lesion shape, size, and/or position control. In some embodiments, the needle 103 may be used in either a monopolar mode or in a bipolar mode as selected by the user. For example, RF probes 401 may include shapes, insulating features, etc. configured to produce monopolarity or bipolarity.

The herein-described embodiments of needles may be used in spinal RF neurotomy procedures, which will now be described. In general, for an RF neurotomy procedure, the patient may lie face down on a table so that the spine of the patient is accessible to the user. At any appropriate time before, during, and/or after the procedure, the user may use imaging equipment, such a fluoroscope, to visualize the patient's anatomy and/or to visualize the positioning of equipment (e.g., the needle relative to a target volume).

The patient may be administered sedatives and/or intravenous fluids as appropriate. The skin of the patient surrounding the procedure location may be prepared and maintained using an appropriate sterile technique. In embodiments in which the needle is monopolar, a return electrode pad 104 may be attached to the patient. A local anesthetic may be injected subcutaneously where the needle will be inserted or along the approximate path of the needle, for example through the needle itself or through a different needle.

With the filaments in the retracted position, the needle may be introduced into the patient and moved to a target position relative to a target portion of a target nerve or to a target position relative to a target volume in which the target nerve is likely situated (all of which are generally referred to herein as the target nerve or portion of the target nerve). The target nerve may be an afferent nociceptive nerve such as, for example, a medial branch nerve proximate a lumbar facet joint. Introduction of the needle into the patient may include percutaneously using the tip of the needle to pierce the skin of the patient. The moving of the needle may include navigating toward the target position using fluoroscopic guidance. Furthermore, the moving of the needle may include advancing the needle to an intermediate position and then repositioning the needle to the target position. For example, the needle may be advanced until it contacts a bone or other structure to achieve the intermediate position. This may be followed by retracting the needle a predetermined distance to achieve the target position. Such a procedure may be facilitated by the markers 224 or collar discussed herein.

During the moving of the needle or after the target position has been achieved, the needle may be used to inject an anesthetic and/or a dye proximate to the target nerve. The dye may increase contrast in fluoroscopic images to assist in visualizing the patient's anatomy, which may aid the user in guiding and/or verifying the position of the needle.

The needle may be rotated about the central longitudinal axis of the elongate member of the needle to achieve a desired orientation relative to the target nerve. For example, the needle may be rotated such that a lesion created with the needle with the filaments deployed will be offset from the central longitudinal axis toward the target nerve. Such rotation of the needle may be performed prior to insertion of the needle into the patient and/or after insertion into the patient. For example, the user may rotate the needle prior to insertion such that the needle is generally in the desired rotational orientation. Then, after achieving the target position, the user may fine tune the rotational orientation of the needle by rotating the needle to a more precise orientation. As described herein, the hub or another portion of the needle outside the patient's body may indicate the rotational orientation of the needle.

Once the target position and desired rotational orientation have been achieved, the next step may be to advance one or more filaments of the needle relative to the tip of the needle. The particular needle used for a procedure may have been selected to enable the creation of a particular sized and shaped lesion at a particular position relative to the needle. The particular needle used may be of any appropriate configuration discussed herein (e.g., any appropriate number of filaments, any appropriate filament positioning, monopolar or bipolar, any appropriate deployment and retraction mechanism, etc.).

In embodiments in which the needle is configured as illustrated in FIGS. 5 and 6 (e.g., about 120° apart), the advancement of filaments may include advancing the filaments such that when the filaments are in their respective deployed positions, a midpoint between a distal end of the first filament and a distal end of the second filament is offset from the central longitudinal axis of the needle, and the filament endpoints are distal to the tip of the needle. Such deployment may enable the needle to be used to create a lesion that is offset from the tip of the needle toward the midpoint between the deployed filament ends. The lesion created may also be positioned at least partially distal to the tip of the needle.

Figure 11A:
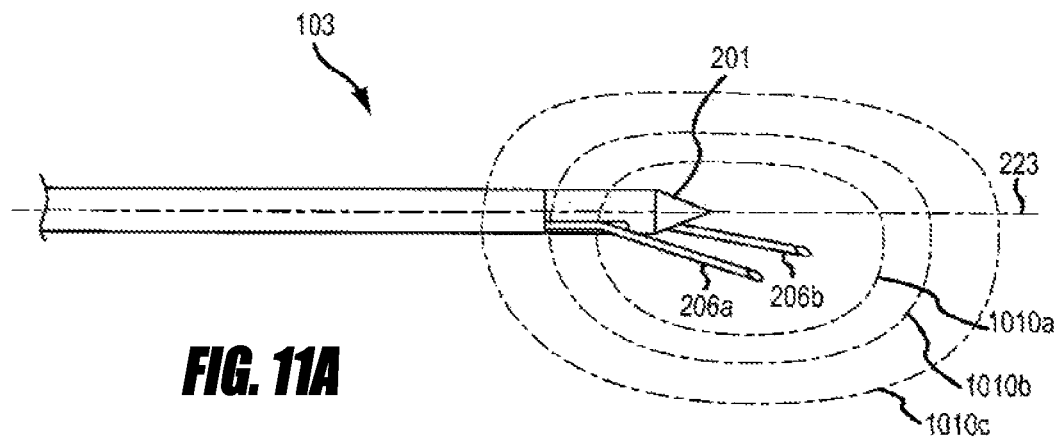
FIG. 11A is an illustration of an example set of isotherms that may be created with the needle of FIG. 2A.

FIG. 11A is an illustration of an example set of isotherms 1010a-1010c that may be created with the needle 103 of FIG. 2A. As illustrated by the set of isotherms 1010a-1010c, RF energy emanating from the tip 201 and from the filaments 206a, 206b, may produce a region of elevated temperature about the tip 201 and the filaments 206a, 206b. The isotherms 1010a-1010c may be offset from the central longitudinal axis 223 such that a centroid of the isotherms as viewed in FIG. 11A is offset from the central longitudinal axis 223 in the direction of the filaments 206a, 206b. The centroid of the isotherms 1010a-1010c as viewed in FIG. 11A may also be distal relative to the tip 201 and between the tip 201 and the distal ends of the deployed filaments 206a, 206b. The isotherms 1010a-1010c may also be shaped such that, as viewed in FIG. 11A, the isotherms 1010a-1010c have a maximum cross-sectional dimension along the central longitudinal axis 223 that is greater than a maximum cross dimension in the plane of FIG. 11A perpendicular to the central longitudinal axis 223. As visible in the illustrated orientation of FIG. 11B, the isotherms 1010a-1010c may have a maximum cross-sectional dimension along the central longitudinal axis 223 that is greater than a maximum cross-sectional dimension perpendicular to the plane of FIG. 11A and perpendicular to the central longitudinal axis 223.

The offset of the centroid of the isotherms 1010a-1010c from the central longitudinal axis 223 may result in greater lesion width in a plane perpendicular to the central longitudinal axis 223, as compared to a similarly-sized straight needle with no filaments. The offset of the centroid of the isotherms 1010a-1010c may also allow for projection of the centroid of a corresponding lesion volume in a direction away from the central longitudinal axis 223. By way of example, such offsets may advantageously enable the execution of the example procedures described herein. Such offsets may advantageously enable the creation of lesion volumes distal (relative to the needle 103) to potentially interfering structures (e.g., an ossified process). Such offsets may advantageously enable the needle 103 to be inserted into a patient at a more desirable angle (e.g., closer to perpendicular to the surface of the patient such as within 30° of perpendicular to the surface of the patient), at a more desirable piercing location, and/or through more desirable tissue than may be attempted using a needle without offset lesion capabilities.

Figure 11B:
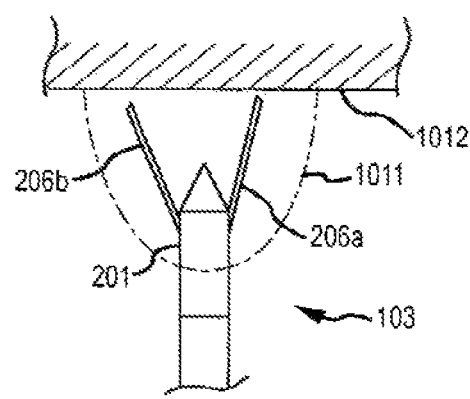
FIG. 11B is an illustration of an example lesion that may be created with the needle of FIG. 2A.

FIG. 11B is an illustration of an example lesion 1011 that may be created with the needle 103 of FIG. 2A. In FIG. 11B, the needle 103 has been placed perpendicular to a surface 1012. The surface 1012 may, for example, be the surface of a bone, such as a lumbar vertebra. As illustrated, the filaments 206a, 206b are deployed such they are proximate to the surface 1012. In some embodiments, contact with the surface 1012 might undesirably deform the filaments 206a, 206b, but such contact may be avoided, for example by the needle advancement and retraction procedures described herein. The lesion 1011 has a width along the surface 1012 that is wider than would be created by the needle 103 if the filaments 206a, 206b were not deployed. Such capabilities may, for example, be advantageous where a target structure (e.g., a nerve) is known to be positioned along the surface 1012, but its exact position is unknown. In such a case, the needle 103 may be positioned generally perpendicular to the surface 1012 to achieve the illustrated lesion width along the surface 1012, whereas achieve the same lesion width along the surface 1012 using a the needle 103 without the filaments 206a, 206b deployed would require either multiple repositioning steps or placement of the needle 103 generally parallel to the surface 1012.

Figure 11C:
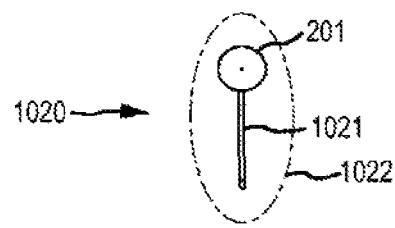
FIG. 11C is an illustration of an example lesion that may be created with a single-filament needle.

FIG. 11C is an illustration of an example lesion 1022 that may be created with a single-filament needle 1020. The single-filament needle 1020 may be similar to the needle 103, although the single-filament needle 1020 includes only a single filament 1021. The filament 1021 may be configured similarly to the filaments 206a, 206b. The single-filament needle 1020 with the filament 1021 deployed may be operable to produce a lesion 1022 that is a flattened version (e.g., thinner in a direction perpendicular to the central longitudinal axis 223, which is the left to right direction as illustrated in FIG. 11C) of a lesion that may be produced by the needle 103 with two filaments 206a, 206b deployed. The capability to produce such a lesion shape may be beneficial when it is desirable to have a relatively large lesion in a particular direction (e.g., to compensate for the variability of location of a target nerve) and a relatively small lesion width in another direction (e.g., to avoid a structure such as viscera or a patient's skin). As described herein, certain embodiments of the needle 103 may allow differential or selective deployment and/or activation of the filaments 206*a*, 206*b* such that the needle 103 may imitate the single-filament needle 1020.

In embodiments in which the needle is configured such that all of the filaments of the needle are deployed on a common side of a central plane of the needle (in which the central longitudinal axis is entirely within the central plane), the advancement of filaments may include advancing the filaments such that when the filaments are in their respective deployed positions, the distal ends of all of the filaments are on a common side of the central plane. Such deployment may enable the needle to be used to create a lesion that is offset from the tip of the needle to the same side of the central plane as the deployed filament ends. The lesion created may also be positioned at least partially distal to the tip of the needle.

In embodiments in which the needle is configured as illustrated in FIG. 7 or 8, the advancement of filaments may include advancing the filaments such that when the filaments are in their respective deployed positions, each filament distal end defines a vertex of a polygon whose centroid is offset from a central longitudinal axis of the needle. Such deployment may enable the needle to be used to create a lesion that is offset from the tip of the needle toward the centroid. The lesion created may also be positioned at least partially distal to the tip of the needle.

The advancement of the filaments may be achieved using any of the mechanisms discussed herein. For example, in the embodiment of FIG. 2A, rotating the actuator 216 relative to the hub 204 may cause the filaments to advance to the deployed position. The advancement of the filaments may be performed such that each of the plurality of filaments passes through a surface of the needle that is parallel to the central longitudinal axis of the needle. In some embodiments, the filaments of the needle may be advanced to a position that is an intermediate position between the retracted position and the fully deployed position. The degree of deployment may be based on the desired lesion size and/or the accuracy of the placement of needle. For example, the same needle may be used in two different procedures where the variability of the location of a target nerve is greater in the first procedure than it is in the second procedure. In such situation, the greater deployment of the filaments may be used in the first procedure, whereas in the second procedure, a smaller degree of deployment may be used since a smaller lesion may suffice to ensure that the target nerve has been ablated. For another example, after placement of the needle during a procedure, the position of the needle may be determined to be slightly offset from a target position. In such a case, the filaments may be deployed to a greater degree than would have been required if the needle were placed exactly on target. In such a case, the greater degree of deployment may be used to compensate for the needle positioning inaccuracy. In such a case, needle repositioning and possible associated trauma may be avoided.

During and/or after advancing the filaments to the deployed position, their positions may be confirmed using an imaging system (e.g., using a fluoroscope). Proper filament positioning may also be verified by using the needle to stimulate the target nerve. For example, an electrical signal (e.g., up to about 2 volts applied at about 2 Hz) may be applied to the needle and the user may observe any related patient movement (e.g., muscle fasciculation in the territory supplied by the nerve). For another example, an electrical signal (e.g., up to about 1 volt applied at about 50 Hz) may be applied to the needle and the patient may indicate if they feel any associated sensations and their locations to assist in verifying correct needle positioning. Such stimulation (user-observed and/or patient reported) may be used to stimulate a targeted nerve to determine if the deployed position is adequate to achieve denervation of the targeted nerve. In this regard, it is desirable for the stimulation to affect the targeted nerve. Upon determination that the target nerve is stimulated, increased energy may be applied to ablate a volume comprising the target nerve.

Such stimulation may also be used to attempt to stimulate a nerve that is not targeted for denervation (e.g., a nerve where no denervation is desired) to determine the position of the needle relative to such a non-targeted nerve. In this regard, if the stimulation signal does not stimulate the non-targeted nerve, the user may determine that the position of the needle relative to the non-targeted nerve is such that the application of ablation energy to the needle will not result in significant damage to (e.g., ablation of) the non-targeted nerve. If the stimulation stimulates the non-targeted nerve (e.g., as determined by user observation and/or patient reporting), the needle may be repositioned to avoid damaging the non-targeted nerve. In this regard, it is desirable for the stimulation not to affect the non-targeted nerve.

After correct needle positioning has been verified (e.g., by imaging and/or stimulation), an anesthetic may be injected through the needle, for example out of at least one of the fluid port 210, 320, the filament ports 304*a*, 304*b*, 318*a*, 318*b*, the lumen 306*c*, etc.

After the filaments have been advanced to the desired position, the next step may be to apply RF energy to the needle using the interconnected RF generator. In embodiments that use a separate RF probe to deliver RF energy, the RF probe may be inserted into a lumen of the needle prior to application of the RF energy. When using such a configuration, the application of RF energy may include applying RF energy to the RF probe and conducting the RF energy away from the probe by the tip and/or filaments.

The resultant RF energy emanating from the tip and/or the filaments may generate heat that ablates the target nerve. Such ablation may be achieved by creating a lesion volume that includes the target nerve. It is desired that the target nerve be completely ablated to prevent incomplete neurotomy which may result in dysesthesia and/or patient discomfort. For example, a lesion with a maximum cross-sectional dimension between about 8 mm and about 10 mm may be created. Larger or smaller lesions may be created by varying filament characteristics (e.g., filament advancement distance) and/or RF energy levels. The created lesion may be offset from the central longitudinal axis of the needle. The center of the lesion may be distal to the tip of the needle. Of note, since the RF energy is emanating from the tip and filaments, a particularly sized lesion may be created with a lower peak temperature (the maximum temperature experienced in the patient) than would be possible if a needle without filaments or without deployed filaments were to be used to create the same-sized lesion. For example, a particular lesion may be achieved with the needle with deployed filaments where the peak temperature is between about 55° C. and about 60° C. or less than about 70° C., whereas creation of the same lesion using a needle without filaments or without deployed filaments could require a peak temperature of about 80° C. Such lower temperature lesions achievable by a needle with deployed filaments may result in greater patient safety and/or procedure tolerance.

Before, during, and/or after the application of RF energy, a temperature sensor (e.g., thermocouple) at or near the tip of the needle may be used to monitor the temperature at or near the tip. Such readings may be used as control signals (e.g., a feedback loop) to control the application of RF energy to the needle. For example, control signals and/or temperature data may be used for closed-loop control of the needle 103 by automatic adjustment of a parameter (e.g., frequency, wattage, and/or application duration of the RF energy, and/or filament deployment length, needle position, etc.) upon detection of a temperature. Feedback loops involving the user are also possible. If it is desired to ablate additional target nerves or to ablate an additional volume to ensure ablation of the original target nerve, the spinal RF neurotomy procedure may continue. In some embodiments, the distal end 402 of the RF probe 401 is a dual-purpose wire that can deliver RF energy to the tip and/or the filaments and that can act as a thermocouple (e.g., having thermosensing properties).

In embodiments in which the needle is configured to create lesions offset from the central longitudinal axis, and an additional target nerve or target volume is within a volume that may be ablated using the needle in its current position but in a different rotational orientation, the procedure may continue as follows. First, after the initial RF energy application, the filaments may be retracted into the needle. Once retracted, the needle may be rotated, and the filaments redeployed. The redeployment may have the same characteristics (e.g., length of the deployed portions of the filaments) as the original deployment or different characteristics. Next, the reoriented needle may be used to at least partially ablate the additional target nerve or target volume. Such retargeting of ablation volumes without repositioning (e.g., without withdrawing the needle from the patient and reinserting), may result in reduced patient trauma as compared to known spinal RF neurotomy procedures, which may require removal and reinsertion of a needle to achieve lesioning of the second target volume. Moreover, such retargeting of ablation volumes without repositioning (e.g., with only rotation of the needle, without additional tissue piercing) may result in the ability to create uniquely shaped lesions from a single insertion position. Such shaped lesions may include, for example, lesions that are in the shape of two or more intersecting spheres or oblong spheroids. The steps of retracting the filaments, rotating the needle, redeploying the filaments, and applying RF energy may be repeated a plurality of times. In some embodiments, an second ablation volume may be defined without rotating the needle, but by different deployment characteristics (e.g., lengths, RF energy parameters, etc.) of the filaments.

In embodiments in which the additional target nerve or target volume is not within a volume that may be ablated by rotating the needle, the needle may be repositioned. Such repositioning may include partially or fully removing the needle from the patient and then repositioning the needle and repeating the herein-described steps. In some embodiments, the second ablation is performed using a different needle (e.g., a needle with different properties (e.g., longer filaments)) than the original needle.

When no additional ablation is desired, the filaments of the needle may be retracted, and the needle may be removed from the patient. After removal of the needle, a sterile bandage may be placed over the needle insertion site or sites. The patient may then be held for observation and recovery from the effects of any sedative that may have been administered.

Examples of specific spinal RF neurotomy procedures will now be described. Generally, steps unique to each procedure will be discussed while steps common to any spinal RF neurotomy procedure (e.g., site preparation such as infiltrating the skin and subcutaneous tissues with 1.5% lidocaine to achieve skin anesthesia, nicking the skin to facilitate needle insertion, insertion monitoring with fluoroscopy, stimulation, etc., filament deployment mechanics, needle removal, and the like) will not be further discussed. Each of the procedures is described as being performed with a needle comprising two filaments offset from the central longitudinal axis, for example as described herein. It will be appreciated that the variations in needle configuration discussed herein may be used in these procedures. For example, to increase the offset of the created lesion relative to the central longitudinal axis, curved filaments (e.g., as illustrated in FIG. 10) and/or partially insulated filaments (e.g., as illustrated in FIGS. 3H and 3I) may be used to create a lesion different properties (e.g., greater offset from the central longitudinal axis).

1. Lumbar RF Neurotomy of a Medial Branch Nerve Proximate a Lumbar Facet Joint.

This process may include using a needle that enables the creation of lesions that are offset from the central longitudinal axis. The procedure will be described as being performed on the L5 vertebra 1101 of FIG. 12 and the needle 103 of FIG. 2A. It should be understood that other embodiments of needles described herein and/or other lumbar vertebra may be used in the described procedure or variations thereof.

Figure 12:
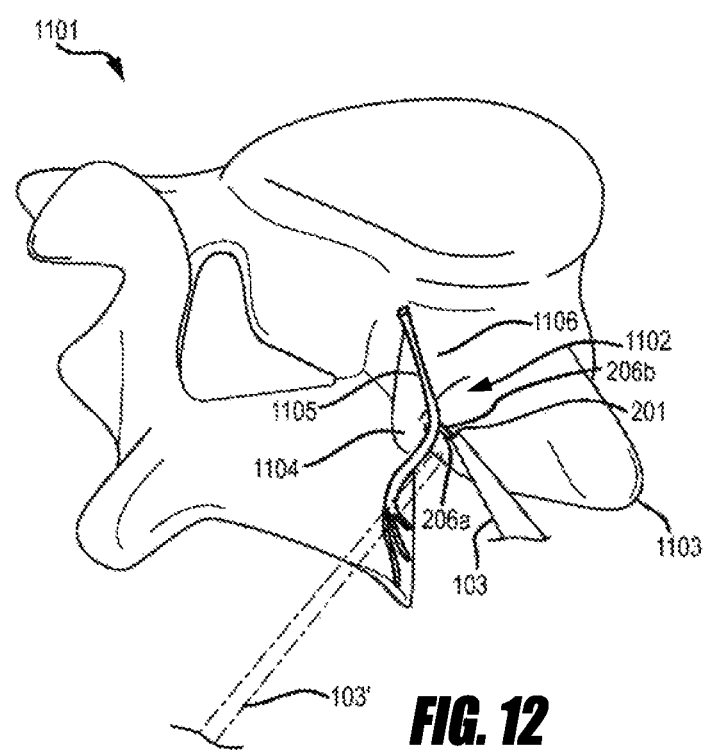
FIG. 12 is a perspective view of the needle of FIG. 2A positioned relative to a lumbar vertebra for performing RF neurotomy.

The lumbar RF neurotomy process may include positioning the tip 201 of the needle 103 (e.g., using fluoroscopic navigation) such that the tip 201 is in contact with, or proximate to, the groove 1102 between the transverse process 1103 and the superior articular process 1104 of the targeted lumbar vertebra 1101. Such positioning is shown in FIG. 12. By contacting the lumbar vertebra 1101, a positive determination of the position of the needle 103 may be made. By way of example, such positioning may be performed such that the needle 103 is within 30° of being perpendicular to the lumber vertebra 1101 at the point of contact with the lumbar vertebra 1101, or at the point of the lumbar vertebra 1101 closest to the tip 201 of the needle 103. Optionally, from such a position, the needle 103 may be retracted a predetermined amount (e.g., between about 3 mm and about 5 mm), for example as measured by markers 224 on the needle 103, as determined using the collar about the elongated member 203 discussed herein, and/or by fluoroscopic navigation.

The process may include rotating the needle 103 such that the midpoint 502 is oriented toward the superior articular process 1104 and a medial branch nerve 1105 that is positioned along a lateral face 1106 of the superior articular process 1104. Next, the filaments 206a, 206b may be advanced to the deployed position, as shown in FIG. 12. The positions of the needle 103 and the deployed filaments 206a, 206b may be verified using fluoroscopy and/or patient stimulation (e.g., motor and/or sensory). The RF probe 401 may then be inserted into the lumen 222 such that RF energy emanating from the probe 103 will be conducted by the tip 201 and filaments 206a, 206b to the target medial branch nerve 1105 and away from the intermediate branch of the posterior primary ramus.

Next, RF energy may be applied to the RF probe 401. The RF energy emanating from the needle 103 may be preferentially biased toward the target medial branch nerve 1105. The lesion created by such a procedure may, for example, have a maximum cross-sectional dimension of between about 8 mm and about 10 mm, and may ablate a corresponding portion of the medial branch nerve 1105, thus denervating the facet joint.

In some embodiments, the needle may be operable to create a generally symmetric lesion relative to its central longitudinal axis (e.g., as illustrated in FIG. 9). In certain such embodiments, the sequence of steps may include insert needle, deploy filaments, and apply RF energy.

In some embodiments, the needle may be inserted to be along the length of a portion of the nerve (as illustrated by needle 103' outlined by broken lines). Such positioning may be similar to known methods of RF neurotomy performed using needles without filaments. After positioning the needle, the filaments may be deployed and a lesion may be created. As noted herein, a needle with deployable filaments that is capable of producing a lesion equivalent to that of a needle without deployable filaments may be smaller in diameter than the needle without deployable filaments. Although positioning of the needle 103' may be similar to known processes, the process utilizing the needle 103' with deployable filaments may cause less trauma and be safer than procedures using a needle without deployable filaments due to the smaller size of the needle with deployable filaments. As discussed herein, the peak temperatures capable of producing the desired lesion volume may be less when using the needle 103' with deployable filaments as compared to a needle without deployable filaments, further contributing to patient safety. The filaments of the needle 103' may be partially or fully deployed to achieve a desired lesion location, shape, and/or size.

It is noted that the illustrated deployment of needle 103 with the filaments 206a, 206b deployed may be used to create a lesion that approximates a lesion that would be created with the needle without filaments that is placed in the position of needle 103' (e.g., parallel to the target nerve 1105). The placement of needle 103 generally perpendicular to the surface of the L5 vertebra 1101 may be less difficult to achieve than the parallel placement of the needle 103'.

2. Sacroiliac Joint (SIJ) RF Neurotomy of the Posterior Rami.

This process may include using a needle that enables the creation of lesions which are offset from the central longitudinal axis. The procedure will be described as being performed on the posterior rami 1201 of the SIJ of FIG. 12 and using the needle 103 of FIG. 2A. It should be understood that other embodiments of needles described herein and/or other portions of the SIJ may be used in the described procedure or variations thereof.

As part of the SIJ RF neurotomy process, it may be desirable to create a series of lesions in a series of lesion target volumes 1203a-1203h lateral to the sacral foramina 1211, 1212, 1213 of a side of the sacrum 1200 to ablate posterior rami 1201 that are responsible for relaying nociceptive signals from the SIJ. Since the exact positions of the rami 1201 may not be known, ablating such a series of target volumes 1203a-1203h may accommodate the variations in rami 1201 positions. The series of target volumes 1203a-1203h may be in the form of one or more interconnected individual target volumes, such as the target volumes 1203a, 1203b. In some embodiments, the process further comprises forming a lesion 1208 between the L5 vertebra 1209 and the sacrum 1200 to ablate the L5 dorsal ramus.

The SIJ RF neurotomy process may include positioning the tip 201 of the needle 103 (e.g., using fluoroscopic navigation) such that it is in contact with, or proximate to, and in lateral relation to the S1 posterior sacral foraminal aperture (PSFA) 1211 at a first point 1204 that is at the intersection of the two target volumes 1203a, 1203b. Such positioning may be performed such that the needle 103 is oriented within 30° of being perpendicular to the sacrum 1200 at the point of contact (or at the point of the sacrum 1200 closest to the tip 201 of the needle 103). By contacting the sacrum 1200, a positive determination of the position of the needle 103 may be made. Optionally, from such a position, the needle 103 may be retracted a predetermined amount (e.g., between about 3 mm and about 5 mm) as measured, for example, by markers 224 on the needle 103, as determined using the collar about the elongated member 203 discussed herein, and/or by fluoroscopic navigation. For example, a contralateral posterior oblique view may be obtained to ascertain that the tip 201 has not entered the spinal canal. For example, a fluoroscopic view may be obtained looking down the length of the needle 103 to verify that the needle 103 is properly offset from the S1 PSFA 1211 and/or a fluoroscopic view may be obtained looking perpendicular to the central longitudinal axis 223 to verify that the needle 103 is not below the surface of the sacrum (e.g., in the S1 PSFA 1211). An electrical signal may be applied to the needle 103 to stimulate nerves proximate to the tip 201 to verify correct needle 103 placement.

The SIJ RF neurotomy process may include rotating the needle 103 such that the midpoint 502 is oriented toward the first target volume 1203a in the direction of arrow 1205a. Next, the filaments 206a, 206b may be advanced to the deployed position. The position of the needle 103 and the deployed filaments 206a, 206b may be verified using fluoroscopy and/or stimulation (e.g., motor and/or sensory). The RF probe 401 may be inserted into the lumen 222 before, during, and/or after filament deployment such that RF energy emanating from the needle 103 will be conducted by the tip 201 and the filaments 206a, 206b to the first target volume 1203a. Next, RF energy may be applied to the RF probe 401. The RF energy emanating from the needle 103 may be preferentially biased toward the first target volume 1203a. The lesion created by such an application of RF energy may, for example, have a maximum cross-sectional dimension of between about 8 mm and about 10 mm, and may ablate a corresponding portion of the rami 1201.

Next, the filaments 206a, 206b may be retracted and the needle 103 may be rotated approximately 180° such that the midpoint 502 is oriented toward the second target volume 1203b in the direction of arrow 1205b. Optionally, some lateral repositioning of the needle may be performed (e.g., without any needle pull back or with a small amount of needle pull back and reinsertion). Next, the filaments 206a, 206b may be advanced to the deployed position. The position of the needle 103 and the deployed filaments 206a, 206b may be verified using fluoroscopy and/or stimulation (e.g., motor and/or sensory). The RF probe 401 may remain in the lumen 222 during the repositioning, or may be removed and then reinserted. Next, RF energy may be applied to the RF probe 401 to create a lesion corresponding to the second target volume 1203b.

Figure 13:
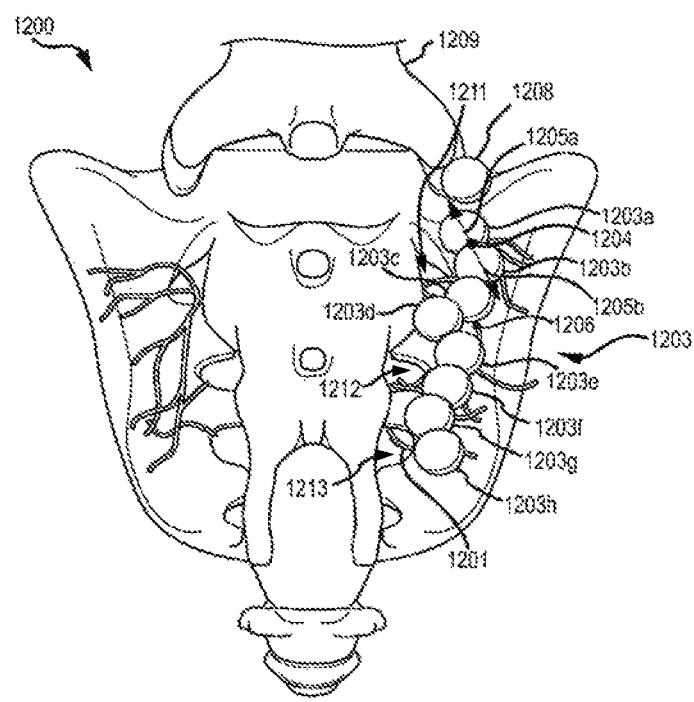
FIG. 13 is an illustration of a sacrum including target lesion volumes for performing Sacroiliac Joint (SIJ) RF neurotomy.
Figure 14:
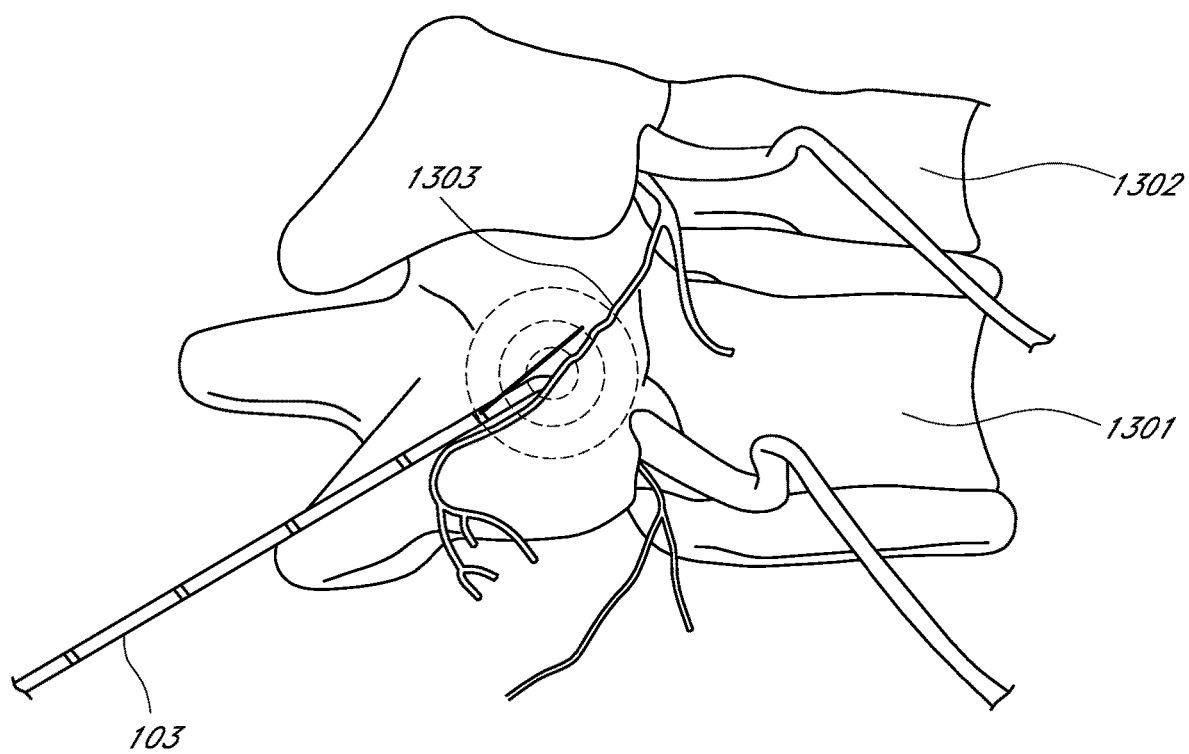
FIG. 14 is a perspective view of the needle of FIG. 2A positioned relative to a thoracic vertebra for performing RF neurotomy.

In this regard, with a single insertion of the needle 103, two interconnected lesions (which may also be considered to be a single oblong lesion) may be created. Compared to methods in which an RF probe must be repositioned prior to each application of RF energy, the number of probe repositioning steps may be greatly reduced, reducing patient trauma and procedure duration. In this regard, a continuous region of lesioning may be achieved about the S1 PSFA 1211 such that the lesion occupies a volume surrounding the S1 PSFA 1211 from about the 2:30 clock position to about the 5:30 clock position (as viewed in FIG. 13). Such lesioning may help to achieve denervation of the posterior rami proximate to the S1 PSFA 1211.

The herein procedure may be repeated as appropriate to create lesions corresponding to the entire series of target volumes 1203a-1203h, thus denervating the SIJ. For example, a first insertion may ablate the volumes 1203a, 1203b, a second insertion may ablate the volumes 1203c, 1203d, a third insertion may ablate the volumes 1203e, 1203f, and a fourth insertion may ablate the volumes 1203g, 1203h. In this regard, a similar continuous region of lesioning may be achieved about the S2 PSFA 1212 and a region of lesioning from about the 12:00 clock position to about the 3:00 clock position (as viewed in FIG. 13) relative to the S3 PSFA may be achieved about the S3 PSFA 1213. A lesion 1208 may also be created at the base of the superior articular process of the L5 1209 dorsal ramus in the grove between the superior articular process and the body of the sacrum. The needle 103 may be inserted generally perpendicular to the plane of FIG. 13 to produce the lesion 1208.

In some embodiments, three or more lesions may be created with a needle in a single position. For example, a needle positioned at a point 1206 proximate to three target volumes 1203c, 1203d, 1203e, may be operable to create lesions at each of the three target volumes 1203c, 1203d, 1203e, thus further reducing the number of needle repositionings.

In some embodiments, each individual lesion corresponding to the series of target volumes 1203 may be created using a needle with deployable filaments in which the needle is repositioned prior to each application of RF energy. In certain such embodiments, the sequence of steps may be insert needle, deploy filaments, apply RF energy, retract filaments, reposition needle, and repeat as appropriate to create each desired lesion. Such a procedure may be conducted, for example, using a needle capable of producing a lesion symmetric to a central longitudinal axis of the needle (e.g., the needle of FIG. 9).

3. Thoracic RF Neurotomy of a Medial Branch Nerve.

This process may include using a needle that enables the creation of lesions which are offset from the central longitudinal axis of the needle. Successful treatment of thoracic z-joint pain using radiofrequency ablation of relevant medial branch nerves can be challenging owing to the inconsistent medial branch location in the intertransverse space, especially levels T5-T8. A needle without filaments is generally positioned at multiple locations in the intertransverse space to achieve sufficient tissue ablation for successful medial branch neurotomy. The procedure will be described as being performed on an intertransverse space between adjacent vertebrae 1301, 1302 of the T5 to T8 thoracic vertebrae using FIG. 14 and the needle 103 of FIG. 2A. It should be understood that other embodiments of needles described herein and/or other vertebrae may be used in the described procedure or variations thereof.

The process may include obtaining a segmental anteroposterior image at target level defined by counting from T1 and T12. This may be followed by obtaining an image that is ipsalateral oblique about 8° to about 15° off-sagittal plane of the spine to visualize costotransverse joint lucency clearly. This can allow improved visualization of the superior-lateral transverse process, especially in osteopenic patients. The angle can aid in directing the probe to a thoracic anatomic safe zone medial to the lung, reducing risk of pneumothorax.

The skin entry site for the needle 103 may be over the most inferior aspect of transverse process slightly medial to costotransverse joint. Inserting the needle 103 may include navigating the device over the transverse process over the bone to touch the superior transverse process slightly medial to the costotransverse joint. The process may include checking anteroposterior imaging to demonstrate that the tip 201 of the needle 103 is at the superolateral corner of the transverse process. The process may also include checking a contralateral oblique image view (e.g., at ±15°) to demonstrate, for example in "Pinnochio" view, the target transverse process in an elongate fashion. This view can be useful for showing the tip 201 of the needle 103 in relationship to the superolateral margin of the transverse process subadjacent to the targeted medial branch nerve. The process may include retracting the tip 201 slightly (e.g., about 1 mm to about 3 mm). In some embodiments, retracting the tip 201 positions the ports at the superior edge of the process (e.g., visible with a radiopaque marker).

In some embodiments, medial to lateral placement may be performed entering the skin beneath the segmental spinous process, and navigating the needle 103 over the transverse process to contact a point just proximal to the superolateral corner of the transverse process. The tip 201 may then be advanced to approximate the exit port 304a, 304b of the filaments 206a, 206b with the superior margin of the transverse process, and the filaments 206a, 206b are deployed.

The process may include rotating the needle 103 such that the midpoint 502 is oriented toward the intertransverse space between the vertebrae 1301, 1302 and the medial branch nerve 1303 that is positioned therein. Next, the filaments 206a, 206b may be advanced ventral into the intertransverse space between the vertebrae 1301, 1302 to the deployed position. The position of the needle 103 and deployed filaments 206a, 206b may be verified using fluoroscopy (e.g., using lateral imaging) and/or stimulation (e.g., motor and/or sensory), for example to rule out proximity to ventral ramus. In some embodiments, the filaments 206a, 206b are deployed in a ventral direction in the intratransverse space, which may be confirmed by obtaining lateral. The RF probe 401 may be inserted into the lumen 222 such that RF energy emanating from the probe 103 will be conducted by the tip 201 and the filaments 206a, 206b to the target medial branch nerve 1303. Next, RF energy may be applied to the RF probe 401. The RF energy emanating from the needle 103 may be preferentially biased toward the volume between the vertebrae 1301, 1302. The lesion created by such a procedure may, for example, have a maximum cross-sectional dimension of between about 8 mm and about 10 mm, and may ablate a corresponding portion of the medial branch nerve 1303. This method can treat the medial branch as it curves out of the intratransverse space emerging into the posterior compartment of the back. The directional bias of the lesion may advantageously heat towards the target and away from the skin.

It is noted that thoracic RF neurotomy performed on other thoracic vertebrae may call for different sizes of lesions. For example, thoracic RF neurotomy performed on the T3-T4 vertebrae may require a smaller lesion volume than the herein-described procedure, and thoracic RF neurotomy performed on the T1-T2 vertebrae may require a still smaller lesion volume. As described herein, the deployment of the filaments of the needle 103 may be varied to achieve such desired target lesion volumes, or different needles may be used (e.g., having shorter filaments in the fully deployed position).

4. Cervical Medial Branch RF Neurotomy.

Embodiments of needles described herein (e.g., the needle 103 of FIG. 2A) are capable of creating a volume of tissue ablation necessary for complete denervation of the cervical zygapophyseal joints, including the C2/3 cervical zygapophyseal joint (z-joint). Tissue ablation for cervical z-joint using embodiments of needles described herein may be accomplished using a single placement and single heating cycle. Such single placement and single heating cycle may avoid unnecessary tissue damage from multiple placements of a filament-free needle, and unintended injury to collateral tissue caused by excessive lesioning. The zone of ablation can be designed to provide sufficient and necessary tissue coagulation for a successful procedure, and thus may be expected to improve the outcomes of patients undergoing spinal radiofrequency neurotomy.

Figure 15:
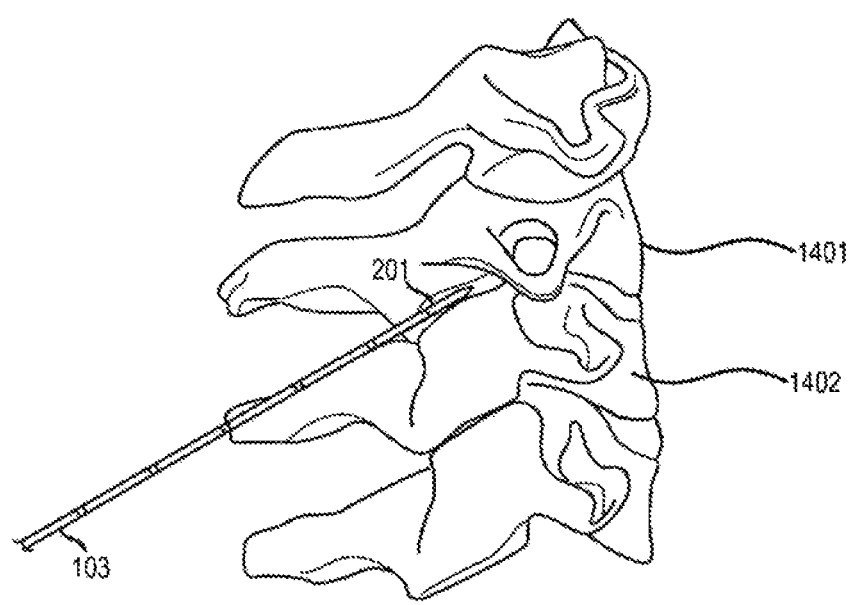
FIG. 15 is a perspective view of the needle of FIG. 2A positioned relative to the C2/3 cervical zygapophyseal joint (z-joint) for performing cervical medial branch RF neurotomy on the third occipital nerve.

A cervical medial branch RF neurotomy procedure will be described as being performed on the third occipital nerve at the C2/3 z-joint using the needle 103 as shown in FIG. 15. In FIG. 15, the needle 103 is positioned between the C2 vertebra 1401 and the C3 vertebra 1402.

In a first step, the patient may be placed in a prone position on a radiolucent table suited to performing fluoroscopically guided spinal procedures. Sedation may be administered. The patient's head may be rotated away from the targeted side. Sterile skin prep and draping may be performed using standard well-described surgical techniques.

For Third Occipital Nerve (TON) ablation (C2/3 joint innervation) the lateral aspect of the C2/3 Z-joint is located under either parasagittal or, alternatively, ipsilateral oblique rotation of less than or equal to about 30° (e.g., between about 20° and about 30°) of obliquity relative to the true sagittal plane of the cervical spine. The skin entry point may be infiltrated with local anesthetic. Then, the tip 201 of the needle 103 is moved over the most lateral aspect of bone of the articular pillar at the juncture of the C2/3 z-joint to a first position contacting bone proximate to the most posterior and lateral aspect of the z-joint complex, for example using a "gun-barrel" technique to touch the most lateral and posterior aspect of the articular pillar at the point of maximal concavity for level below C2/3 or at the point of maximal convexity at the C2/3 level when targeting the TON.

Once boney contact is made, the needle 103 may be retracted a predetermined distance (e.g., between about 1 mm and about 3 mm) and the filaments are deployed towards the lateral aspect of the C2/3 z-joint. The filaments will spread to encompass anticipated rostrocaudal variation in the target nerve location. The angle of the filaments with respect to the tip may effectively cover the ventral aspect of the articular pillar up to the border of the superior articular process, thus incorporating benefits of a 30° oblique pass. The needle 103 may be rotated about a central longitudinal axis prior to filament deployment to ensure that deployment will occur in the desired direction.

Multiplanar fluoroscopic imaging may then be employed to verify that the tip and the filaments are positioned as desired. For example, it may be verified that the filaments are positioned straddling the lateral joint lucency, and posterior to the C2/3 neural foramen. Useful imaging angles include anterior-posterior (AP), lateral, and contralateral oblique (Sluijter) views. To further verify adequate positioning of the needle 103, motor stimulation may be performed by delivering a voltage (e.g., up to about 2 volts) at about 2 Hz to the tip 201 and filaments and/or sensory stimulation may be performed at appropriate voltage (e.g., between about 0.4 volts and about 1 volt) and frequency (e.g., about 50 Hz).

After position verification, RF energy may be applied to the tip and the plurality of filaments to generate heat that ablates a portion of the third occipital nerve. The cross-sectional dimensions of the lesion (e.g., between about 8 mm and about 10 mm) can incorporate all medial branches as well as the TON, which has a nerve diameter of about 1.5 mm. The directional nature of the lesion, offset towards the filaments, provides a beneficial measure of safety regarding undesired thermal damage to the skin and to collateral structures. Safety concerns may be further satisfied by fluoroscopic observation of the filaments dorsal to the intervertebral foramen and/or lack of ventral ramus activation during stimulation (e.g., with 2 Hz and 2 volts). After lesioning, the device may be removed. For levels below the C2/3 z-joint, the procedure may be similar than as described herein with respect to the third occipital nerve, with the exception that the initial boney contact target is at the waist of inflection point of the articular pillar.

Other spinal RF procedures may also benefit from the asymmetrical application of RF energy from embodiments of the needles described herein. Such asymmetry may, for example, be used to project RF energy in a desired direction and/or limit the projection of RF energy in undesired directions. The configuration of the filaments may be selected for a particular application to produce a desired size, shape, and/or location (relative to the needle tip) of a lesion within the patient. The location of the lesion may be offset distally and/or laterally from the tip of the needle as desired for a particular application.

It will be appreciated that the delivery of RF energy to tissue in the anatomy can be practiced for a multitude of reasons, and embodiments of the needles described herein may be adapted (e.g., modified or scaled) for use in other medical procedures. For example, embodiments of needles described herein could be used to deliver RF energy as a means to cauterize "feeder vessels," such as in bleeding ulcers and/or in orthopedic applications. For another example, embodiments of the needles described herein could be adapted for use in procedures such as cardiac ablation, in which cardiac tissue is destroyed in an effort to restore a normal electrical rhythm in the heart. Certain such uses could further benefit from the ability of embodiments of needles described herein to deliver fluid through a lumen since, for example, emerging procedures in cardiac therapy may require the ability to deliver stem cells, vascular endothelial growth factor (VEGF), or other growth factors to cardiac tissue. The ability to steer embodiments of the needle described herein may provide significant benefit in the field of cardiovascular drug delivery.

Figure 18A:
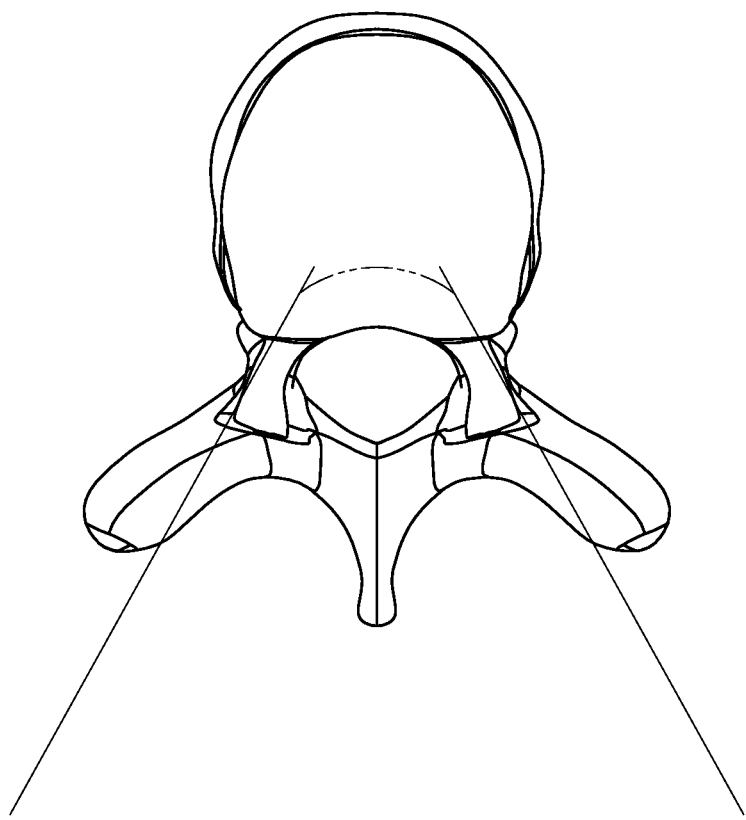
FIG. 18A is an axial view of posterior oblique needle entry.
Figure 18B:
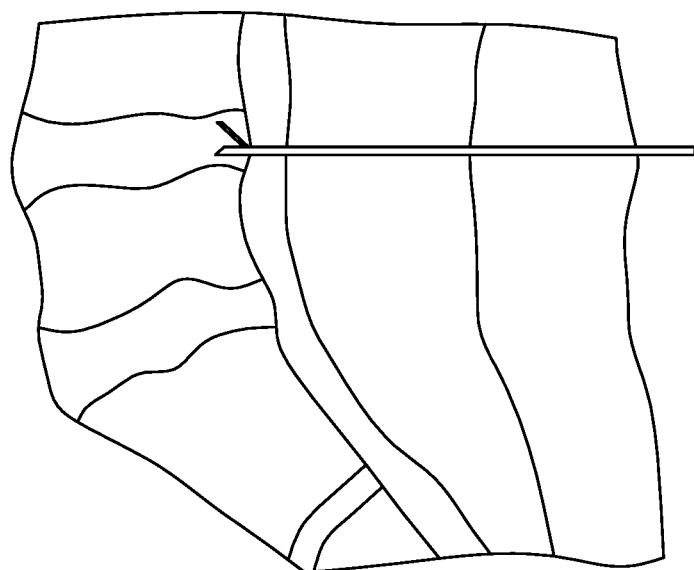
FIG. 18B is a sagittal view of posterior oblique needle entry.

For example, a needle may be adapted for use in vertebral disc heating. A primary longer needle (e.g., having a length of about 15 cm and a tip with an uninsulated active portion having a length of about 2 mm, although other dimensions are also possible), is placed into the post posterolateral margin of a painful intervertebral disc, for example as described elsewhere for provocation discography and/or therapeutic disc access procedures such as Dekompressor® discectomy and disc biacuplasty. Once positioned in the posterior annulus, as confirmed with fluororscopy, tactile feedback, and/or characteristic impedance readings, a single filament is deployed to traverse the posterior annulus in a lateral to medial fashion in the lamella of the annulus fibrosis, for example as illustrated in FIG. 18A, which is an axial view of posterior oblique needle entry with the main axial tip in the posterior annulus and deployed a filament moving lateral to medial in the lamella of the posterior annulus, and FIG. 18B, which is a sagittal view with a filament moving across the posterior annulus from lateral to medial.

In some embodiments, the filament may act as a thermocouple (e.g., comprising a material having thermosensing properties as described herein) to allow precise measurement of actual temperatures of the annulus. In some embodiments, the filament includes a lumen configured to allow injection of therapeutic substances (e.g., methylene-blue) upon withdrawal for substantially simultaneous chemo-thermo-neurolysis and/or to allow injection of contrast agent for confirmation of intraannular placement that is definite, for example as opposed to potentially dangerous placement in the spinal canal or futile placement in the nucleus pulposus. In some embodiments, the filament has an exit angle greater than about 30°. In some embodiments, the filament includes a beveled Quincke tip oriented to bias away from the spinal canal upon advancement, as needles in tissue track away from bevel angles. In some embodiments, the deployed filament has a length between about 10 mm and about 12 mm. In some embodiments, the needle does not include a lumen for injection of liquid. In certain such embodiments, the area not occupied by a lumen may be used for the filament, which may be more complicated due to use as a thermocouple and/or including a lumen.

Bipolar or monopolar RF energy is applied to the tip and to the filament, creating a zone of therapeutic heating across the posterior disc annulus and resulting in destruction of the pain fibers in approximately the outer third of the annulus. The procedure may be repeated on the opposite side. In some embodiments, the needle includes a plurality of deployable filaments, and gap between the filaments (e.g., the distance 604 in FIG. 6) is between about 2 mm and about 10 mm, between about 4 mm and about 8 mm, between about 5 mm and about 7 mm (e.g., about 6 mm), combinations thereof, and the like.

Example 1

Sections of raw muscle tissue were allowed to equilibrate to 37° C. in a distilled water bath. A needle with tines deployed was positioned to contact the tissue surface in 10 trials and was inserted into tissue in 10 trials. A Radionics RFG 3C RF generator energy source was set at 75° C. for 80 seconds. Propagation of tissue coagulation was documented with video and a calibrated Flir T-400 thermal camera. Tissue samples were sectioned and coagulation zones measured. Infrared observation demonstrated symmetric and homogenous lesion progression without hot spots or focal over-impeding. Calculated volume averaged 467±71 mm$^3$/lesion. Topography was elongate spheroid offset from the central axis toward the filaments. Thus, the needle reliably produced lesions that are potentially useful in spinal applications.

Example 2

A 47 year-old male with recalcitrant right-sided lumbar zygapophysial joint pain presented for radiofrequency medial branch neurotomy. The diagnosis had been made by greater than 80% relief documented following both intraarticular z-joint injection and confirmatory medial branch blocks.

The patient was placed in a prone position on the fluoroscopy table and standard monitors were applied. No sedation was administered. The lumbar region was extensively prepped with chlorhexidine-alcohol and draped in routine sterile surgical fashion. The C-arm was adjusted to visualize a true AP of the L4/5 intervertebral disc space with vertebral end plates squared-off, and spinous process positioned between the pedicle shadows. The C-arm was rotated 30°-40° ipsilateral to the target joint until the base of the SAP of the L4 and L5 were clearly visualized. A target point was identified at the midpoint of the base of the SAP, and the overlying skin and subcutaneous tissues were infiltrated with 1.5% lidocaine. A small skin nick was made with an 18-gauge needle to facilitate placement of an embodiment of the needles described herein. Once skin anesthesia was established, the needle, with filaments in the retracted position, was advanced using a gun-barrel approach until boney contact was made with the base of the SAP. The needle was then retracted off the bone slightly, and using the indentation on the hub for orientation, the actuator was rotated 360° to fully deploy the filaments. Filaments were felt to touch bone at the base of the SAP. AP, oblique, and lateral images were obtained to document the placement and to confirm that the filaments were directed toward the SAP. In this position, the lesion was biased to cover any variant medial branch situated higher up the SAP. If the filaments were not directed in an ideal fashion, they were retracted, the device was rotated as necessary, and the filaments were redeployed. Motor stimulation at a frequency of 2 Hz up to 2 volts was incrementally administered with brisk activation of the multifidus, but with no activation of any ventral root inenervated musculature. Sensory stimulation at 50 Hz at 0.6 volts elicited a concordant aching in the distribution of the patient's pain. A 22-gauge, 10 cm, 10 mm active tip RFK connected to an independently grounded second RF generator was placed sequentially at the following targets for in vivo thermometry: (1) Most inferior and dorsal location in the supra-segmental neural foramen evaluating the potential for thermal injury of spinal nerve; (2) At a point lateral on the transverse process approximating the location of intermediate/lateral branches of the posterior primary rami; (3) At or near the central axis of the needle during stable heating; (4) On the SAP at the base and successively higher on mamilliary process to evaluate heating on the region of potential MB variation (up the SAP). The process was then repeated for denervation of the L5.

Following the confirmation of safe and optimal placement by fluoroscopy and stimulation, the heating protocol was initiated based on previous branch testing in egg white and chicken meat. The protocol included: 45° C. for 15-30 seconds, await rapid temperature increase signaling primary consolidation of heating and biophysical changes around core axis; 50° C. for 15 seconds; 60° C. for 15 seconds; 70° C. for 10 seconds to record foraminal temperatures only.

Generator parameters during ablation were appropriate and within the tolerance range for a generically programmed RF generator. The lower starting impedance, relative to a monopolar needle, may be explained by greatly increased conductive surface of the needle. Brief temperature fluctuation was noted as the lesion propagated to encompass the central axis housing the thermocouple. It is anticipated that changes in the generator software may be useful to support various embodiments of the described device. Impedance readings were 75 ohms to 250 ohms. Power ranges were 2 watts to 11 watts, typically 3 watts to 4 watts after 10 seconds into the procedure.

The thermal mapping results were as follows: (1) Perineural temperatures (neurogram obtained via TC2) at the supra-adjacent spinal nerve did not increase from a 38° C. baseline; (2) Temperature readings from the TC2 placed near the central axis of the needle reflected delivered temperature from the generator; (3) Temperature readings from the base of the SAP to relatively dorsal position on the SAP exceed the neuroablative threshold of 45° C.

The patient experienced minimal discomfort following the procedure. For the sake of full disclosure, it is noted that the patient is an inventor of the present application. No postoperative analgesics were required. The patient reported near complete relieve of his right-sided low back pain within 10 days of the procedure. Bilateral paraspinal EMG at L3, L4, and L5 was performed 20 days after the RF procedure, as documented in Table 1:

TABLE 1

Paraspinal EMG

| Side | Muscle | Nerve | Root | Ins Act | Fibs | Psw |
|---|---|---|---|---|---|---|
| Left | L3 Parasp | Rami | L3 | Nml | Nml | Nml |
| Left | L4 Parasp | Rami | L4 | Nml | Nml | Nml |
| Left | L5 Parasp | Rami | L5 | Nml | Nml | Nml |
| Right | L3 Parasp | Rami | L3 | Nml | Nml | Nml |
| Right | L4 Parasp | Rami | L4 | *Incr | *1+ | *1+ |
| Right | L5 Parasp | Rami | L5 | *Incr | *1+ | *1+ |

*Needle evaluation of the right L4 paraspinal and the right L5 paraspinal muscles showed increased insertional activity and slightly increased spontaneous activity.
*All remaining muscles showed no evidence of electrical instability.

There was electrodiagnostic evidence of active and acute denervation of the right lumbar paraspinals at the L4 and L5 levels. The contralateral left-sided paraspinals appeared normal. These findings are consistent with the clinical history of recent right lumbar radiofrequency rhizotomy.

Thus, the needle was safely and effectively used to accomplish lumbar medial branch neurotomy. Thermal mapping demonstrated a safe and effective isotherm consistent with bench predictions, and EMG of the lumbar paraspinals demonstrated objective evidence of medial branch coagulation. The needle appears to extend beneficially on existing techniques and technology. For a first example, facilitated placement for lumbar medial branch neurotomy using "down-the-beam" technique akin to diagnostic medial branch block. This approach can be applied to other spinal targets such as cervical z-joint neurotomy, thoracic z-joint neurotomy, sacroiliac joint denervation, central innercation of the lateral C1-2 joint, RF neurotomy thoracic sympathetic chain, RF neurotomy sphlancnic chain at T10, 11, 12, RF neurotomy lumbar sympathetic pain, and RF neurotomy superior hypogastric plexus. For a second example, lab testing and in vivo thermal data demonstrates a large volume suited for efficiently dealing with common variations in afferent sensory pathways. The lesion can be directed relative to the central longitudinal axis of the needle toward targets and away from sensitive collateral structures. For a third example, the needle can deliver meaningful motor and/or sensory stimulation for documentation of safe placement. For a fourth example, lesion topography is driven by needle design, and does not require high temperatures (e.g., greater than 80° C.) for extended times. It is believed that 60° C. for 60 seconds is adequate for most targets. Reduced procedural time and/or lower temperatures should translate to fewer complications, expedited recovery, and/or diminished incidence of postoperative pain syndromes/dysesthesias. For a fifth example, relative to other large field lesion technology, the needle is of a uncomplicated and robust design, does not require additional support equipment, and is economical to manufacture.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Thus, it is intended that the scope of the invention herein disclosed should not be limited by the particular embodiments described herein.

What is claimed is:

1. A system comprising:
a radiofrequency probe; and
a needle apparatus that comprises:
a first hub;
an elongate member having a proximal end and a distal end, the proximal end being fixedly attached to the first hub, the elongate member comprising a lumen at an interior thereof, the lumen being configured to receive a distal end of the radiofrequency probe, the radiofrequency probe being separate from the needle apparatus;
a tip positioned at the distal end of the elongate member, the tip being configured to pierce body tissue;
a plurality of filaments movable between a retracted position at least partially in the elongate member and a deployed position at least partially out of the elongate member;
a second hub coupled to the plurality of filaments;
and an actuator coupled to the second hub and rotatable relative to the first hub, wherein rotation of the actuator in a first direction relative to the first hub moves the second hub axially relative to the first hub to advance the plurality of filaments to the deployed position, and wherein rotation of the actuator in a second direction relative to the first hub that is opposite the first direction moves the second hub axially relative to the first hub to retract the plurality of filaments to the retracted position,
wherein, when the radiofrequency probe is fully separated from the needle apparatus in a non-inserted state, such that the lumen and the first and second hubs are devoid of the radiofrequency probe, the plurality of filaments are movable via the actuator from the retracted position to the deployed position, and
wherein, after the plurality of filaments have been moved to the deployed position, the first and second hubs are each configured permit insertion therethrough of the radiofrequency probe and the lumen is configured to accept the radiofrequency probe therein to physically contact a conductive portion of the tip and thereby establish an electrically conductive path from the radiofrequency probe to the plurality of filaments, the plurality of filaments and the tip being configured to transmit radiofrequency energy from the radiofrequency probe to operate as a monopolar electrode, when the radiofrequency probe is inserted into the lumen.

2. The system of claim 1, wherein the first hub defines a first hub lumen, wherein the second hub defines a second hub lumen, and wherein the lumens of the first and second hubs are configured to permit the radiofrequency probe to be inserted therethrough and into the lumen at the interior of the elongate member.

3. The system of claim 2, wherein the actuator defines an actuator lumen within which a portion of the second hub is positioned.

4. The system of claim 2, wherein the second hub comprises a longitudinal protrusion that is positioned in the lumen of the first hub.

5. The system of claim 2, further comprising a fitting configured to be attached to a fluid delivery device to permit fluid to be delivered through each of the lumens of the first and second hubs and through the lumen at the interior of the elongate member.

6. The system of claim 1, wherein the elongate member defines the lumen that is at the interior thereof.

7. The system of claim 1, further comprising a tube positioned within the elongate member, wherein the tube defines the lumen at the interior of the elongate member.

8. The system of claim 1, wherein a single unitary structure defines the plurality of filaments, and wherein the single unitary structure is fixedly attached to the second hub.

9. The system of claim 8, wherein the single unitary structure comprises a wire.

10. The system of claim 1, wherein a single unitary structure defines the elongate member and the tip.

11. The system of claim 1, wherein the tip comprises a lumen, and wherein the lumen at the interior of the elongate member is configured to permit fluid to pass therethrough and then into the lumen of the tip.

12. The system of claim 1, wherein an inner surface of the actuator includes a helical track or a helical thread, the helical track or the helical thread causing axial movement of the second hub as the actuator is rotated.

13. The system of claim 1, wherein rotation of the actuator relative to the first hub creates linear motion of the second hub relative to the first hub without transmitting rotational motion to the second hub.

14. The system of claim 1, further comprising a key slot and a mating key that act together to limit the second hub to a linear motion along a central longitudinal axis of the needle apparatus as the actuator is rotated.

15. The system of claim 1, further comprising a projection, wherein the actuator comprises a helical track sized to accommodate the projection, and wherein, when the actuator is rotated relative to the first hub, the actuator interacts with the projection to transmit linear motion to the second hub while the rotational motion of the actuator is not transmitted to the second hub.

16. The system of claim 1, wherein the first hub includes a cavity sized to house a protrusion of the second hub, and wherein the second hub is limited to a linear motion relative to the first hub.

17. The system of claim 1, wherein the plurality of filaments comprises three filaments, and wherein an angle between each pair of adjacent filaments is about 120 degrees when the plurality of filaments are in the deployed position.

18. The system of claim 1, further comprising a fitting at a proximal end of the needle apparatus, the fitting being configured to provide a connection to a fluid source for injection of fluid through the lumen.

19. The system of claim 18, wherein, the system is operable in a first state in which the radiofrequency probe is fully separated from the needle apparatus in a non-inserted state and in which the fitting is connected to the fluid source for injection of fluid through the lumen, and wherein the system is operable in a second state in which the fitting is disconnected from the fluid source and in which the radiofrequency probe is inserted through the fitting into the lumen for delivery of radiofrequency energy along the electrically conductive path.

20. The system of claim 19, further comprising a tube that is a separate member relative to the elongate member, the tube defining the lumen at the interior of the elongate member.

21. The system of claim 18, wherein the fitting comprises a Luer fitting.

22. The system of claim 1, further comprising a tube that is a separate member relative to the elongate member, the tube defining the lumen at the interior of the elongate member.

23. The system of claim 1, wherein a single unitary structure defines the plurality of filaments, and wherein a proximal end of the single unitary structure is fixedly attached to the second hub.

24. The system of claim 1, wherein the lumen that is configured to receive the distal end of the radiofrequency probe therein is devoid of an opening at a distal end thereof, such that the distal end of the radiofrequency probe remains in the lumen during delivery of radiofrequency energy.

25. The system of claim 24, wherein the plurality of filaments extend distally beyond the distal end of the radiofrequency probe when the radiofrequency probe is fully inserted into the needle apparatus and when the plurality of filaments are in the deployed position, such that when radiofrequency energy is delivered to the radiofrequency probe, the plurality of filaments conduct radiofrequency energy that emanates from the radiofrequency probe beyond the distal end of the radiofrequency probe.

26. The system of claim 1, wherein the tip at least partially defines the lumen, and wherein the lumen is devoid of an opening at a distal end thereof.

27. The system of claim 26, wherein the plurality of filaments extend distally beyond the distal end of the radiofrequency probe when the radiofrequency probe is fully inserted into the needle apparatus and when the plurality of filaments are in the deployed position, such that when radiofrequency energy is delivered to the radiofrequency probe, the plurality of filaments conduct radiofrequency energy that emanates from the radiofrequency probe beyond the distal end of the radiofrequency probe.

28. The system of claim 1, wherein the needle apparatus is configured to maintain the distal end of the radiofrequency probe within the tip.

29. The system of claim 28, wherein the plurality of filaments extend distally beyond the distal end of the radiofrequency probe when the radiofrequency probe is fully inserted into the needle apparatus and when the plurality of filaments are in the deployed position, such that when radiofrequency energy is delivered to the radiofrequency probe, the plurality of filaments conduct radiofrequency energy that emanates from the radiofrequency probe beyond the distal end of the radiofrequency probe.

30. The system of claim 1, wherein the plurality of filaments extend distally beyond the distal end of the radiofrequency probe when the radiofrequency probe is fully inserted into the needle apparatus and when the plurality of filaments are in the deployed position, such that when radiofrequency energy is delivered to the radiofrequency probe, the plurality of filaments conduct radiofrequency energy that emanates from the radiofrequency probe beyond the distal end of the radiofrequency probe.

31. The system of claim 1, wherein the distal end of the radiofrequency probe contacts the conductive portion of the needle apparatus, when the radiofrequency probe is fully inserted into the lumen, to thereby establish the electrically conductive path from the radiofrequency probe to the plurality of filaments.

32. The system of claim 1, wherein the conductive portion of the needle apparatus is positioned at the distal end of the needle apparatus.

33. The system of claim 1, further comprising a tube that comprises a conductive material, the tube being a separate member relative to the elongate member, wherein the conductive portion of the needle apparatus that is physically contacted by the radiofrequency probe comprises the conductive material of the tube.

34. The system of claim 33, wherein when radiofrequency energy is emitted from the radiofrequency probe, the radiofrequency energy is conducted through the tube and into and through the plurality of filaments.

35. The system of claim 34, wherein the radiofrequency energy is further conducted into and through the tip.

36. The system of claim 1, wherein the tip comprises a conductive material, and wherein the conductive portion of the needle apparatus that is physically contacted by the radiofrequency probe comprises the conductive material of the tip.

37. The system of claim 36, wherein the tip is in physical and electrical contact with the plurality of filaments.

38. The system of claim 1, wherein the elongate member comprises a conductive material, and wherein the conductive portion of the needle apparatus that is physically contacted by the radiofrequency probe comprise the conductive material of the elongate member.

39. A system comprising:
a radiofrequency probe; and
a needle apparatus that comprises:
a first hub;
an elongate member having a proximal end and a distal end, the proximal end being fixedly attached to the first hub, the elongate member comprising a lumen at an interior thereof;
a tip positioned at the distal end of the elongate member, the tip being configured to pierce body tissue;
a plurality of filaments movable between a retracted position at least partially in the elongate member and a deployed position at least partially out of the elongate member;
a second hub coupled to the plurality of filaments;
and an actuator coupled to the second hub and rotatable relative to the first hub, wherein rotation of the actuator in a first direction relative to the first hub moves the second hub axially relative to the first hub to advance the plurality of filaments to the deployed position, and wherein rotation of the actuator in a second direction relative to the first hub that is opposite the first direction moves the second hub axially relative to the first hub to retract the plurality of filaments to the retracted position,
the first and second hubs being configured to permit insertion therethrough of a distal end of the radiofrequency probe, such that upon insertion of the radiofrequency probe through the first and second hubs, the distal end of the radiofrequency probe extends into the lumen at the interior of the elongate member to physically contact a conductive portion of the tip and thereby establish an electrically conductive path from the radiofrequency probe to the plurality of filaments, the plurality of filaments and the tip being configured to transmit radiofrequency energy from the radiofrequency probe to operate as a monopolar electrode, when the radiofrequency probe is inserted into the lumen at the interior of the elongate member.

40. The system of claim 39, wherein a fitting at a proximal end of the needle apparatus defines the lumen, the fitting being configured to provide a connection to a fluid source for injection of fluid through the lumen.

41. The system of claim 40, wherein, the system is operable in a first state in which the radiofrequency probe is fully separated from the needle apparatus in a non-inserted state and in which the fitting is connected to the fluid source for injection of fluid through the lumen, and wherein the system is operable in a second state in which the fitting is disconnected from the fluid source and in which the radiofrequency probe is inserted through the fitting into the lumen for delivery of radiofrequency energy along the electrically conductive path.

42. The system of claim 41, further comprising a tube that is a separate member relative to the elongate member, the tube defining the lumen at the interior of the elongate member.

43. The system of claim 40, wherein the fitting comprises a Luer fitting.

44. The system of claim 39, further comprising a tube that is a separate member relative to the elongate member, the tube defining the lumen at the interior of the elongate member.

45. The system of claim 39, wherein a single unitary structure defines the plurality of filaments, and wherein a proximal end of the single unitary structure is fixedly attached to the second hub.

46. The system of claim 39, wherein the lumen that is configured to receive the radiofrequency probe therein is devoid of an opening at a distal end thereof, such that the distal end of the radiofrequency probe remains in the lumen during delivery of radiofrequency energy.

47. The system of claim 46, wherein the plurality of filaments extend distally beyond the distal end of the radiofrequency probe when the radiofrequency probe is fully inserted into the needle apparatus and when the plurality of filaments are in the deployed position, such that when radiofrequency energy is delivered to the radiofrequency probe, the plurality of filaments conduct radiofrequency energy that emanates from the radiofrequency probe beyond the distal end of the radiofrequency probe.

48. The system of claim 39, wherein the tip at least partially defines the lumen, and wherein the lumen is devoid of an opening at a distal end thereof.

49. The system of claim 48, wherein the plurality of filaments extend distally beyond the distal end of the radiofrequency probe when the radiofrequency probe is fully inserted into the needle apparatus and when the plurality of filaments are in the deployed position, such that when radiofrequency energy is delivered to the radiofrequency probe, the plurality of filaments conduct radiofrequency energy that emanates from the radiofrequency probe beyond the distal end of the radiofrequency probe.

50. The system of claim 39, wherein the needle apparatus is configured to maintain the distal end of the radiofrequency probe within the tip.

51. The system of claim 50, wherein the plurality of filaments extend distally beyond the distal end of the radiofrequency probe when the radiofrequency probe is fully inserted into the needle apparatus and when the plurality of filaments are in the deployed position, such that when radiofrequency energy is delivered to the radiofrequency probe, the plurality of filaments conduct radiofrequency energy that emanates from the radiofrequency probe beyond the distal end of the radiofrequency probe.

52. The system of claim 39, wherein the plurality of filaments extend distally beyond the distal end of the radiofrequency probe when the radiofrequency probe is fully inserted into the needle apparatus and when the plurality of filaments are in the deployed position, such that when radiofrequency energy is delivered to the radiofrequency probe, the plurality of filaments conduct radiofrequency energy that emanates from the radiofrequency probe beyond the distal end of the radiofrequency probe.

53. The system of claim 39, wherein the distal end of the radiofrequency probe contacts the conductive portion of the needle apparatus, when the radiofrequency probe is fully inserted into the lumen, to thereby establish the electrically conductive path from the radiofrequency probe to the plurality of filaments.

54. The system of claim 39, wherein the conductive portion of the needle apparatus is positioned at the distal end of the needle apparatus.

55. The system of claim 39, further comprising a tube that comprises a conductive material, the tube being a separate member relative to the elongate member, wherein the conductive portion of the needle apparatus that is physically contacted by the distal end of the radiofrequency probe comprises the conductive material of the tube.

56. A system comprising:
a radiofrequency probe; and
a needle apparatus that comprises:
a first hub;
an elongate member having a proximal end and a distal end, the proximal end being fixedly attached to the first hub;
a tip positioned at the distal end of the elongate member, the tip being configured to pierce body tissue;
a plurality of filaments that are movable between a retracted position at least partially in the elongate member and a deployed position at least partially out of the elongate member;
a second hub coupled to the plurality of filaments;
an actuator coupled to the second hub and rotatable relative to the first hub, wherein rotation of the actuator in a first direction relative to the first hub moves the second hub axially relative to the first hub to advance the plurality of filaments to the deployed position, and wherein rotation of the actuator in a second direction relative to the first hub that is opposite the first direction moves the second hub axially relative to the first hub to retract the plurality of filaments to the retracted position, the actuator being operable to move the plurality of filaments to at least the deployed position prior to insertion of the radiofrequency probe into the needle apparatus;
a first lumen that extends to a proximal end of the needle apparatus; and
a second lumen at an interior of the elongate member that is in fluid communication with the first lumen,
the first lumen being configured to permit insertion of the radiofrequency probe therethrough and into the second lumen,
the second lumen being configured to receive the radiofrequency probe therein such that the radiofrequency probe physically contacts a conductive portion of the tip and thereby establishes an electrically conductive path from the radiofrequency probe to the plurality of filaments, and the plurality of filaments and the tip being configured to transmit radiofrequency energy from the radiofrequency probe to operate as a monopolar electrode, when the radiofrequency probe is inserted into the second lumen.

57. The system of claim 56, wherein a fitting at a proximal end of the needle apparatus defines the first lumen, the fitting being configured to provide a connection to a fluid source for injection of fluid through the first and second lumens.

58. The system of claim 57, wherein, the system is operable in a first state in which the radiofrequency probe is fully separated from the needle apparatus in a non-inserted state and in which the fitting is connected to the fluid source for injection of fluid through the first and second lumens, and wherein the system is operable in a second state in which the fitting is disconnected from the fluid source and in which the radiofrequency probe is inserted through the fitting into the second lumen for delivery of radiofrequency energy along the electrically conductive path.

59. The system of claim 58, further comprising a tube that is a separate member relative to the elongate member, the tube defining the second lumen at the interior of the elongate member.

60. The system of claim 57, wherein the fitting comprises a Luer fitting.

61. The system of claim 56, further comprising a tube that is a separate member relative to the elongate member, the tube defining the second lumen at the interior of the elongate member.

62. The system of claim 56, wherein a single unitary structure defines the plurality of filaments, and wherein a proximal end of the single unitary structure is fixedly attached to the second hub.

63. The system of claim 56, wherein the second lumen that is configured to receive the radiofrequency probe therein is devoid of an opening at a distal end thereof, such that a distal end of the radiofrequency probe remains in the second lumen during delivery of radiofrequency energy.

64. The system of claim 63, wherein the plurality of filaments extend distally beyond the distal end of the radiofrequency probe when the radiofrequency probe is fully inserted into the needle apparatus and when the plurality of filaments are in the deployed position, such that when radiofrequency energy is delivered to the radiofrequency probe, the plurality of filaments conduct radiofrequency energy that emanates from the radiofrequency probe beyond the distal end of the radiofrequency probe.

65. The system of claim 56, wherein the tip at least partially defines the second lumen, and wherein the second lumen is devoid of an opening at a distal end thereof.

66. The system of claim 65, wherein the plurality of filaments extend distally beyond a distal end of the radiofrequency probe when the radiofrequency probe is fully inserted into the needle apparatus and when the plurality of filaments are in the deployed position, such that when radiofrequency energy is delivered to the radiofrequency probe, the plurality of filaments conduct radiofrequency energy that emanates from the radiofrequency probe beyond the distal end of the radiofrequency probe.

67. The system of claim 56, wherein the needle apparatus is configured to maintain a distal end of the radiofrequency probe within the tip.

68. The system of claim 67, wherein the plurality of filaments extend distally beyond the distal end of the radiofrequency probe when the radiofrequency probe is fully inserted into the needle apparatus and when the plurality of filaments are in the deployed position, such that when radiofrequency energy is delivered to the radiofrequency probe, the plurality of filaments conduct radiofrequency energy that emanates from the radiofrequency probe beyond the distal end of the radiofrequency probe.

69. The system of claim 56, wherein the plurality of filaments extend distally beyond a distal end of the radiofrequency probe when the radiofrequency probe is fully inserted into the needle apparatus and when the plurality of filaments are in the deployed position, such that when radiofrequency energy is delivered to the radiofrequency probe, the plurality of filaments conduct radiofrequency energy that emanates from the radiofrequency probe beyond the distal end of the radiofrequency probe.

70. The system of claim 56, wherein a distal end of the radiofrequency probe contacts the conductive portion of the needle apparatus, when the radiofrequency probe is fully inserted into the second lumen, to thereby establish the electrically conductive path from the radiofrequency probe to the plurality of filaments.

71. The system of claim 56, wherein the conductive portion of the needle apparatus is positioned at the distal end of the needle apparatus.

72. The system of claim 56, further comprising a tube that comprises a conductive material, the tube being a separate member relative to the elongate member, wherein the conductive portion of the needle apparatus that is physically contacted by the radiofrequency probe comprises the conductive material of the tube.

\* \* \* \* \*